(12) United States Patent
Beer et al.

(10) Patent No.: US 12,220,345 B2
(45) Date of Patent: Feb. 11, 2025

(54) DEVICES, SYSTEMS, AND METHODS FOR TRAINING PELVIC FLOOR MUSCLES

(71) Applicant: RENOVIA INC., Boston, MA (US)

(72) Inventors: Marc D. Beer, Boston, MA (US); Ramon Jose Iglesias, Boston, MA (US); Yolanda Lorie, Boston, MA (US)

(73) Assignee: Axena Health, Inc., Auburndale, MA (US)

( * ) Notice: Subject to any disclaimer, the term of this patent is extended or adjusted under 35 U.S.C. 154(b) by 1303 days.

(21) Appl. No.: 16/759,060

(22) PCT Filed: Oct. 26, 2018

(86) PCT No.: PCT/US2018/057811
§ 371 (c)(1),
(2) Date: Apr. 24, 2020

(87) PCT Pub. No.: WO2019/084469
PCT Pub. Date: May 2, 2019

(65) Prior Publication Data
US 2020/0337888 A1    Oct. 29, 2020

Related U.S. Application Data

(60) Provisional application No. 62/625,301, filed on Feb. 1, 2018, provisional application No. 62/577,811, filed on Oct. 27, 2017.

(51) Int. Cl.
*A61B 5/391* (2021.01)
*A61B 5/00* (2006.01)
(Continued)

(52) U.S. Cl.
CPC .............. *A61F 6/08* (2013.01); *A61B 5/0004* (2013.01); *A61B 5/1107* (2013.01);
(Continued)

(58) Field of Classification Search
CPC ....... A61F 6/08; A61B 5/0004; A61B 5/1107; A61B 5/14539; A61B 5/14546;
(Continued)

(56) References Cited

U.S. PATENT DOCUMENTS 2,830,582 A    4/1958    Ljung
3,854,476 A    12/1974   Dickinson III et al.
(Continued)

FOREIGN PATENT DOCUMENTS

CA    2625428 A1    7/2007
CA    2862928 A1    8/2013
(Continued)

OTHER PUBLICATIONS

U.S. Appl. No. 18/157,453, Iglesias.
(Continued)

*Primary Examiner* — Ankit D Tejani
*Assistant Examiner* — Joshua Brendon Solomon
(74) *Attorney, Agent, or Firm* — Clark & Elbing LLP

(57) ABSTRACT

Featured are intravaginal devices and methods of using the devices to observe the state of an individual's pelvic floor muscles in order to diagnose, treat, or prevent pelvic floor disorders (e.g., pelvic organ prolapse and incontinence) and their accompanying symptoms and methods of using the devices to treat or prevent vaginal disorders (e.g., skin laxity) in a subject using an energy transmitter (e.g., a radiofrequency transmitter).

10 Claims, 30 Drawing Sheets
(30 of 30 Drawing Sheet(s) Filed in Color)

(51) Int. Cl.
| | |
|---|---|
| *A61B 5/11* | (2006.01) |
| *A61B 5/145* | (2006.01) |
| *A61B 5/22* | (2006.01) |
| *A61F 6/08* | (2006.01) |
| *A61N 1/05* | (2006.01) |
| *A61N 1/40* | (2006.01) |

(52) U.S. Cl.
CPC ...... *A61B 5/14539* (2013.01); *A61B 5/14546* (2013.01); *A61B 5/227* (2013.01); *A61B 5/391* (2021.01); *A61B 5/4294* (2013.01); *A61B 5/4337* (2013.01); *A61B 5/6847* (2013.01); *A61B 5/6857* (2013.01); *A61B 5/7435* (2013.01); *A61B 5/7475* (2013.01); *A61N 1/0524* (2013.01); *A61N 1/403* (2013.01); *A61B 5/0002* (2013.01); *A61B 2560/0487* (2013.01); *A61B 2562/0219* (2013.01); *A61B 2562/063* (2013.01)

(58) Field of Classification Search
CPC ....... A61B 5/227; A61B 5/391; A61B 5/4294; A61B 5/4337; A61B 5/6847; A61B 5/6857; A61B 5/7435; A61B 5/7475; A61B 5/0002; A61B 5/0077; A61B 5/6856; A61B 5/743; A61B 2560/0487; A61B 2562/0219; A61B 2562/063; A61N 1/0524; A61N 1/403; A61N 1/36007
See application file for complete search history.

(56) References Cited

U.S. PATENT DOCUMENTS

| | | |
|---|---|---|
| 4,669,478 A | 6/1987 | Robertson |
| 4,873,990 A | 10/1989 | Holmes et al. |
| D309,866 S | 8/1990 | Fukuda et al. |
| D310,275 S | 8/1990 | Su |
| 5,049,132 A | 9/1991 | Shaffer et al. |
| 5,328,077 A | 7/1994 | Lou |
| 5,386,836 A | 2/1995 | Biswas |
| 5,406,961 A | 4/1995 | Artal |
| 5,562,717 A | 10/1996 | Tippey et al. |
| 5,603,685 A | 2/1997 | Tutrone, Jr. |
| 5,674,238 A | 10/1997 | Sample et al. |
| 5,924,984 A | 7/1999 | Rao |
| 6,001,060 A | 12/1999 | Churchill et al. |
| 6,021,781 A | 2/2000 | Thompson et al. |
| 6,039,701 A | 3/2000 | Sliwa et al. |
| 6,056,699 A | 5/2000 | Sohn et al. |
| 6,080,118 A | 6/2000 | Blythe |
| 6,086,549 A | 7/2000 | Neese et al. |
| 6,264,582 B1 | 7/2001 | Remes |
| 6,272,371 B1 | 8/2001 | Shlomo |
| D458,681 S | 6/2002 | Sherlock et al. |
| 6,413,206 B2 | 7/2002 | Biswas |
| 6,432,037 B1 | 8/2002 | Eini et al. |
| 6,511,427 B1 | 1/2003 | Sliwa, Jr. et al. |
| 6,652,565 B1 | 11/2003 | Shimada et al. |
| 6,672,996 B2 | 1/2004 | Ross et al. |
| 6,679,854 B2 | 1/2004 | Honda et al. |
| 6,741,895 B1 | 5/2004 | Gafni et al. |
| D491,079 S | 6/2004 | Lim |
| D491,274 S | 6/2004 | Dubniczki et al. |
| 6,816,744 B2 | 11/2004 | Garfield et al. |
| 7,079,882 B1 | 7/2006 | Schmidt |
| 7,104,950 B2 | 9/2006 | Levy |
| D535,203 S | 1/2007 | Chen |
| D548,359 S | 8/2007 | Illein et al. |
| 7,577,476 B2 | 8/2009 | Hochman et al. |
| 7,608,037 B2 | 10/2009 | Levy |
| 7,628,744 B2 | 12/2009 | Hoffman et al. |
| 7,645,220 B2 | 1/2010 | Hoffman et al. |
| 7,736,298 B2 | 6/2010 | Guerquin et al. |
| 7,837,682 B2 | 11/2010 | Ostrovsky et al. |
| 7,892,179 B2 | 2/2011 | Rieth |
| 7,955,241 B2 | 6/2011 | Hoffman et al. |
| 7,957,794 B2 | 6/2011 | Hochman et al. |
| D651,531 S | 1/2012 | Rothman |
| 8,147,429 B2 | 4/2012 | Mittal et al. |
| 8,360,954 B2 | 1/2013 | Kim |
| 8,623,004 B2 | 1/2014 | Johnson et al. |
| 8,715,204 B2 | 5/2014 | Webster et al. |
| 8,728,140 B2 | 5/2014 | Feemster et al. |
| 8,740,767 B2 | 6/2014 | Rosen et al. |
| 8,751,003 B2 | 6/2014 | DiUbaldi et al. |
| 8,805,472 B2 | 8/2014 | Iglesias |
| 8,821,407 B2 | 9/2014 | Kirsner |
| 8,914,111 B2 | 12/2014 | Haessler |
| 8,983,627 B2 | 3/2015 | Pelger et al. |
| 9,155,885 B2 | 10/2015 | Wei et al. |
| 9,248,285 B2 | 2/2016 | Haessler |
| D759,813 S | 6/2016 | Newman et al. |
| D759,814 S | 6/2016 | Newman et al. |
| 9,381,351 B2 | 7/2016 | Haessler |
| 9,408,685 B2 | 8/2016 | Hou et al. |
| 9,656,067 B2 | 5/2017 | Pelger et al. |
| D800,898 S | 10/2017 | Sanders et al. |
| 9,861,316 B2 | 1/2018 | Egorov |
| 9,970,923 B2 | 5/2018 | Sturman et al. |
| 9,974,635 B2 | 5/2018 | Rosen et al. |
| D832,437 S | 10/2018 | Zeltwanger et al. |
| D841,155 S | 2/2019 | McMenamin et al. |
| D845,478 S | 4/2019 | Luke |
| D846,120 S | 4/2019 | Wallis et al. |
| D852,069 S | 6/2019 | Fu |
| D853,035 S | 7/2019 | Moretti |
| D855,825 S | 8/2019 | Parsons et al. |
| 10,470,862 B2 | 11/2019 | Iglesias |
| D877,895 S | 3/2020 | Sanders et al. |
| D888,949 S | 6/2020 | Beer et al. |
| D889,649 S | 7/2020 | Beer et al. |
| D893,026 S | 8/2020 | Leather |
| D896,958 S | 9/2020 | Beer et al. |
| D896,959 S | 9/2020 | Beer et al. |
| D897,530 S | 9/2020 | Beer et al. |
| D898,911 S | 10/2020 | Beer et al. |
| D899,593 S | 10/2020 | Beer et al. |
| D903,853 S | 12/2020 | Wiegerinck |
| D903,896 S | 12/2020 | Tianhao et al. |
| D908,160 S | 1/2021 | Sun |
| D909,679 S | 2/2021 | Chen |
| D910,851 S | 2/2021 | Lagrange et al. |
| D918,390 S | 5/2021 | Ollivier |
| D919,083 S | 5/2021 | Lee |
| D923,806 S | 6/2021 | Bunger von Wurmb et al. |
| D923,876 S | 6/2021 | Hasegawa |
| 11,135,085 B2 | 10/2021 | Mikkonen et al. |
| D938,581 S | 12/2021 | Floyd et al. |
| 11,266,343 B2 | 3/2022 | Iglesias |
| D956,229 S | 6/2022 | Beer et al. |
| D958,987 S | 7/2022 | Beer et al. |
| 11,426,625 B2 | 8/2022 | Iglesias et al. |
| 11,426,626 B2 | 8/2022 | Beer et al. |
| 2001/0001125 A1 | 5/2001 | Schulman et al. |
| 2001/0047132 A1 | 11/2001 | Johnson et al. |
| 2002/0022836 A1 | 2/2002 | Goble et al. |
| 2002/0111586 A1 | 8/2002 | Mosel et al. |
| 2002/0143275 A1 | 10/2002 | Sarvazyan et al. |
| 2003/0028180 A1 | 2/2003 | Franco |
| 2003/0087734 A1 | 5/2003 | Kring et al. |
| 2004/0236223 A1 | 11/2004 | Barnes et al. |
| 2004/0260207 A1 | 12/2004 | Eini et al. |
| 2005/0148447 A1 | 7/2005 | Nady |
| 2005/0177067 A1 | 8/2005 | Tracey et al. |
| 2005/0256423 A1 | 11/2005 | Kirsner |
| 2006/0036188 A1 | 2/2006 | Hoffman et al. |
| 2006/0074289 A1 | 4/2006 | Adler et al. |
| 2006/0084848 A1 | 4/2006 | Mitchnick |
| 2006/0211911 A1 | 9/2006 | Jao et al. |
| 2007/0066880 A1 | 3/2007 | Lee et al. |
| 2007/0232882 A1 | 10/2007 | Glossop et al. |
| 2007/0255090 A1 | 11/2007 | Addington et al. |
| 2007/0265675 A1 | 11/2007 | Lund et al. |

(56) References Cited

U.S. PATENT DOCUMENTS

| | | |
|---|---|---|
| 2007/0270686 A1 | 11/2007 | Ritter et al. |
| 2008/0077053 A1 | 3/2008 | Epstein et al. |
| 2008/0139876 A1 | 6/2008 | Kim |
| 2008/0146941 A1 | 6/2008 | Dala-Krishna |
| 2008/0149109 A1 | 6/2008 | Ziv |
| 2008/0154131 A1 | 6/2008 | Lee et al. |
| 2008/0171950 A1 | 7/2008 | Franco |
| 2008/0300658 A1 | 12/2008 | Meskens |
| 2009/0024001 A1 | 1/2009 | Parks et al. |
| 2009/0149740 A1 | 6/2009 | Hoheisel |
| 2009/0216071 A1 | 8/2009 | Zipper |
| 2009/0270963 A1 | 10/2009 | Pelger et al. |
| 2009/0306509 A1 | 12/2009 | Pedersen et al. |
| 2010/0069784 A1 | 3/2010 | Blaivas |
| 2010/0174218 A1 | 7/2010 | Shim |
| 2010/0222708 A1 | 9/2010 | Hitchcock et al. |
| 2010/0249576 A1 | 9/2010 | Askarinya et al. |
| 2010/0262049 A1 | 10/2010 | Novak et al. |
| 2010/0298895 A1 | 11/2010 | Ghaffari et al. |
| 2011/0054357 A1 | 3/2011 | Egorov et al. |
| 2011/0077500 A1 | 3/2011 | Shakiba |
| 2011/0144458 A1 | 6/2011 | Gauta |
| 2011/0190580 A1 | 8/2011 | Bennett et al. |
| 2011/0190595 A1 | 8/2011 | Bennett et al. |
| 2011/0196263 A1 | 8/2011 | Egorov et al. |
| 2012/0016258 A1 | 1/2012 | Webster et al. |
| 2012/0245490 A1 | 9/2012 | Fausett et al. |
| 2012/0265044 A1 | 10/2012 | Broens |
| 2012/0265049 A1 | 10/2012 | Iglesias |
| 2013/0035611 A1 | 2/2013 | White |
| 2013/0053627 A1 | 2/2013 | Bercovich et al. |
| 2013/0130871 A1 | 5/2013 | McCoy et al. |
| 2013/0144191 A1 | 6/2013 | Egorov et al. |
| 2013/0184567 A1 | 7/2013 | Xie et al. |
| 2013/0192606 A1 | 8/2013 | Ziv et al. |
| 2013/0237771 A1 | 9/2013 | Runkewitz et al. |
| 2013/0324380 A1 | 12/2013 | Horsley |
| 2014/0066813 A1 | 3/2014 | Daly et al. |
| 2014/0073879 A1 | 3/2014 | Cantor et al. |
| 2014/0088471 A1 | 3/2014 | Leivseth et al. |
| 2014/0155225 A1 | 6/2014 | Sedic |
| 2014/0213927 A1 | 7/2014 | Webster et al. |
| 2014/0275743 A1 | 9/2014 | Rosen et al. |
| 2014/0288612 A1 | 9/2014 | Addington et al. |
| 2014/0296705 A1 | 10/2014 | Iglesias |
| 2014/0309550 A1 | 10/2014 | Iglesias |
| 2015/0032030 A1 | 1/2015 | Iglesias |
| 2015/0112230 A1 | 4/2015 | Iglesias |
| 2015/0112231 A1 | 4/2015 | Iglesias |
| 2015/0133832 A1 | 5/2015 | Courtion et al. |
| 2015/0196802 A1 | 7/2015 | Siegel |
| 2015/0282763 A1 | 10/2015 | Rosenshein |
| 2016/0008664 A1 | 1/2016 | Siegel |
| 2016/0022198 A1 | 1/2016 | De Laat |
| 2016/0051354 A1 | 2/2016 | Patankar et al. |
| 2016/0074276 A1 | 3/2016 | Scheuring et al. |
| 2016/0121105 A1 | 5/2016 | Lee et al. |
| 2016/0279469 A1 | 9/2016 | Rose |
| 2016/0346610 A1 | 12/2016 | Iglesias et al. |
| 2017/0231709 A1 | 8/2017 | Gupta et al. |
| 2017/0281072 A1 | 10/2017 | Iglesias |
| 2017/0281299 A1 | 10/2017 | Iglesias |
| 2017/0291012 A1 | 10/2017 | Iglesias |
| 2017/0303843 A1 | 10/2017 | Iglesias |
| 2017/0312530 A1 | 11/2017 | Schilling et al. |
| 2017/0332959 A1 | 11/2017 | Bartlett |
| 2018/0021121 A1 | 1/2018 | Zeltwanger et al. |
| 2018/0146892 A1 | 5/2018 | Billard |
| 2018/0199816 A1 | 7/2018 | Kalt et al. |
| 2019/0133738 A1 | 5/2019 | Rosen et al. |
| 2019/0160332 A1* | 5/2019 | Beer .................. A63B 23/00 |
| 2020/0029812 A1 | 1/2020 | Govari et al. |
| 2020/0069161 A1 | 3/2020 | Schentag et al. |
| 2020/0146800 A1 | 5/2020 | Iglesias |
| 2020/0337888 A1 | 10/2020 | Beer et al. |
| 2020/0405142 A1 | 12/2020 | Whitaker |
| 2021/0069513 A1 | 3/2021 | Beer et al. |
| 2021/0106787 A1 | 4/2021 | Iglesias |
| 2021/0145353 A1 | 5/2021 | Iglesias |
| 2021/0161403 A1 | 6/2021 | Beer et al. |
| 2021/0321983 A1 | 10/2021 | Miyamoto |
| 2021/0353195 A1 | 11/2021 | Beer et al. |
| 2023/0201659 A1 | 6/2023 | Iglesias et al. |
| 2023/0201660 A1 | 6/2023 | Bohorquez et al. |
| 2023/0225847 A1 | 7/2023 | Iglesias |

FOREIGN PATENT DOCUMENTS

| | | |
|---|---|---|
| CN | 103622710 A | 3/2014 |
| CN | 204839545 U | 12/2015 |
| DE | 10345282 B3 | 4/2005 |
| DE | 202018103016 U1 | 6/2018 |
| EP | 0268972 A2 | 6/1988 |
| EP | 2689724 A1 | 1/2014 |
| EP | 2809231 A4 | 9/2015 |
| EP | 3366212 A1 | 8/2018 |
| GB | 2492754 A | 1/2013 |
| JP | 2002-143133 A | 5/2002 |
| JP | 2008-532578 A | 8/2008 |
| JP | 2011-183167 A | 9/2011 |
| RU | 2307636 C1 | 10/2007 |
| WO | WO-96/05768 A1 | 2/1996 |
| WO | WO-99/05963 A1 | 2/1999 |
| WO | WO-00/09013 A1 | 2/2000 |
| WO | WO-00/23030 A1 | 4/2000 |
| WO | WO-01/37732 A1 | 5/2001 |
| WO | WO-02/17987 A2 | 3/2002 |
| WO | WO-2006/107930 A2 | 10/2006 |
| WO | WO-2007/136266 A1 | 11/2007 |
| WO | WO-2010/131252 A2 | 11/2010 |
| WO | WO-2011/050252 A1 | 4/2011 |
| WO | WO-2011/121591 A2 | 10/2011 |
| WO | WO-2011/159906 A2 | 12/2011 |
| WO | WO-2012/079127 A1 | 6/2012 |
| WO | WO-2012/138232 A1 | 10/2012 |
| WO | WO-2013/082006 A1 | 6/2013 |
| WO | WO-2013/115310 A1 | 8/2013 |
| WO | WO-2013/116310 A1 | 8/2013 |
| WO | WO-2015/103629 A1 | 7/2015 |
| WO | WO-2016/026914 A2 | 2/2016 |
| WO | WO-2016/042310 A1 | 3/2016 |
| WO | WO-2016/067023 A1 | 5/2016 |
| WO | WO-2016/119002 A1 | 8/2016 |
| WO | WO-2016/203485 A1 | 12/2016 |
| WO | WO-2017/149688 A1 | 9/2017 |
| WO | WO-2018/023037 A1 | 2/2018 |
| WO | WO-2019/084468 A1 | 5/2019 |
| WO | WO-2019/084469 A1 | 5/2019 |
| WO | WO-2019/200222 A1 | 10/2019 |
| WO | WO-2019/210204 A1 | 10/2019 |
| WO | WO-2020/092343 A1 | 5/2020 |

OTHER PUBLICATIONS

U.S. Appl. No. 17/822,954, Iglesias et al.
U.S. Appl. No. 17/926,192, Bohorquez et al.
Notice of Reasons for Refusal for Japanese Patent Application No. 2020-143711, mailed May 9, 2022 (7 pages).
Office Action for Chinese Patent Application No. 201780060078.4, issued Apr. 13, 2022 (19 pages).
Extended European Search Report for European Patent Application No. 19878836.6, dated Jun. 1, 2022 (7 pages).
Office Action for Canadian Patent Application No. 2,936,061, dated Jun. 23, 2022 (4 pages).
Notice of Last Preliminary Rejection for Korean Patent Application No. 10-2019-7005863, dated Jul. 28, 2022 (4 pages).
Office Action for Brazilian Patent Application No. BR112020008231-7, dated Sep. 7, 2022 (5 pages) (Informal translation of Office Action included).
Extended European Search Report dated Aug. 16, 2017 issued in related EP Application No. 15733078.8 filed Aug. 2, 2016 (6 pages).

(56) References Cited

OTHER PUBLICATIONS

International Search Report and Written Opinion, dated Mar. 26, 2015, issued in International Application No. PCT/US2015/010356, filed on Jan. 6, 2015 (5 pages).
Office Action for Chinese Patent Application No. 201880083895.6 dated Oct. 25, 2022 (8 pages).
Office Action for Chinese Patent Application No. 201880083895.6, dated Feb. 8, 2022 (24 pages).
Extended European Search Report for European Patent Application No. 19786241.0, dated Apr. 29, 2022 (10 pages).
Office Action for European Patent Application No. 17203166.8, dated Aug. 29, 2023 (6 pages).
Communication pursuant to Article 94(3) EPC for European Patent Application No. 12852598.7, dated Jun. 6, 2018 (4 pages).
Examination Report for Canadian Patent Application No. 2,856,724, dated Oct. 18, 2018 (3 pages).
Extended European Search Report for European Patent Application No. 17203166.8, dated Jul. 31, 2018 (10 pages).
First Examination Report for Australian Patent Application No. 2017245476, dated Sep. 12, 2018 (3 pages).
First Examination Report for Australian Patent Application No. 2018200715, dated Jun. 26, 2018 (4 pages).
First Office Action for Mexican Patent Application No. MX/a/2014/006219, dated Jul. 31, 2017 (3 pages).
Glazer et al., "Pelvic floor muscle biofeedback in the treatment of urinary incontinence: A literature review," Appl Psychophysiol Biofeedback. 31(3):187-201 (2006) (Abstract only).
International Search Report and Written Opinion for International Application No. PCT/US17/44444, mailed Oct. 19, 2017 (21 pages).
International Search Report and Written Opinion for International Application No. PCT/US18/57811, mailed Jan. 29, 2019 (18 pages).
Parekh et al., "The role of pelvic floor exercises on post-prostatectomy incontinence," J Urol. 170(1):130-33 (2003) (Abstract Only) (2 pages).
Rosenbaum, "Pelvic floor involvement in male and female sexual dysfunction and the role of pelvic floor rehabilitation in treatment: a literature review," J Sex Med. 4(1):4-13 (2007) (Abstract only) (2 pages).
Second Examination Report for Canadian Patent Application No. 2,862,928, dated Nov. 20, 2018 (5 pages).
International Preliminary Report on Patentability for International Application No. PCT/US2017/044444, mailed Feb. 7, 2019 (14 pages).
Moen et al., "Pelvic floor muscle function in women presenting with pelvic floor disorders," Int Urogynecol J Pelvic Floor Dysfunct. 20(7):843-6 (2009).
Kandadai et al., "Correct Performance of Pelvic Muscle Exercises in Women Reporting Prior Knowledge," Female Pelvic Med Reconstr Surg. 21(3):135-40 (2015).
Rosenblatt et al., "Interactive Pelvic Floor Muscle Training for Female Urinary Incontinence," Renovia, Inc., retrieved Apr. 30, 2019 from <renoviainc.com/wp-content/uploads/2018/04/REN005.01-White-Paper-12Apr18-FINAL.pdf> (2018) (6 pages).

Malcovati et al., Interface Circuitry and Microsystems. *MEMS—A Practical Guide to Design, Analysis, and Applications*. Jan G. Korvink and Oliver Paul, 901-942 (2006).
*Gray's Anatomy, 39th Edition*, Churchill Livingstone, p. 1290, definition of "Bladder neck" (2005) (3 pages).
*Stedman's Medical Dictionary, 28th Edition*, Lippincott Williams & Wilkins (LWW), p. 2072 (2006).
Rosenbaum et al., "The Role of Pelvic Floor Pysical Therapy in the Treatment of Pelvic and Genital Pain-Related Sexual Dysfunction," J Sex Med. 5(3): 513-23 (2008).
Summons to attend oral proceedings pursuant to Rule 115(1) EPC, issued on Aug. 3, 2017 by the European Patent Office related to the European Patent Application No. 13743383.5 (10 pages).
International Search Report and Written Opinion for International Application No. PCT/US2012/066613, mailed Feb. 6, 2013 (5 pages).
International Search Report and Written Opinion for International Application No. PCT/US2019/029400, mailed Jul. 10, 2019 (17 pages).
International Search Report and Written Opinion for International Application No. PCT/US2019/027168, mailed Aug. 12, 2019 (39 pages).
Rosenblatt et al., "Evaluation of an accelerometer-based digital health system for the treatment of female urinary incontinence: A pilot study," Neurourol Urodyn. 38(7): 1944-1952 (2019).
Nygaard et al., "Efficacy of pelvic floor muscle exercises in women with stress, urge, and mixed urinary incontinence," Am J Obstet Gynecol. 174(1 Pt 1):120-125 (1996) (Abstract only).
International Search Report and Written Opinion for International Application No. PCT/US2019/058527, mailed Feb. 21, 2020 (18 pages).
Office Action for Japanese Patent Application No. 2019-504938, dated May 18, 2021 (10 pages).
International Search Report and Written Opinion for International Application No. PCT/US2021/033155, mailed Aug. 25, 2021 (19 pages).
Communication pursuant to Article 94(3) EPC for European Patent Application No. 15733078.8, dated Aug. 24, 2021 (8 pages).
Office Action for Japanese Patent Application No. 2020-143711, dated Sep. 8, 2021 (4 pages).
First Examination Report for Australian Patent Application No. 2020281099, dated Nov. 2, 2021 (6 pages).
Office Action for Brazilian Patent Application No. BR112019001746-1, dated Dec. 10, 2021 (5 pages).
Extended European Search Report for European Application No. 19793343.5, dated Jan. 27, 2022 (7 pages).
Notice of Preliminary Rejection for Korean Patent Application No. 10-2019-7005863, dated Jan. 26, 2022 (17 pages).
Office Action for Chinese Patent Application No. 201780060078.4 issued Jan. 17, 2022 (20 pages).
Office Action for Japanese Patent Application No. 2019-504938 dated Feb. 8, 2022 (13 pages).

\* cited by examiner

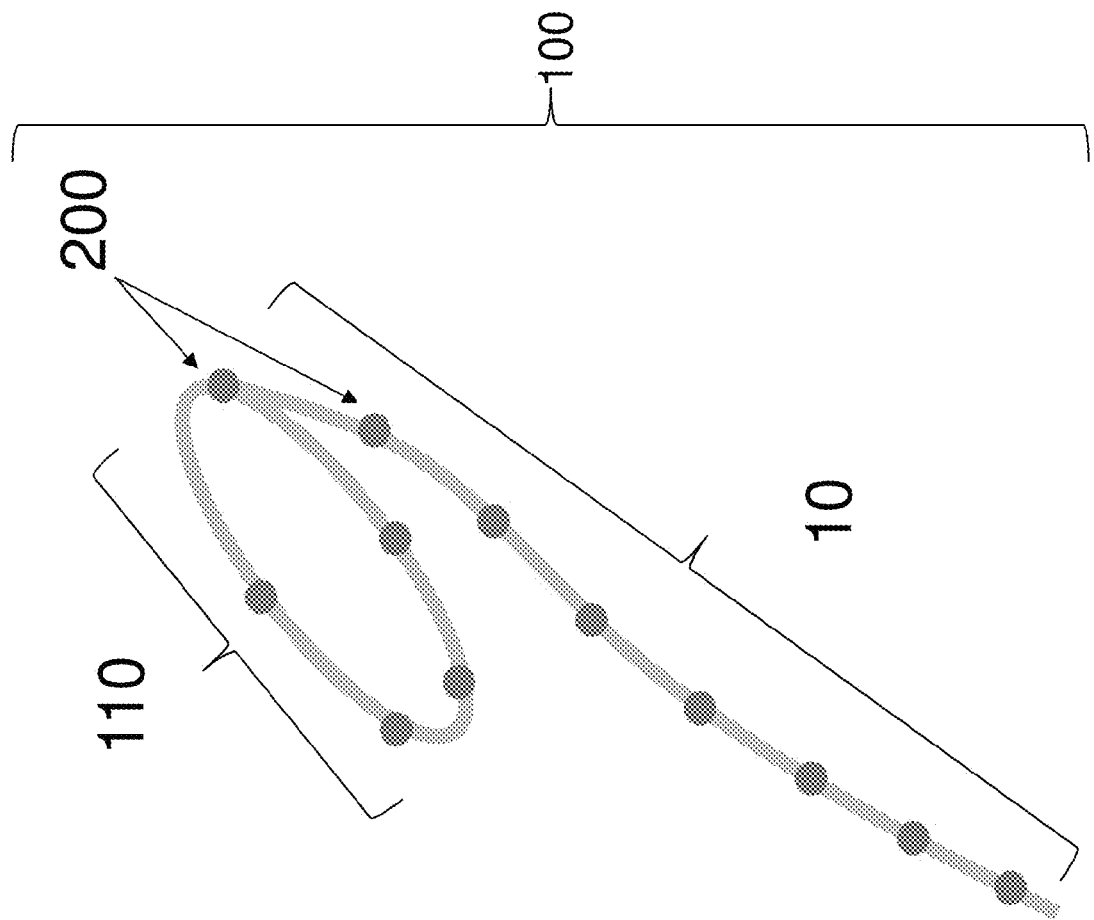

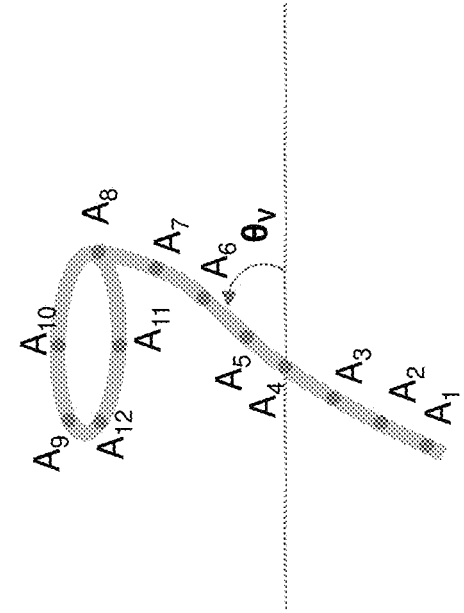
FIG. 4B
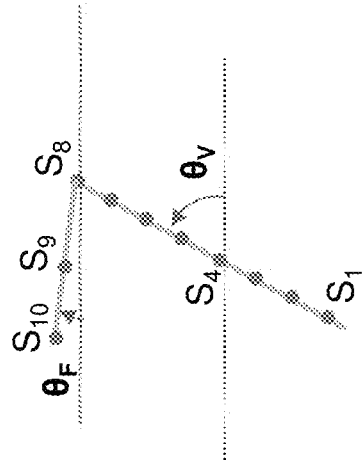
FIG. 4D
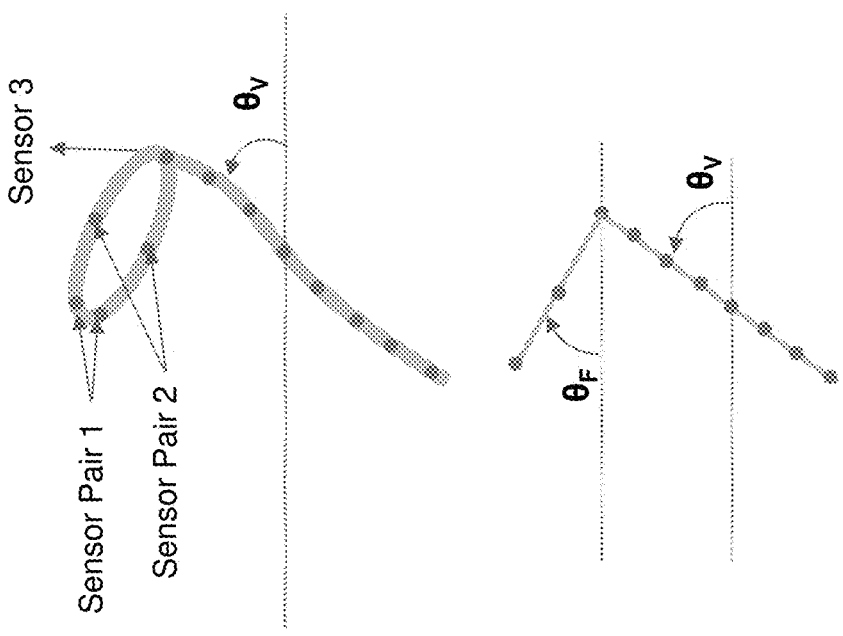
FIG. 4A
FIG. 4C

FIG. 6B

| Subject | Length (cm) |
|---|---|
| 002 | 11.5 |
| 004 | 9.6 |
| 005 | 8.4 |
| 006 | 12.2 |
| 007 | 9.6 |
| 008 | 9.0 |
| 009 | 12.2 |
| 010 | 10.3 |
| 011 | 7.7 |
| 012 | 12.2 |
| Mean | 10.3 |
| Standard Deviation | 1.67 |
| Range | 7.7 — 12.2 |

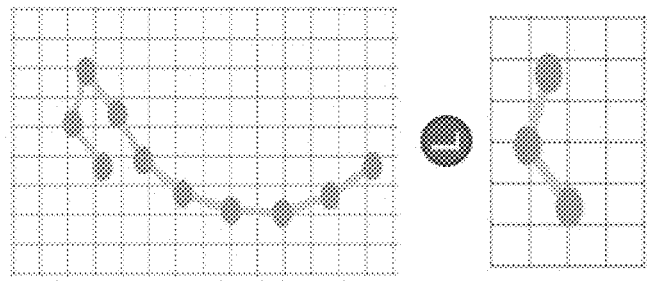
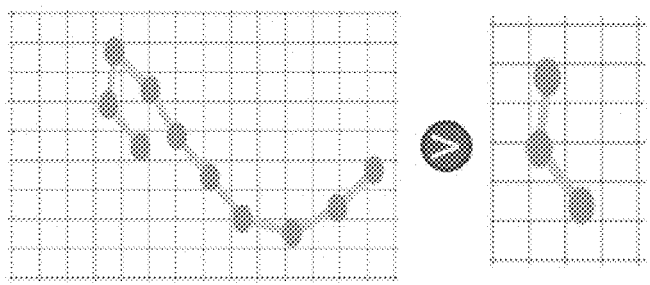
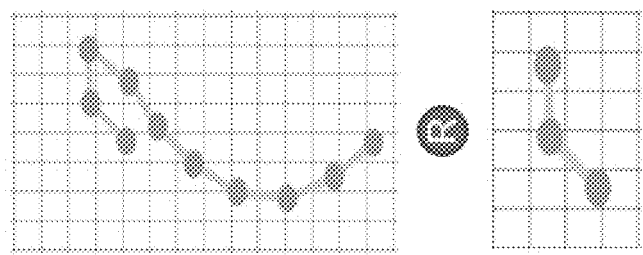
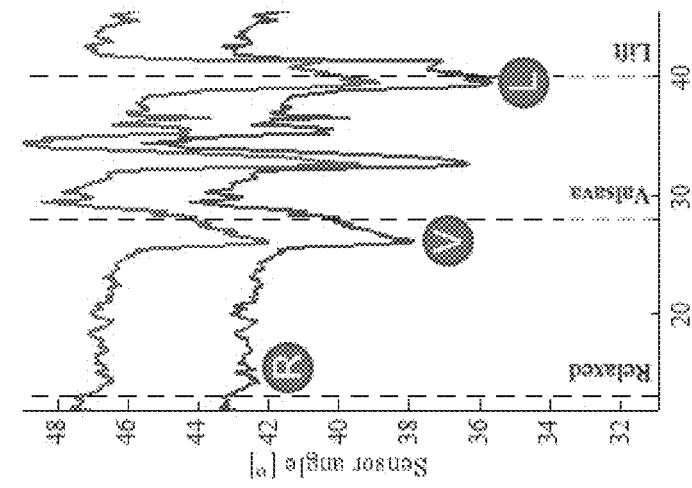

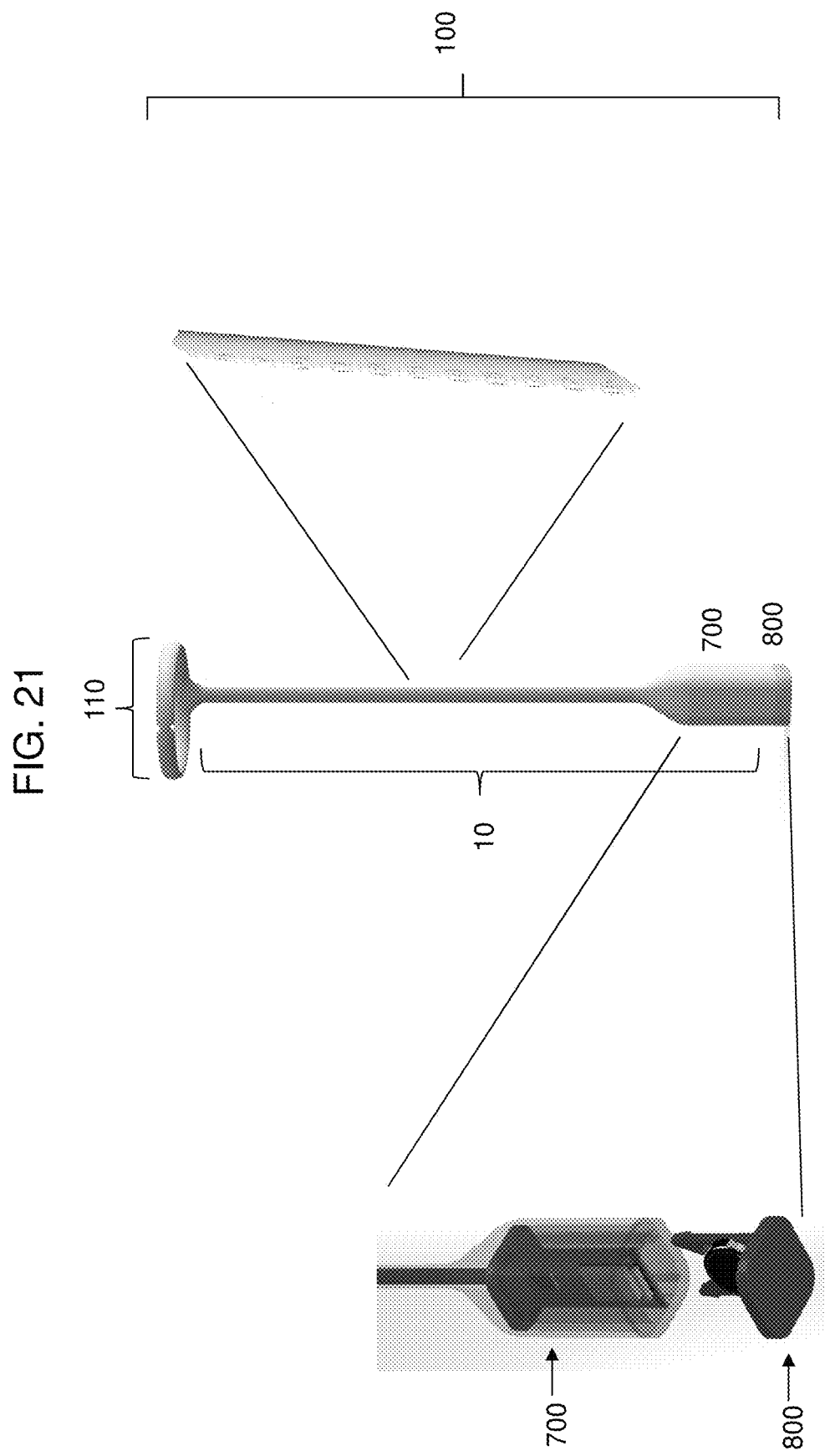

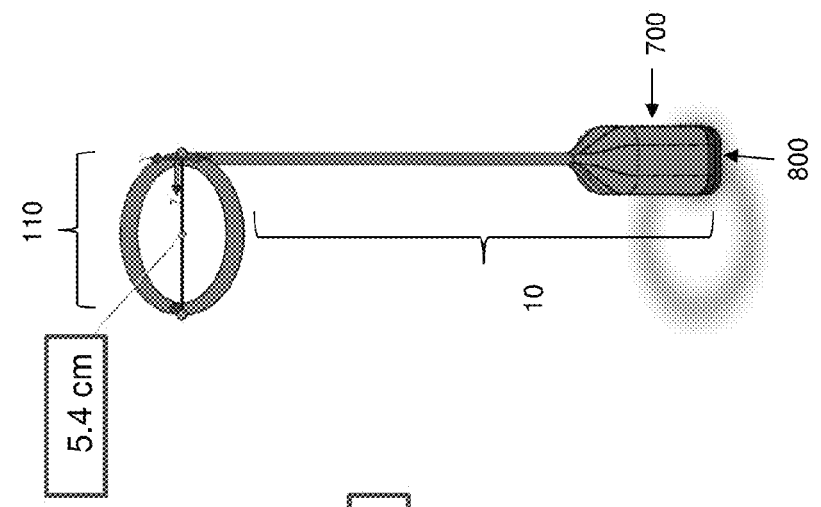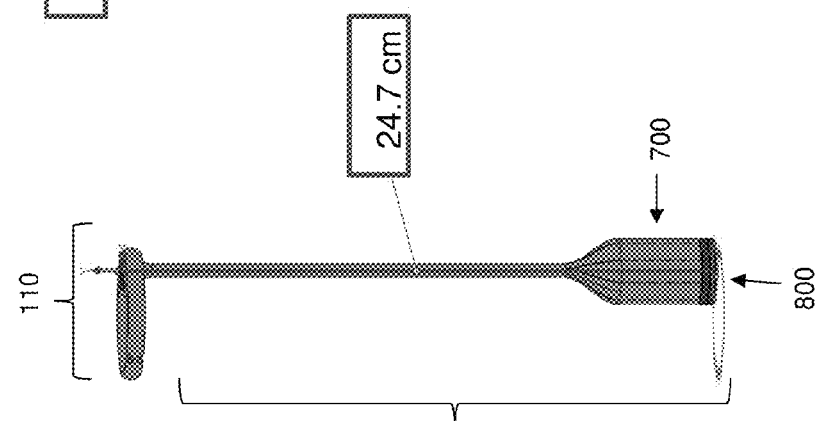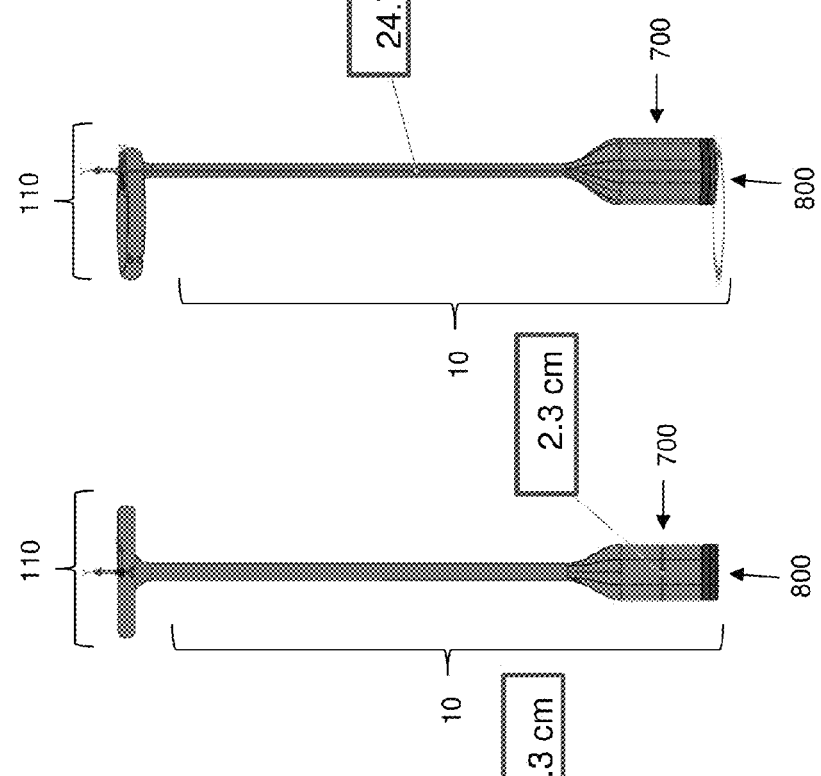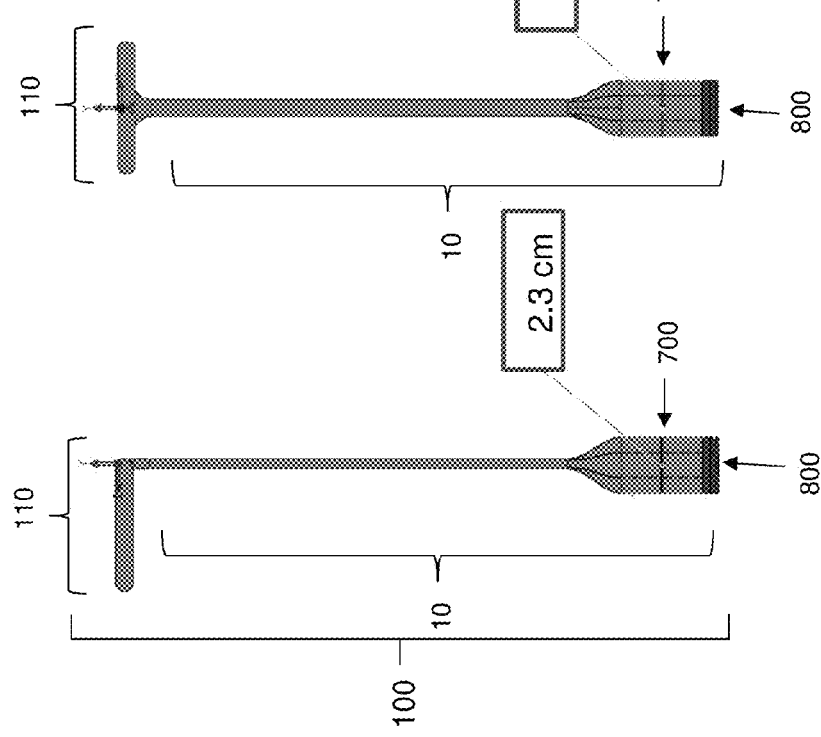

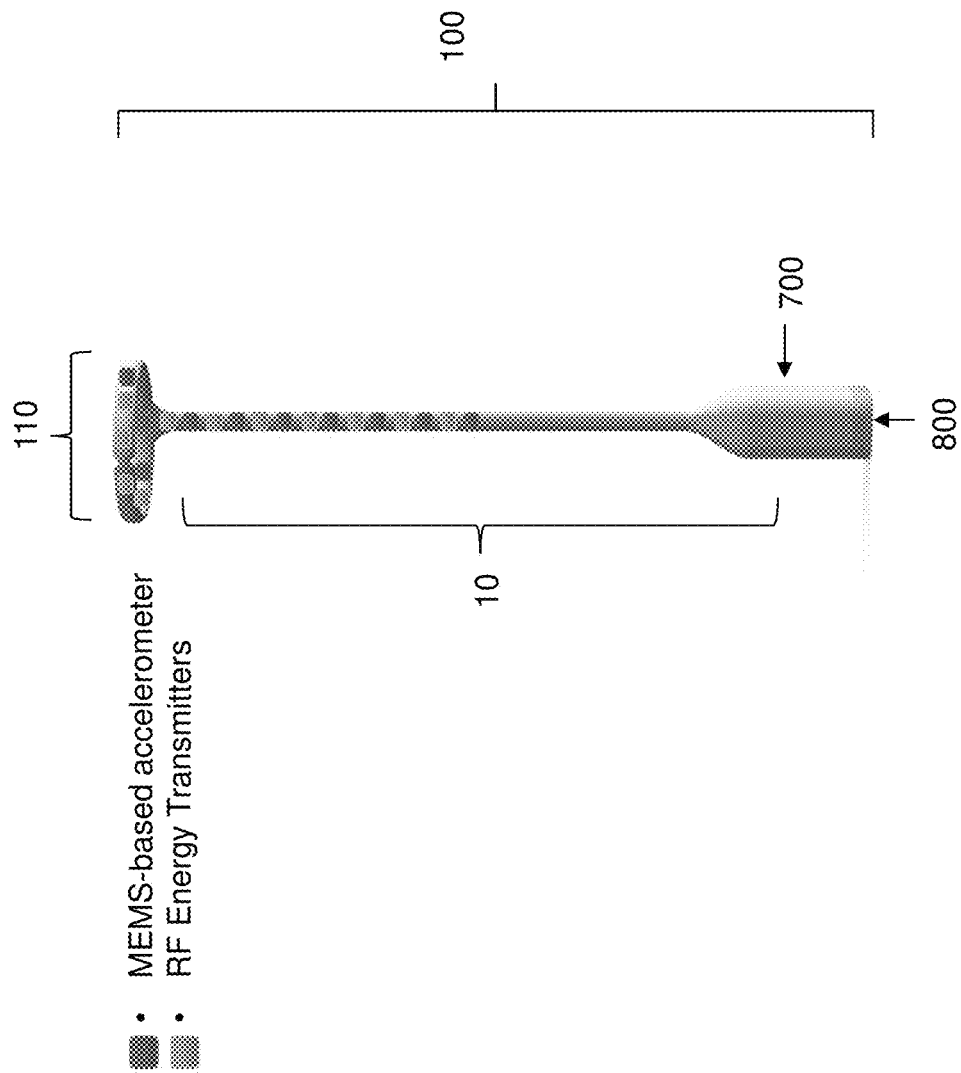

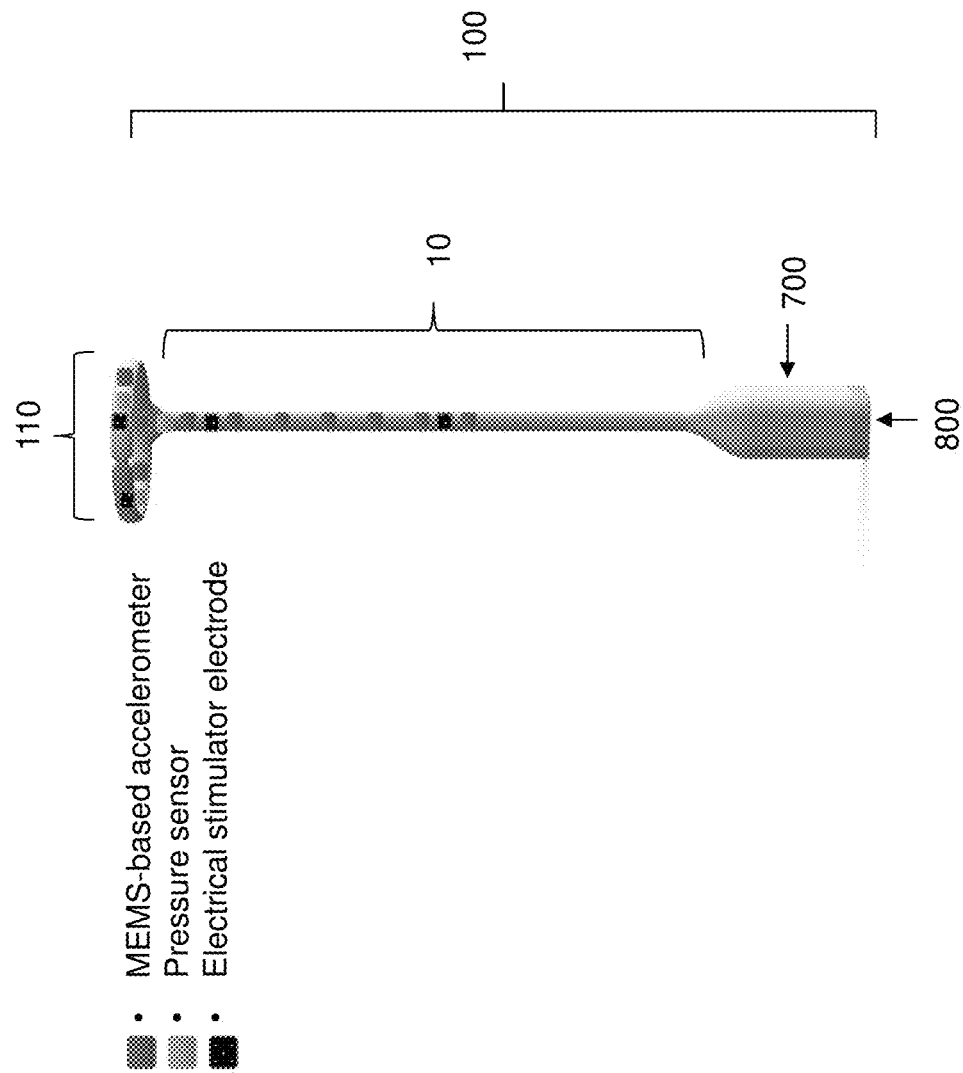

DEVICES, SYSTEMS, AND METHODS FOR TRAINING PELVIC FLOOR MUSCLES

BACKGROUND

Pelvic floor disorders (PFDs) are a group of conditions that occur predominantly in women and that are associated with weakened (e.g., hypotonic) or tense (e.g., hypertonic) pelvic floor (PF) muscles. Many common factors contribute to the weakening or tightening of the pelvic floor muscles in women, such as, for example, pregnancy, vaginal childbirth, pelvic surgery, aging, genetic predisposition, neurological disease, and weight gain. In the United States, PFDs occur in 24% of women, with 16% of women experiencing urinary incontinence (UI), 3% experiencing pelvic organ prolapse (POP), and 9% experiencing anal or fecal incontinence (FI). The prevalence of PFDs increases with age, such that 10% of women aged 20-39 and 50% of women aged 80 years or older will experience at least one PFD. The number of women in the United States having at least one PFD is estimated to increase from 28.1 million in 2010 to 43.8 million in 2050 (Memon et al., *Womens Health (Lond. Engl.)*. 9(3), 2013).

There exists a need for methods and devices for diagnosing, monitoring, and treating PFDs.

SUMMARY OF THE INVENTION

In one aspect, the invention features an intravaginal device comprising a main body having an outer edge configured to contact a vaginal wall (e.g., in proximity to the cervix) or a vaginal fornix and an internal diameter sized to encircle a cervix or vaginal cuff and a tether connected to the main body and comprising one or more motion-detecting sensors (e.g., pelvic floor muscle movement) located on the tether at a distance of 7 cm or less from the main body.

In another aspect, the invention features an intravaginal device comprising a main body having an outer edge configured to contact a vaginal wall (e.g., in proximity to the cervix) or vaginal fornix and an internal diameter sized to encircle a cervix or vaginal cuff, a tether connected to the main body and comprising one or more motion-detecting sensors (e.g., sensors for detecting pelvic floor muscle movement) located on the tether; and/or one or more energy transmitters (e.g., radio frequency (RF) energy transmitters, lasers, or electrical stimulators). The one or more motion-detecting sensors and/or the one or more energy transmitters (e.g., RF transmitters) may be located on the tether at a distance of 7 cm or less from the main body.

In another aspect, the invention features an intravaginal device comprising a main body having an outer edge configured to contact a vaginal wall or vaginal fornix and an internal diameter sized to encircle a cervix or vaginal cuff and a tether connected to the main body and comprising one or energy transmitters located on the tether. The intravaginal device may further comprise one or more motion-detecting sensors, optionally wherein the one or more motion-detecting sensors are located on the tether at a distance of 7 cm or less from the main body.

In another aspect, the invention features an intravaginal device comprising a main body having an outer edge configured to contact a vaginal wall or vaginal fornix and an internal diameter sized to encircle a cervix or vaginal cuff and a tether connected to the main body and comprising one or more motion-detecting sensors and/or one or more energy transmitters (e.g., RF transmitter, lasers, or electrical stimulators) located on the tether. The tether can be configured to have one or more separable pieces. The separable piece(s) of the tether may be joined by a magnetic or interlocking connection. The separable piece(s) of the tether may contain an electrical connection at a junction there-between. One of the pieces may be connected to an external power source. The external power source may provide an amount of energy to the separable piece(s) of the tether, the tether connected to the main body, and/or to the main body (e.g., 1 mW-500 W, e.g., 100 mW-300 W, e.g., 1-10 mW, e.g., 2 mW, 3 mW, 4 mW, 5 mW, 6 mW, 7 mW, 8 mW, 9 mW, 10 mW, e.g., 10-100 mW, e.g., 20 mW, 30 mW, 40 mW, 50 mW, 60 mW, 70 mW, 80 mW, 90 mW, 100 mW, e.g., 100-1000 mW, e.g., 200 mW, 300 mW, 400 mW, 500 mW, 600 mW, 700 mW, 800 mW, 900 mW, 1 W, e.g., 1-10 W, e.g., 2 W, 3 W, 4 W, 5 W, 6 W, 7 W, 8 W, 9 W, 10 W, e.g., 10-100 W, e.g., 20 W, 30 W, 40 W, 50 W, 60 W, 70 W, 80 W, 90 W, 100 W, e.g., 100-1000 W, e.g., 200 W, 300 W, 400 W, 500 W, 600 W, 700 W, 800 W, 900 W, 1000 W). The energy is sufficient to power a component or sensor of the device (e.g., one or more of the sensors, an RF energy transmitter, or laser). The RF transmitter may operate at a frequency of 1 kHz to 100 MHz (e.g., 1 kHz to 50 MHz, e.g., 1-10 kHz, e.g., 1 kHz, 2 kHz, 3 kHz, 4 kHz, 5 kHz, 6 kHz, 7 kHz, 8 kHz, 9 kHz, 10 kHz, 10-100 kHz, e.g., 20 kHz, 30 kHz, 40 kHz, 50 kHz, 60 kHz, 70 kHz, 80 kHz, 90 kHz, 100 kHz, e.g., 100-1 MHz, e.g., 200 kHz, 300 kHz, 400 kHz, 500 kHz, 600 kHz, 700 kHz, 800 kHz, 900 kHz, 1 MHz, e.g., 1-10 MHz, e.g., 2 MHz, 3 MHz, 4 MHz, 5 MHz, 6 MHz, 7 MHz, 8 MHz, 9 MHz, 10 MHz, e.g., 10-100 MHz, e.g., 20 MHz, 30 MHz, 40 MHz, 50 MHz, 60 MHz, 70 MHz, 80 MHz, 90 MHz, 100 MHz).

The intravaginal device may be configured such that the sum of the vaginal angle and fornix angle ranges from about 30° to about 120°. The vaginal angle may be defined as an angle formed by a line drawn between the position of at least two of the sensors in the tether and the horizon. In some embodiments, the main body may comprise at least one (e.g., 2, 3, 4, and 5) pair of sensors anteriorly and one sensor posteriorly such that an angle formed by a line connecting the averaged location of the at least one (e.g., 2, 3, 4, and 5) pair of sensors anteriorly and the posterior sensor and by a line parallel to the horizon defines a fornix angle. In some embodiments the main body comprises at least four unpaired sensors, and the angle formed by the line connecting at least two of the sensors and a line parallel to the horizon defines the fornix angle.

The intravaginal device may be made from a flexible, biocompatible material (e.g., silicone, polyethylene, polypropylene, polystyrene, polyester, polycarbonate, polyvinyl chloride, polyethersulfone, polyacrylate, hydrogel, polysulfone, polyetheretherketone, thermoplastic elastomers, poly-p-xylylene, fluoropolymers, rubber, and latex).

The intravaginal device may be configured for use with a tool for insertion. The tool for insertion may be capable of deforming the intravaginal device and/or deploying the intravaginal device within the vagina of the individual so that the main body encircles the cervix or vaginal cuff and the tether extends from the posterior fornix in a caudal direction through the vagina.

In some embodiments of any of the above aspects, the tether may have one or more (e.g., 1, 2, 3, 4, 5, 6, 7, 8, 9, 10, 20, 30, 40, and 50) of the motion-detecting sensors. The main body may have one or more (e.g., 1, 2, 3, 4, 5, 6, 7, 8, 9, 10, 20, 30, 40, and 50) of the motion-detecting sensors. In some embodiments, the main body has two to ten of the motion-detecting sensors and the tether has five of the motion-detecting sensors. One of the motion-detecting sensors may be shared by the main body and the tether. The intravaginal device may be used to detect a pelvic floor muscle movement (e.g., pelvic floor lift, pelvic floor relaxation, Valsalva maneuver, sustained pelvic floor lift, and serially repeated pelvic floor lift).

In some embodiments of any of the above aspects, the main body may have a complete or incomplete circular form (e.g., a horseshoe form) or it may have a cup-shaped form. The main body or tether may further have a microcontroller for receiving and storing data from the one or more sensors. The main body or tether may further comprise a wired transmitter and/or receiver for communicating (e.g., wirelessly) data to an electronic device (e.g., computer, tablet, smartphone, and smart watch). The intravaginal device may be configured to send data to and receive data from the electronic device. The transmitter and/or receiver may be configured for use with a Bluetooth and/or Wi-Fi enabled electronic device. The transmitter and/or receiver may be located in an external housing connected to the intravaginal device by a detachable cable, which may be configured to assist in the removal of the intravaginal device. The electronic device may comprise a display (e.g., graphical user interface and/or a touch user interface). The RF transmitter, laser, and/or other sensors may be controllable via Bluetooth or Wi-Fi.

In some embodiments of any of the above aspects, the intravaginal device may comprise a power source (e.g., battery) connected to the one or more sensors. The sensors may be one or more of an accelerometer (e.g., multiple-axis accelerometer), gyroscope (e.g., multiple-axis gyroscope), micro-electro-mechanical systems (MEMS) sensor, G-sensor, tilt sensor, rotation sensor, a light detecting sensor, such as a light detecting and ranging (LiDAR) sensor, and/or an electrical impedance myography (EIM) sensor (e.g., localized biological transfer impedance (LBTI) sensor). The intravaginal device may comprise a combination of sensors of differing types and/or may further comprise at least one additional sensor within the main body selected from the group consisting of a pressure sensor, a muscle quality sensor, a muscle strength sensor, a pH sensor, a humidity sensor, a temperature sensor, a hormone sensor, and a toxin sensor.

In some embodiments, the length of the tether is about 3 cm to about 50 cm (e.g., 5, 10, 15, 20, 25, 30, 35, 40, 45, and 50 cm, e.g., 25.5 cm). In some embodiments, the circumference of the main body is about 10 cm to about 50 cm (e.g., 10, 15, 20, 25, 30, 35, 40, 45, and 50 cm, e.g., 27 cm). In certain specific embodiments, the intravaginal device comprises two or more (e.g., 3, 4, 5, 6, 7, 8, 9, and 10) sensors on the tether that are separated on the tether by a distance of about 0.5 cm to about 5 cm (e.g., 1, 1.5, 2, 2.5, 3, 3.5, 4, 4.5, and 5, e.g., 1.6 cm).

In another aspect, the invention features a system comprising the intravaginal device of any of the above aspects of the invention and a graphical user interface. The graphical user interface may be tethered wirelessly to the intravaginal device. The system may further comprise a transmitter and receiver, a detachable cable, a tool for insertion of the intravaginal device, an electronic device, and/or a database. The system may be used for treating or reducing the progression of a pelvic floor disorder (e.g., urinary incontinence, stress urinary incontinence, urge incontinence, mixed stress and urge urinary incontinence, anal or fecal incontinence, coital incontinence, pelvic organ prolapse, pelvic pain, sexual dysfunction, weak or impaired pelvic floor muscle function, post-labor issues or damage, pain and/or incontinence caused by damage to a lumbosacral nerve, muscle pain, nonrelaxing pelvic floor dysfunction, vaginismus, urethral hypermobility, cystocele, rectocele, and enterocele) in a subject.

In another aspect, the invention features a method of diagnosing a pelvic floor disorder, by inserting the intravaginal device of any one of the above aspects into a subject's (e.g., human) vagina and monitoring contraction of, or relaxation of, a pelvic floor muscle by detecting motion of the one or more sensors.

In another aspect, the invention features a method of treating, inhibiting, or reducing the development or progression of a pelvic floor or vaginal disorder in a subject by inserting the intravaginal device of any of the above aspects into a subject's (e.g., a human's) vagina and monitoring the contraction of, or relaxation of, a pelvic floor muscle by detecting position or motion of the one or more sensors, in which the treatment reduces the frequency of occurrence and/or severity of at least one symptom (e.g., muscle tone, muscle strength, bladder leakage, anal or fecal leakage, pain, frequency, skin laxity, and urgency) of a pelvic floor or vaginal disorder.

In another aspect, the invention features a method of treating, inhibiting, or reducing the development or progression of, a pelvic floor or vaginal disorder in a subject, the method by inserting the intravaginal device of any of the above aspects into a subject's vagina and transmitting energy from the one or more energy transmitters, wherein the treatment reduces the frequency of occurrence and/or severity of at least one symptom (e.g., muscle tone, muscle strength, bladder leakage, anal or fecal leakage, pain, frequency, skin laxity, and urgency) of a pelvic floor or vaginal disorder. Exemplary vaginal disorders are vaginal laxity, pelvic organ prolapse, incontinence, tissue tone (e.g., moisture and tightness), nerve sensitivity, orgasmic dysfunction, vulvovaginal laxity (e.g., in labial and vaginal tissues), atrophic vaginitis, stress incontinence, and pubocervical fascia tightening. The one or more energy transmitters may be radio frequency transmitters, which are used to heat vaginal tissue. The method may be performed for 1-30 minutes (e.g., 10, 15, 20, or 25 minutes) or more per session. The sessions may be repeated one or more times per for one or more days (e.g., 1 week, 1 month, 6 months, 1 year, or more). The intravaginal device may be recharged after a use or several uses. The energy transmitters may transmit energy (e.g., 1 mW-500 W, e.g., 100 mW-300 W, e.g., 1-10 mW, e.g., 2 mW, 3 mW, 4 mW, 5 mW, 6 mW, 7 mW, 8 mW, 9 mW, 10 mW, e.g., 10-100 mW, e.g., 20 mW, 30 mW, 40 mW, 50 mW, 60 mW, 70 mW, 80 mW, 90 mW, 100 mW, e.g., 100-1000 mW, e.g., 200 mW, 300 mW, 400 mW, 500 mW, 600 mW, 700 mW, 800 mW, 900 mW, 1 W, e.g., 1-10 W, e.g., 2 W, 3 W, 4 W, 5 W, 6 W, 7 W, 8 W, 9 W, 10 W, e.g., 10-100 W, e.g., 20 W, 30 W, 40 W, 50 W, 60 W, 70 W, 80 W, 90 W, 100 W, e.g., 100-1000 W, e.g., 200 W, 300 W, 400 W, 500 W, 600 W, 700 W, 800 W, 900 W, or 1000 W), e.g., in units of energy per area (e.g., 1 mm$^2$ to 10 cm$^2$, e.g., 1-10 mm$^2$, 10-100 mm$^2$, or 1-10 cm$^2$) and, e.g., for a set amount of time (e.g., 10 seconds-30 minutes or more, e.g., 30 seconds, 1 minute, 10 minutes, 20 minutes, or 30 minutes). The energy may also be transmitted to a certain depth within the tissue (e.g., 0.1 mm-10 cm, e.g., 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 1 cm, 2 cm, 3 cm, 4 cm, 5 cm, 6 cm, 7 cm, 8 cm, 9 cm, 10 cm).

The subject may be standing or lying down during performance of the methods of the above aspects.

Any of the above methods may include measuring a vaginal angle formed by a line between a position of at least two of the sensors in the tether and a line parallel to a horizon. In some embodiments, the method involves using an intravaginal device with a tether having eight of the motion-detecting sensors, and in which the vaginal angle is formed by a line between the position of at least two of the sensors in the tether and a line parallel to the horizon. The vaginal angle may be measured during PFR, Valsalva maneuver, and/or PFL. The method may comprise determining whether the vaginal angle increases above or decreases below a predetermined threshold (e.g., a vaginal angle determined at rest or in the subject at a prior time). The method may include diagnosing the subject with a pelvic floor disorder when the vaginal angle increases above or decreases below a predetermined threshold during a pelvic floor movement.

The method may include measuring a fornix angle by detecting a position of at least two of the one or more sensors in the main body, wherein an angle formed by a line connecting an averaged location of each pair of the sensors in the anterior and mid-main body and a line parallel to the horizon defines a fornix angle. In some embodiments, the main body has five of motion-detecting sensors and an angle formed by the line connecting an averaged location of two pairs of sensors (e.g., a pair of sensors in the anterior main body and a pair of sensors in the mid-main body) and a line parallel to the horizon defines a fornix angle. The method may include measuring the fornix angle during PFR, Valsalva maneuver, and/or PFL.

In some embodiments of any of the above methods, the tether has at least three of the motion-detecting sensors, and a level of curvature of a spatial orientation of the at least three sensors increases above or decreases below a predetermined threshold. The method may comprise diagnosing the subject with a pelvic floor disorder when the level of curvature increases above or decreases below a predetermined threshold (e.g., a level of curvature determined in the subject at rest or in the subject at a prior time).

The method may further comprise displaying a graphical representation of the position of the one or more sensors and/or the device on a graphical user interface. The vaginal angle or fornix angle may be displayed on the graphical user interface.

The method may further comprise measuring a performance metric (e.g., execution of PFL or PFR) as measured by the one or more sensors. The performance metric may be a duration of time during which the intravaginal device is in use. The performance metric may be selected from a measurement of pressure, muscle quality, muscle strength, humidity, temperature, a hormone level, a toxin level, and/or pH. The pelvic floor disorder may be urinary incontinence, stress urinary incontinence, urge incontinence, mixed stress and urge urinary incontinence, anal or fecal incontinence, coital incontinence, pelvic organ prolapse, pelvic pain, sexual dysfunction, weak or impaired pelvic floor muscle function, post-labor disorder or damage, pain and/or incontinence caused by damage to a lumbosacral nerve, muscle pain, nonrelaxing pelvic floor dysfunction, vaginismus, urethral hypermobility, cystocele, rectocele, and/or enterocele.

In some embodiments of any of the above aspects, the inner diameter of the main body of the intravaginal device is positioned around the cervix or vaginal cuff and the external diameter of the main body is positioned in the vaginal fornix. The one or more sensors on the tether may be located approximately halfway between an introitus of the vagina and the cervix, vaginal cuff, or vaginal fornix.

Definitions

As used herein, the singular form "a," "an," and "the" includes plural references unless indicated otherwise.

As used herein, the terms "about" and "approximately" mean +/−10% of the recited value.

As used herein, "administering" is meant a method of giving a dosage (e.g., a pharmaceutically effective dosage) of a pharmaceutical agent (e.g., a pharmaceutical agent useful in the treatment of a pelvic floor disorder (PFD) or a symptom thereof) to a subject. The pharmaceutical agents and compositions utilized in the methods described herein can be administered, e.g., by an intravaginal device of the invention. The intravaginal device may be configured to contain at least one pharmaceutical agent (e.g., 1, 2, 3, 4, 5, or more pharmaceutical agents). For example, the pharmaceutical agent may be uniformly dispersed or dissolved throughout a material (e.g., a polymeric material) of the intravaginal device, contained within a delivery module (e.g., an inner core or reservoir incorporated into the intravaginal device), and/or contained within a coating, layer, or gel applied to the surface of the intravaginal device. The amount of an agent administered by, e.g., an intravaginal device of the invention, can vary depending on various factors (e.g., the pharmaceutical agent or composition being administered and the severity of the PFD, or the symptom thereof, being treated). The intravaginal device can be configured to control the rate of pharmaceutical agent release (e.g., continuous release, periodic release, or release in response to, e.g., user input, a stimuli, and/or sensor data obtained by the intravaginal device) and/or to enable the delivery (e.g., simultaneous and/or consecutive delivery) of more than one pharmaceutical agent (e.g., 1, 2, 3, 4, 5, or more pharmaceutical agents).

As used herein, the phrase "approximately circumferentially surround a cervix or a vaginal cuff" refers to the form of an intravaginal device, such that the form is capable of encircling and/or cupping the cervix or vaginal cuff.

As used herein, the term "in proximity to" and "proximal" refers to a location near (e.g., about 0.01-5 mm from, or adjacent to, the tissue surface surrounding the cervix or vaginal cuff) the tissues of the vagina surrounding the cervix or vaginal cuff of a subject at which an intravaginal device of the invention is positioned during treatment (e.g., performance of pelvic floor lifts (PFLs) and/or pelvic floor relaxations (PLRs)).

As used herein, the term "biofeedback" refers to information that can be used to train an individual to change physiological activity (e.g., pelvic floor muscle function) for the purpose of improving health and performance (e.g., treating, reducing, and/or preventing the occurrence of or the symptoms of a pelvic floor disorder (PFD)). Biofeedback may also include information collected by an intravaginal device of the invention during daily monitoring, e.g., in substantially real-time, while a user performs her daily activities. The information can be reviewed substantially in real-time or can be accessed for review at a later time. Instruments, such as an intravaginal device of the invention can be used to measure physiological activity, such as muscle activity (e.g., movement and pressure), vaginal pressure, muscle quality, and vaginal canal pH, temperature, and humidity, and to provide this information as biofeedback to the individual. Instruments, such as an intravaginal device of the invention can also be used to measure the level of a molecule, e.g., the level of a hormone and/or the level of a toxin, and to provide this information as biofeedback to the individual. The presentation of this information to the individual can be by a visual, audible, or tactile signal, and can support a desired physiological change (e.g., improved pelvic floor muscle strength, control, and quality).

As used herein, the term "biocompatible material" refers to materials that are not harmful or toxic to living tissues.

As used herein, the term "calibration period" refers to the process of determining a baseline set of measurements from the sensors positioned within the intravaginal device during a period of use of the intravaginal device by an individual, such that the baseline set of measurements characterize the health (e.g., strength, muscle quality, condition) of the individual's pelvic floor muscles prior to or at the start of a treatment program. The baseline set of measurements collected during the calibration period can be used to calculate and/or determine the progress of an individual through a treatment program.

As used herein, the term "continence" is defined as the ability to refrain from or to retain a bodily discharge (e.g., urination, defecation, or passage of flatus).

As used herein, the term "detection" means the action or process of identifying information, e.g., the activation and/or the relaxation of a pelvic floor muscle. Detection can occur from a direct or indirect source (e.g., a sensor).

As used herein, "delaying progression" of a disorder or disease means to defer, hinder, slow, retard, stabilize, and/or postpone development of the disease or disorder (e.g., a pelvic floor disorder (PFD)). This delay can be of varying lengths of time, depending on the history of the disease and/or individual being treated. As is evident to one skilled in the art, a sufficient or significant delay can, in effect, encompass prevention, in that the individual does not develop the disease or disorder. For example, a PFD after vaginal childbirth may be delayed and/or prevented.

As used herein, the term "diagnosis" refers to the identification or classification of a disease or condition (e.g., a pelvic floor disorder). For example, "diagnosis" may refer to identification of a particular type of PFD.

A "disorder" is any condition that would benefit from treatment including, but not limited to, chronic and acute disorders or diseases including those pathological conditions which predispose the subject to the disorder in question.

As used herein, the term "monitoring" refers to a use of an intravaginal device of the invention to collect, track, and/or store data, e.g., data obtained from sensor(s) of the intravaginal device, as described herein. The monitoring occurs, e.g., when the intravaginal device is positioned within the vaginal cavity of a user and/or when the intravaginal device is used during a treatment period (e.g., during the performance of a series of pelvic floor exercise (e.g., a pelvic floor lift and/or relaxation)). The monitoring may also occur, e.g., substantially in real-time while a user performs her daily activities. This feature allows the user, effectively in real-time, to alter activities or behaviors that cause pelvic floor damage or to continue activities or behaviors that improve pelvic floor health. Alternatively, data stored by the device during monitoring can be accessed by the user at a later time (e.g., 30 minutes, 1 hour, 2 hours, 3 hours, 4 hours, 5 hours, 6 hours, 12 hours, 24 hours, or more after activities monitored by the device) for analysis of whether the activity or behavior had a positive or negative effect on pelvic floor health. The process of monitoring can include obtaining sensor data (e.g., measurements) that can be used to describe an individual's pelvic floor muscle movement, pressure, strength, and/or quality. Additionally, vaginal conditions including, but not limited to, shape, size, temperature, pH, and/or moisture level may also be monitored by an intravaginal device of the invention. An intravaginal device of the invention may also be configured to detect the level of a molecule, e.g., the level of a hormone and/or the level of a toxin.

As used herein, the terms "pelvic floor lift" and "PFL" refers to a movement of the pelvic floor (e.g., the muscle fibers of the levator ani (e.g., the pubococcygeus, ileococcygeus, coccygeus, and puborectalis muscles) and the associated connective tissues which span the area in a spherical form from the pubic bone anteriorly to the sacrum posteriorly and to the adjoining bony structure joining these two bones, which is characterized by an upward movement (e.g., a lifting movement, such as a movement in the cranial direction) of the pelvic floor. The movement of the pelvic floor during the performance of a PFL is a distinctly-described component of the collective action of the entire pelvic floor (e.g., the levator ani, urethral and anal sphincters, bulbocavernosus, ischiocavernosus, superficial tranverse perineal muscles) whereby the combined lifting and circumferentially-directed squeezing action is produced when all muscles are activated simultaneously. A PFL is a type of pelvic floor muscle training (PFMT) exercise that selectively targets the levator ani component of the pelvic floor.

As used herein, the terms "pelvic floor relaxation" and "PFR" refers to a movement of the pelvic floor (e.g., the muscle fibers of the levator ani (e.g., the pubococcygeus, ileococcygeus, coccygeus, and puborectalis muscles) and the associated connective tissues which span the area in a spherical form from the pubic bone anteriorly to the sacrum posteriorly and to the adjoining bony structure joining these two bones), which is characterized by a relaxation (e.g., a downward movement, such as a movement in the caudal direction) of the pelvic floor. The movement of the pelvic floor during the performance of a PFR is distinct from the concentric contraction (e.g., shortening contraction) of the PFL, and represents the lengthening or relaxation of the muscle fibers. A PFR is a type of PFMT exercise.

As used herein, the term "pharmaceutically acceptable" as applied to a pharmaceutical agent, such as a compound, material, composition and/or dosage form, means that the agent is suitable for contact with vaginal tissues of an individual, e.g., without causing excessive toxicity, irritation, allergic response, or other complications. A determination of "pharmaceutically acceptable" can be made using, e.g., industry-recognized and/or Food and Drug Administration (FDA)-recognized standards.

By "pharmaceutically acceptable diluent, excipient, carrier, or adjuvant" is meant a diluent, excipient, carrier, or adjuvant that is physiologically acceptable to a subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art and described, for example, in Remington's Pharmaceutical Sciences (18th edition, A. Gennaro, 1990, Mack Publishing Company, Easton, PA), incorporated herein by reference.

As used herein, the term "pharmaceutical composition" refers to a medicinal or pharmaceutical formulation or adjuvant that contains an active ingredient (e.g., a pharmaceutical agent) and may contain one or more excipients, carriers, or diluents. The pharmaceutical composition may include a pharmaceutically acceptable component that is compatible with intravaginal delivery, e.g., by an intravaginal device of the invention. The pharmaceutical composition may be, e.g., in solid or liquid form. To facilitate controlled-release from an intravaginal device of the invention, a pharmaceutical composition may also be formulated to be, e.g., time-released and/or to release upon exposure to an environmental condition, such as a pre-determined temperature, moisture level, and/or pH. Exposure to such an environmental condition may, e.g., dissolve a drug-impervious coating around the pharmaceutical agent and/or increase the solubility of the pharmaceutical agent in vaginal fluid.

As used herein, the term "pharmaceutically effective," refers to an amount of a pharmaceutical agent that is sufficient to produce a desired physiological or pharmacological change in a subject. This amount may vary depending upon such factors as the potency of the particular pharmaceutical agent, the desired physiological or pharmacological effect, and the time span of the intended treatment. Those skilled in the pharmaceutical arts will be able to determine the pharmaceutically effective amount for any given pharmaceutical agent in accordance with standard procedures.

As used herein, "real-time" refers to the actual time during which an event, such as a daily activity, occurs.

As used herein, "sensor data" refers to measurements (e.g., any one or more of measurements of pelvic floor muscle movement, pelvic floor muscle quality, pelvic floor muscle strength, pressure, and measurements of other vaginal conditions, such as pH, temperature, and/or moisture), which characterize an individual's pelvic floor health and are obtained by a sensor(s), as described herein, of an intravaginal device of the invention. Sensor data may also be collected that characterize the level of a molecule, e.g., the level of a hormone and/or the level of a toxin.

As used herein, "radio frequency" refers to electromagnetic waves that have a frequency in the range from $10^3$ Hz to $10^{12}$ Hz.

As used herein, a "subject," "patient," or "individual" is a human, in particular, a female.

As used herein, the terms "reducing" and "inhibiting" are defined as the ability to cause an overall decrease of about 10%, 20%, 30%, 40%, 50%, 60%, 70%, 75%, 80%, 85%, 90%, 95%, or more. Reduce or inhibit can refer, for example, to the symptoms of the pelvic floor disorder (PFD) being treated.

As used herein, the term "transdermal delivery" refers to a route of administration, e.g., of a pharmaceutical agent or composition useful in the treatment of a PFD, or a symptom thereof, across the skin for, e.g., systemic distribution.

As used herein, the term "transmucosal delivery" refers to a route of administration, e.g., of a pharmaceutical agent or composition useful in the treatment of a PFD, or the symptoms thereof, involving diffusion through a mucous membrane, e.g., the tissues of the vagina.

As used herein, the term "treating" refers to performing pelvic floor lifts (PFLs) and/or pelvic floor relaxations (PFRs) in a subject in need thereof for therapeutic purposes (e.g., to treat or reduce the likelihood of developing a PFD), in particular in conjunction with the use of a device or method described herein. To "treat disease" or use for "therapeutic treatment" includes administering treatment to a subject already suffering from a disease to improve or stabilize the subject's condition. To "prevent" or "reduce likelihood of developing" disease refers to prophylactic treatment of a subject who is not yet ill or symptomatic, but who is susceptible to, or otherwise at risk of, a particular disease, such as a PFD.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "female urogenital system" or "urogenital system" refers to the organ system of the female reproductive system, which includes, e.g., the Bartholin's glands, cervix, clitoris, clitoral frenulum, clitoral glans (glans clitoridis), clitoral hood, fallopian tubes, labia, labia majora, labia minora, frenulum of labia minora, ovaries, skene's gland, uterus, vagina, and vulva; the urinary system, which includes, e.g., the kidneys, ureters, bladder, and the urethra; and the surrounding and supporting nerves and musculature.

As used herein, "vaginal cuff" refers to the sutured tissue at the top of the vaginal canal remaining after removal of the cervix (e.g., during a hysterectomy).

As used herein, "pelvic organ prolapse" or "POP" refers to the descent of one or more aspects of the vagina and uterus, such as the anterior vaginal wall, posterior vaginal wall, the uterus (cervix), or the apex of the vagina (vaginal vault or cuff scar after hysterectomy). This descent allows nearby organs to herniate into the vaginal space, which is commonly referred to as cystocele, rectocele, or enterocele. Pelvic organ prolapse may be asymptomatic or associated with one or more symptoms, such as, e.g., pressure with or without a bulge, sexual dysfunction, and disruption of normal lower urinary tract or bowel function. Pelvic organ prolapse can be defined using patient-reported symptoms or physical examination findings (e.g., vaginal bulge protruding to or beyond the hymen). Most women feel symptoms of POP when the leading edge reaches 0.5 cm distal to the hymenal ring. As used herein, "urinary incontinence" refers to the leaking of urine from the bladder. Incontinence can range from leaking just a few drops of urine to complete emptying of the bladder. Urinary incontinence can be divided into three main types: stress urinary incontinence (SUI), urgency urinary incontinence, and mixed incontinence. Stress urinary incontinence is leaking urine when coughing, laughing, or sneezing. Leaks can also happen when a woman walks, runs, or exercises. Urgency urinary incontinence is a sudden strong urge to urinate that is hard to stop. Women with this type of urinary incontinence may leak urine on the way to the bathroom. Mixed incontinence combines symptoms of both stress and urgency urinary incontinence.

As used herein, "pelvic floor" refers to the muscular area at the base of the abdomen attached to the pelvis.

As used herein, "pelvic floor disorders" or "PFDs" refers to disorders affecting the muscles and tissues that support the pelvic organs. These disorders may result in loss of control of the bladder or bowels or may cause one or more pelvic organs to drop downward, resulting in prolapse.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a schematic drawing showing intravaginal device 100 with main body 110 and tether 10. Main body 110 contains 5 sensors 200 (e.g., accelerometers, such as MEMS sensors) and tether 10 contains 8 sensors 200. One sensor 200 is shared by both main body 110 and tether 10.

FIGS. 4A-4D are schematic drawings showing a vaginal angle ($\theta_V$) and a fornix angle ($\theta_F$) referenced relative to intravaginal device 100 (e.g., when inserted into a vaginal canal of a subject). When positioned in a vaginal canal of a subject, sensor pair 1 of intravaginal device 100 shown in FIG. 4A would reside in the anterior fornix, while the sensors of sensor pair 2 each would reside in a lateral fornix. A single remaining sensor, sensor 3, would reside in the posterior fornix, this last being also part of the tether. FIG. 4B shows the anterior fornix sensors, labeled A9 and A12, the sensors in the lateral fornices, labeled A10 and A11, and the single posterior fornix sensor, labeled A8, which is shared by main body 110 and tether 10. Sensors exclusively on tether 10 are labeled A1-A7. The vaginal angle ($\theta_V$) is defined as the angle between the line of the tether (essentially demarcating the long axis of the vagina) and the line contained in a plane parallel to the virtual plane of the introitus, hereafter designated the "horizon." The fornix angle ($\theta_F$) is defined as the angle between the line connecting the anterior and posterior fornices (the anterior and posterior points of the main body) and the line of the horizon. FIG. 4C shows (1) that each sensor of the tether may be connected by a best-fit line and (2) the positions of the two sensors in the anterior fornix may be averaged; similarly, the positions of the sensors in the lateral fornices may be averaged, and a best fit line may be drawn from the posterior fornix to the anterior fornix. The vaginal angle ($\theta_V$) and fornix angle ($\theta_F$) are shown in both FIGS. 4C and 4D. In FIG. 4D, the points ("nodes") shown in FIG. 4C are labeled S1-S10. The sensors depicted are, e.g., accelerometers, such as MEMS sensors.

FIG. 6B is a data set showing the vaginal length of ten subjects, including mean, standard deviation, and range. The vaginal length is calculated by determining the length of the tether that resides within the vaginal canal.

FIG. 8A shows the vaginal angle during pelvic floor relaxation. FIG. 8B shows the vaginal angle during Valsalva maneuver (bearing down). FIG. 8C shows the vaginal angle during pelvic floor lift. The sensor data were generated using MEMS sensors.

FIG. 20A is a graph showing the sensor angle for sensors S9 and S10 versus time in subject 006. Subject 006 performed pelvic muscle relaxation ("R"), Valsalva maneuver ("V"), and pelvic floor lift ("L"). The sensor data were generated using MEMS sensors.

FIGS. 20B-20D are panel images showing the position of all sensors S1-10 (top) and the fornix sensors S9-10 (bottom), during pelvic floor relaxation (FIG. 20B), a Valsalva maneuver (FIG. 20C), and during a pelvic floor lift maneuver (FIG. 20D), respectively. The graphs of S9-10 show that data produced with the fornix sensors alone are less robust than data produced with the tether sensors (S1-S8). The sensor data were generated using MEMS sensors.

FIG. 21 is a schematic drawing showing intravaginal device 100 with main body 110 and tether 10. Inset on the left shows a close-up view of battery 800 and circuit board 700. Inset on the right shows a gradated ruler on tether 10 that allows a user to determine the depth of insertion of intravaginal device 100.

FIGS. 22A-22D are schematics showing four different perspective views of intravaginal device 100 with main body 110, tether 10, circuit board 700, and battery 800. Circuit board 700 has a width of about 2.3 cm (FIGS. 22A-22B), tether 10 has a length of about 24.7 cm (FIG. 22C) and main body ring 110 has a diameter of about 5.4 cm (FIG. 22D).

FIG. 23 is a schematic showing intravaginal device 100 with main body 110, tether 10, circuit board 700, and battery 800. Intravaginal device 100 contains MEMS accelerometers and RF energy transmitters positioned around main body 110 and along the length of tether 10.

FIG. 24 is a schematic showing intravaginal device 100 with main body 110, tether 10, circuit board 700, and battery 800. Intravaginal device 100 contains MEMS accelerometers, pressure sensors, and electrical stimulator electrodes positioned around main body 110 and along the length of tether 10.

DETAILED DESCRIPTION OF THE INVENTION

Figure 1:
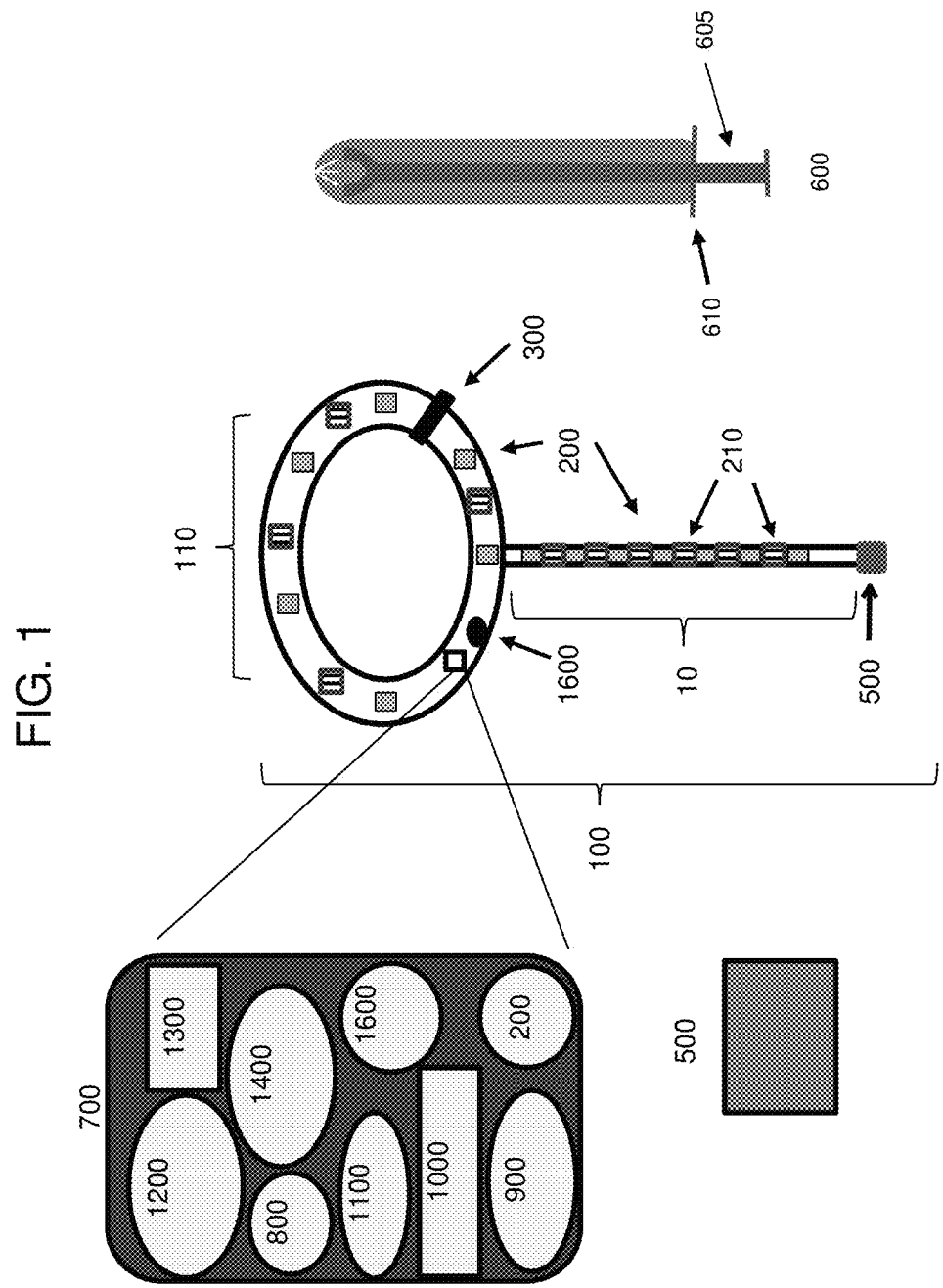
FIG. 1 is a schematic drawing showing an intravaginal device 100 that has a main body 110 (which may have, e.g., a ring form or an incomplete ring form), insertion tool 600 (applicator and tool for removal), tether 10, and transmitter/receiver box 500. Tether 10 may be non-detachable from main body 110 or, if detachable from main body 110, is configured for easy removal. Intravaginal device 100 contains circuit board 700, either in main body 110 or tether 10, which connects sensor(s) 200 (e.g., accelerometers, such as MEMS sensors), battery 800, microcontroller 900, internal transmitter/receiver 1000, data storage component 1100, sensory output component 1200, wireless communication antennae 1300, authentication chip 1400 (e.g., an Apple product authentication chip), and ON/OFF switch 1600. Intravaginal device 100 may also contain molded wing 300 for the reduction of rotation and slippage of the device within the vaginal canal of the individual. Intravaginal device 100 may also contain energy transmitters 210 (shown as hatched boxes) either on main body 110 or ring 10. Insertion tool 600 may also include plunger 605, e.g., for insertion in the vagina, and tab 610, which can be used to hold applicator 600 in place as intravaginal device 100 is removed. Any of the above components may or may not be present on intravaginal device 100 (e.g., energy transmitters 210, such as RF transmitters are optional).

The invention features devices, systems, and methods for training the pelvic floor muscles of an individual (e.g., a female patient), thereby treating or reducing the likelihood of developing a PFD, or for treating a vaginal disorder, in particular, using an intravaginal device. The intravaginal device described herein can be used to measure an individual's performance of a PFL and/or PFR using one or more sensors within the device. The intravaginal device may be configured to provide monitoring of the overall health status of a user's urogenital system and pelvic floor (e.g., the muscle fibers of the levator ani, e.g., the pubococcygeus, ileococcygeus, coccygeus, puborectalis muscles and associated connective tissues) in substantially real-time, e.g., while a user performs her daily activities. The device can also provide biofeedback to the individual following or during use. The device and system can be configured to coach the individual to perform a PFL and/or PFR correctly and to guide them to reach therapeutic goals, such as reduced PFD symptom occurrence and/or severity. Exemplary intravaginal devices, systems, and methods for training, visualizing, and diagnosing the health state of pelvic floor muscles of an individual have been extensively described in PCT Application No. PCT/US2017/044444, the disclosure of which is hereby incorporated in its entirety.

Various methods have been proposed to improve the strength and tone of the pelvic floor muscles, such as pelvic floor muscle training (PFMT), yet many of these methods do not target and activate the correct pelvic floor muscles. The devices, systems, and methods described herein can be used to train an individual to perform PFMT exercises characterized by either a lifting (e.g., upward) movement of the pelvic floor or a lowering (e.g., downward) movement of the PF, which are referred to herein as a pelvic floor lift (PFL) and a pelvic floor relaxation (PFR), respectively. Training a patient to perform a PFL and/or a PFR can lead to improvements in both the strength and the quality of the pelvic floor muscles, resulting in a therapeutic benefit for individuals having a PFD.

The intravaginal device may also be used to monitor (e.g., with one or more sensors as described herein) the overall health status of a user's urogenital system and pelvic floor (e.g., the muscle fibers of the levator ani (e.g., the pubococcygeus, ileococcygeus, coccygeus, puborectalis muscles and associated connective tissues) in substantially real-time, e.g., while a user performs her daily activities. For example, an intravaginal device of the invention may be configured to detect when a user performs a daily activity that alters (e.g., increases and/or decreases) the overall health of her urogenital system and/or pelvic floor and may provide feedback to the user, e.g., on how the detected activity affects her health status. A user may review the feedback in substantially real-time or they may review feedback at a later time of her choosing, e.g., by accessing feedback stored in the memory of the intravaginal device, in the memory of a local electronic device (e.g., a computer, phone, or tablet connected to the intravaginal device), and/or in the memory of a remote electronic device (e.g., a web-located and/or cloud-based database connected to the intravaginal device). Feedback may be presented as a summary, e.g., as one or more graphs, showing how a user's daily activities and detected vaginal conditions (e.g., pH, temperature, pressure, moisture level, muscle movement (e.g., a PFL and/or a PFR), muscle quality, muscle strength, and/or the level of a molecule, such as a hormone and/or toxin) affected the overall health status of a user's urogenital system and/o pelvic floor over time (e.g., over a period of time, such as a period of about 1 to about 60 minutes, about 1 to about 24-hours, about 1 to about 31 days, about 1 to about 24 months, or about 1 or more years). Daily monitoring, as described herein, may help a user to optimize treatment with an intravaginal device of the invention, to avoid the development and/or reoccurrence of a PFD, or the symptoms thereof, and/or to inform a user on the development and/or progression and/or treatment status of an additional condition or disorder of the female pelvic floor or urogenital tract.

The intravaginal device of the invention may be configured with one or more energy transmitters and used to administer energy to vaginal tissue, which may be used in therapeutic applications to treat a pelvic floor or vaginal disorder. Exemplary vaginal disorders are vaginal laxity, pelvic organ prolapse, incontinence, tissue tone (e.g., moisture and tightness), nerve sensitivity, orgasmic dysfunction, vulvovaginal laxity (e.g., in labial and vaginal tissues), atrophic vaginitis, stress incontinence, and pubocervical fascia tightening. The energy transmitters may be, for example, radio frequency transmitters, lasers, or electrical stimulators. RF transmitters provide nonablative radio frequency in the form of thermal energy to treat vaginal and pelvic floor disorders by heating tissue. By applying heat to the affected tissue, the thermal damage stimulates collagen production in deep layers of the skin and subcutaneous tissue to strengthen and fortify the collagen network in the vagina and surrounding area. This strengthens the tissues in areas critical for maintaining pelvic floor and vaginal health. The intravaginal device of the invention may be configured with or without this therapeutic capability.

Additionally, an intravaginal device of the invention may be configured to administer or deliver at least one (e.g., 1, 2, 3, 4, 5, or more) pharmaceutical agent, e.g., a pharmaceutical agent useful in the treatment of a PFD or a symptom thereof (e.g., to promote a change in muscle tone and/or muscle strength, or to reduce bladder leakage (including frequency and urgency of urination), anal or fecal leakage, or pain. The device may also be configured to treat an additional condition, disease, and/or related symptom present in an individual having a PFD, e.g., a condition, disease, or related symptom affecting a vaginal tissue and/or an organ or tissue of a female subject. Non-limiting examples of an additional condition, disease, or symptom that may be treated by an intravaginal device of the invention configured to deliver a pharmaceutical agent include a sexually transmitted disease (STD), a yeast infection (e.g., candida vulvovaginitis), a bacterial infection (e.g., bacterial vaginosis), a parasitic infection (e.g., trichomoniasis), an infection of the cervix (e.g., cervicitis), a cancer (e.g., vaginal, vulva, cervical, ovarian, endometrial, and/or fallopian tube cancer), vaginitis (e.g., infectious and/or noninfectious vaginitis), endometriosis, vaginal pain, vulvar pain (e.g., vulvodynia), a vulvar or vaginal injury, pudendal neuralgia, and/or a vaginal skin condition (e.g., vaginal dermatitis). An intravaginal device configured to deliver a pharmaceutical agent, may be formed from biocompatible polymers and contain a pharmaceutical agent released, e.g., by diffusion through the polymer matrix. In some instances, the pharmaceutical agent may be uniformly dispersed or dissolved throughout the polymer matrix (e.g., of the main body and/or tether of an intravaginal device of the invention) in a design configuration that is referred to in the art as a "monolithic system." In some instances, the drug may be confined to an inner core within the main body and/or tether of an intravaginal device of the invention in a design configuration that is referred to in the art as a "reservoir system."

An intravaginal device of the invention configured to deliver a pharmaceutical agent may be inserted into the vaginal cavity and the pharmaceutical agent may be absorbed by the surrounding body fluid through the vaginal tissue, e.g., over a treatment period. Intravaginal devices of the invention configured as monolithic systems may exhibit, e.g., Fickian diffusion-controlled pharmaceutical agent release, whereby the release rate decreases with time. Intravaginal devices of the invention configured to contain a reservoir system may exhibit a zero order release of a pharmaceutical agent.

Use of an intravaginal device of the invention that is configured to deliver a pharmaceutical agent may result in an enhanced therapeutic benefit for an individual having a PFD when combined with pelvic floor training (e.g., the performance of a PFL and/or PFR), e.g., as compared to the therapeutic benefit achieved through use of an intravaginal device to perform pelvic floor exercises that is not configured to deliver a pharmaceutical agent). Monitoring the overall health status of a user's urogenital system and/or pelvic floor (e.g., the muscle fibers of the levator ani, e.g., the pubococcygeus, ileococcygeus, coccygeus, puborectalis muscles and associated connective tissues), with the option of receiving instantaneous (e.g., substantially real-time) feedback, may help a user to optimize and/or enhance the efficiency of a treatment regime including a pharmaceutical agent (e.g., a pharmaceutical agent delivered by an intravaginal device of the invention or administered, e.g., by the user, in combination with the use of an intravaginal device of the invention). For example, an intravaginal device of the invention may be configured to identify a poor health status based on data collected from one or more sensors (e.g., 1, 2, 3, 4, 5, 6, 7, 8, 9, 10, or more sensors) of the intravaginal device that are configured to measure a metric, e.g., a muscle movement (e.g., a PFL and/or PFR), muscle strength, muscle quality, pressure, pH, temperature, biomolecule level (e.g., a hormones and/or a toxin), and/or moisture level (humidity) and to deliver a pharmaceutical agent automatically or to signal to the user the need or benefit of delivering the pharmaceutical agent.

I. Pelvic Floor Lifts (PFLs) and Pelvic Floor Relaxations (PFRs)

The pelvic floor (PF), also referred to as the pelvic floor diaphragm, is predominantly formed by the muscle fibers of the levator ani (e.g., the pubococcygeus, ileococcygeus, coccygeus, and puborectalis muscles) and the associated connective tissues which span the area underneath the pelvis (Bharucha. *Neurogastroenterol Motil.* 18:507-519, 2006). The pelvic floor lift (PFL) is an exercise characterized by an upward movement (e.g., a lifting movement, e.g., a movement in the cranial direction) of the pelvic floor. A closely related movement comprising a relaxation (e.g., a downward movement, e.g., a movement in the caudal direction) of the pelvic floor is a pelvic floor relaxation (PFR). The movement of the pelvic floor during the performance of a PFL and/or a PFR may be distinct from the movement of the pelvic floor during the performance of a Kegel exercise. The Kegel movement, developed by Dr. Arnold Kegel, may be described as a contraction of the vaginal channel diameter (e.g., a squeezing movement of the vaginal walls, e.g., a movement of the vaginal walls in the dorsal-ventral or anterior-posterior) direction). During a PFL and a PFR the pelvic floor may be described as raising and lowering, respectively, the vaginal canal. This raising or lowering of the vaginal canal during a PFL and PFR may be due to the lifting and relaxing of the pelvic floor muscles.

Training an individual to perform PFLs and/or PFRs can improve the strength and muscle quality of the pelvic floor resulting in therapeutic benefit to individuals having pelvic floor disorders (PFDs). Examples of pelvic floor disorders that can be treated, prevented, and/or ameliorated by training an individual to perform PFLs and/or PFRs are further described herein.

Proper performance (e.g., accurate execution) of a PFL and/or PFR can be used to prevent injury to the pelvic floor during pelvic floor muscle training (PFMT). An individual contracting the pelvic floor muscles, such as by improperly performing a Kegel movement, may strain, damage, or otherwise reduce the effectiveness of PFMT with PFLs and/or PFRs. In particular, patients that bear down can create strain that can promote further damage to the pelvic floor. Therefore, to achieve maximum therapeutic benefit and to increase the efficacy of PFMT with PFLs and/or PFRs an intravaginal device of the invention, configured to sense and provide feedback on the accurate performance of a PFL and/or PFR, can be used along with PFLs and/or PFRs training as a therapeutic or prophylactic treatment for a PFD (e.g., to reduce the occurrence and/or severity of at least one symptom of a PFD).

A PFL and/or PFR can be identified and measured by an intravaginal device of the invention, which places a sensor within the vaginal cavity of an individual, specifically at a location proximal to the cervix or vaginal cuff. The sensor positioned at a location proximal to the cervix or a vaginal cuff is configured to detect movement of the pelvic floor in the cranial-caudal direction (e.g., lifting and/or relaxation movements of the PF) to detect (e.g., to measure) the performance and quality of a PFL and/or PFR executed by an individual. In devices utilizing a tether, the main body may or may not have a sensor and is configured to position a sensor(s) in the tether within the vaginal canal for measurement of a PFL and/or PFR. The devices, which are described further herein, can be used to treat, prevent, and/or ameliorate at least one symptom of a PFD.

Monitoring the overall health status of a user's urogenital system and/or pelvic floor (e.g., the muscle fibers of the levator ani, e.g., the pubococcygeus, ileococcygeus, coccygeus, puborectalis muscles and associated connective tissues) in substantially real-time may allow for the identification of daily activities that may affect, e.g., negatively, the health status of the user. For example, an intravaginal device of the invention may be configured to identify a poor health status based on data collected from one or more sensors (e.g., 1, 2, 3, 4, 5, 6, 7, 8, 9, 10, or more sensors) of the intravaginal device that are configured to measure a metric, e.g., muscle movement (e.g., a PFL and/or PFR), muscle strength, muscle quality, pressure, pH, temperature, biomolecule level (e.g., a hormones and/or a toxin level), and/or humidity, and to signal to the user the need or benefit of ceasing performance of the detected activity. In some instances, a detected metric, e.g., a muscle movement, may be beneficial to the health status of a user and may increase the efficiency of the user's established training program. In this case, the device can be configured to convey to the user the benefit of continuing or repeating the activity or behavior that provided the detected metric.

In some instances, a detected metric, e.g., a muscle movement, may negatively affect the health status of a user and may reduce the efficiency of the user's established training program for a PFD. In this case, the device can be configured to convey to the user the negative effect of continuing or repeating the activity or behavior that provided the detected metric.

In some instances, a detected metric, e.g., a muscle movement, a level of or change in the level of muscle strength, muscle quality, a hormone, a toxin, pH, temperature, and/or humidity may be used to diagnose and/or predict the development of a PFD and/or an additional disease or condition, as described herein, according to known methods known in the art. The intravaginal device may also be configured to signal to the user and/or the medical practitioner overseeing the user's treatment the need or benefit of altering the training program to reduce the impact of a user's daily activities or behaviors that negatively affect her health status and/or to address a new PFD and/or disease or condition that has developed in the user.

II. System and Device for Training a User to Perform a Pelvic Floor Lift (PFL) and/or Pelvic Floor Relaxation (PFR)

The intravaginal device described herein, which has a main body and/or a tether, can be used as part of a training system for performing a pelvic floor lift (PFL) and/or pelvic floor relaxation (PFR). The device is inserted into an individual, such that the intravaginal device is positioned proximal to the cervix or vaginal cuff, and is configured to treat, inhibit, and/or reduce the development of or progression of a pelvic floor disorder (e.g., urinary incontinence (UI), stress urinary incontinence (SUI), urge incontinence, mixed stress and urge urinary incontinence, dysuria (e.g., painful urination), anal or fecal incontinence, pelvic organ prolapse (POP) (e.g., urethra (urethrocele), bladder (cystocele), or both (cystourethrocele), vaginal vault and cervix (vaginal vault prolapse), uterus (uterine prolapse), rectum (rectocele), sigmoid colon (sigmoidocele), and small bowel (enterocele)), pelvic pain, sexual dysfunction (e.g., coital incontinence, a sexual pain disorder, dyspareunia, vaginismus, and/or impaired sexual arousal), weak or impaired pelvic floor muscle function, post-labor issues or damage, pain and/or incontinence caused by damage to a lumbosacral nerve, and nonrelaxing pelvic floor dysfunction) in an individual when used according to the methods described herein.

The intravaginal device has a main body with an outer edge configured to contact all or a portion of the vaginal wall surrounding the cervix or vaginal cuff and has an internal diameter sized to approximately circumferentially surround a cervix or a vaginal cuff. The internal and external diameter of the intravaginal device may be approximately equivalent, with the difference in their length being attributable to the thickness of the material used to fabricate the intravaginal device. The internal and/or external diameter may be about 20 mm to about 80 mm (e.g., about 20, 25, 30, 35, 40, 45, 50, 55, 60, 65, 70, 75, or 80 mm) in length. In some instances, the internal diameter of the intravaginal device may be smaller than the external diameter. In some instances, the intravaginal device can be fabricated with a tether (e.g., a flexible cord or ribbon) that can be optionally attached, e.g., by a removable or permanent connection, to the main body of the intravaginal device. The tether can have a length of up to about 14 cm (e.g., 1, 2, 3, 4, 5, 6, 7, 8, 9, 10, 11, 12, 13, or 14 cm) and a width of about 1 to about 10 mm (e.g., 1, 2, 3, 4, 5, 6, 7, 8, 9, or 10 mm). Different form factors of the device include a ring (round or oval), a ring with a tether, and an incomplete ring (e.g., a horseshoe configuration).

The intravaginal device (e.g., main body and/or tether) can be made from a flexible, biocompatible material, such as a material selected from the group consisting of, but not limited to, silicone, polyethylene, polypropylene, polystyrene, polyester, polycarbonate, polyvinyl chloride, polyethersulfone, polyacrylate, hydrogel, polysulfone, polyetheretherketone, thermoplastic elastomers, poly-p-xylylene, fluoropolymers, rubber, and latex. The intravaginal device may be fabricated to be solid, hollow, and/or partially filled. Additionally, the intravaginal device may contain metal and/or plastic components, such as a core, ring, spring, and/or wire. The metal and/or plastic components may be used to provide additional tension (e.g., a pushing force) on the vaginal walls to maintain the position of the intravaginal device when inserted into an individual when incorporated into the main body of the intravaginal device. In some instances, the intravaginal device is fabricated out of silicone. However, other suitable materials may be used to fabricate the intravaginal device.

The main body of the intravaginal device may be cup-shaped and include an optional permeable or semi-permeable membrane, mesh, and/or perforated barrier in the central portion of the device (e.g., spanning the internal diameter). In other instances, the intravaginal device may be a sponge and may include a depression for cupping the cervix or vaginal cuff. In some instances, in which the intravaginal device has a donut shape, the intravaginal device may include an optional permeable or semi-permeable membrane, mesh, and/or perforated barrier. The barrier may extend across the internal diameter of the donut-shaped intravaginal device.

The outer edge of the main body of the intravaginal device may be configured to apply pressure, tension, adhesion, and/or suction to the vaginal wall to hold the position of the intravaginal device at a location proximal to the cervix or vaginal cuff of the individual. The pressure, tension, adhesion, and/or suction applied to the vaginal wall by the outer edge of the intravaginal device is of a sufficient strength to limit slippage, repositioning, or displacement of the intravaginal device from the vaginal canal of individual.

Additionally, the main body of the intravaginal device may include at least one (e.g., 1, 2, 3, 4, 5, 6, 7, 8, 9, 10, or more) feature for the purpose of stabilizing, orienting, and/or positioning the device within the body of the individual. The feature may be selected from the group consisting of a coating, a protrusion, and a texture. In some instances, the feature is a coating (e.g., a surface coating) containing one or more one (e.g., 1, 2, 3, 4, 5, 6, 7, 8, 9, 10, or more) biomaterials. In a particular instance, the coating may be provided, such as within a kit, in a sealed packet for the individual to apply to the intravaginal device prior to insertion. In some instances, the feature is a protrusion or a series of protrusions having the shape of a wing, sphere, bump, knob, raised lined, and/or raised dot. In some instances, the feature is a texture, such as a sticky, rough, grooved, or pitted surface texture. The main body may also include indicia (e.g., a protrusion, symbol, writing, or etching) identifying the cranial (e.g., top), caudal (e.g., bottom), anterior (e.g., front), posterior (e.g., back), right, and left sides of the intravaginal device. The intravaginal device should be positioned within the body of the individual such that the top side sits proximal to the top of the vaginal canal (e.g., proximal to the cervix or vagina cuff), and the anterior side faces the front of the body. Examples of features to aid in retention are a bulbous extrusion at the top or bottom of the device and a form having protruding arms. The retention features may be applied as in the devices shown or they can be applied as features to other devices described herein, The retention features may be useful for a device of the invention that is designed to remain inside a woman's vagina for an extended period of time (e.g., at least 10 minutes, 20 minutes, 30 minutes, 40 minutes, 50 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months).

The intravaginal device includes at least one (e.g., 1, 2, 3, 4, 5, 6, 7, 8, 9, 10, 20, or more) sensor within the main body (e.g., the substantially ring shaped form) and/or the tether that is configured to detect a muscle movement, e.g., a PFL and/or a PFR. In some instances, the sensor may be configured to detect a muscle movement, e.g., a PFL and/or a PFR, which is performed during a user's daily activities, in substantially real-time. Daily activities may be identified by the intravaginal device as either contributing positively or negatively to the overall health of a user's urogenital system and/or pelvic floor (e.g., the muscle fibers of the levator ani, e.g., the pubococcygeus, ileococcygeus, coccygeus, puborectalis muscles and associated connective tissues). In some instances, the at least one sensor (e.g., 1, 2, 3, 4, 5, 6, 7, 8, 9, 10, 20, or more sensors) may be selected from the group consisting of a movement sensor, an orientation sensor, an accelerometer, a gyroscope, a micro-electro-mechanical systems (MEMS) sensor, a G-sensor, a tilt sensor, a rotation sensor, a pressure sensor, a light detecting sensor, such as a LiDAR sensor, an EIM sensor, and combinations thereof. The device may also include a light generating component for use with the light detecting sensor, such as a LiDAR sensor. The device may also include an electrode for use with the EIM sensor. Additionally, the intravaginal device may include one or more sensors (e.g., 1, 2, 3, 4, 5, 6, 7, 8, 9, 10, 20, or more sensors) configured to detect, e.g., a level of or change in the level of muscle strength, muscle quality, a biomolecule (e.g., a hormone and/or a toxin), pH, temperature, and/or humidity.

In some instances, the sensors may be positioned in an arrangement similar to or in an arrangement different from those described in International Publication Nos. WO2015103629A1, WO2016067023A1, and WO2016042310A1; U.S. Publication Nos. US20150032030A1, US20140066813A1, US20150151122A1, US20150133832A1, US20160008664A1, and US20150196802A1; and U.S. Pat. Nos. 8,983,627, 7,955,241, 7,645,220, 7,628,744, 7,957, 794, 6,264,582, and 6,816,744, each of which is incorporated by reference herein. For example, two or more sensors, as described herein, may be placed around the longitudinal axis of the intravaginal device, e.g., in a circle or a spiral around the central-axis of the main body and/or tether of the intravaginal device, approximately at ±1°, 2°, 3°, 4°, 5°, 6°, 7°, 8°, 9°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, or 270° relative to each other. Alternatively, or additionally, two or more sensors, as described herein, may be placed approximately 0.001 mm, 0.01 mm, 0.1 mm, 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 125 mm, 150 mm, 175 mm, 200 mm, 225 mm, 250 mm, 275 mm, 300 mm, 325 mm, 350 mm, or more apart, e.g., along the circumference of the main body and/or along the length of the tether of the intravaginal device. In some instances, the two or more sensors, as described herein, may be placed along the central-axis of the main body and/or tether of the intravaginal device. In some instances, the two or more sensors, as described herein, may be placed such that they are not on the central-axis, e.g., such that they are offset from the central axis of the main body and/or tether of the intravaginal device. In particular instances, such as when sensors are positioned within the tether, the main body may not contain a sensor. In other instances, when sensors are positioned within the tether the main body may also contain at least one (e.g., 1, 2, 3, 4, 5, 6, 7, 8, 9, 10, 20, or more) sensor. The at least one sensor (e.g., 1, 2, 3, 4, 5, 6, 7, 8, 9, 10, 20, or more sensors) may be selected from the group consisting of a movement sensor, accelerometer, gyroscope, micro-electro-mechanical systems (MEMS) sensor, G-sensor, tilt sensor, rotation sensor, a light detecting sensor, such as a LiDAR sensor, an EIM sensor, and combinations thereof. The device may also include an electrode and/or a light generating component. In some instances, the sensor is an accelerometer, such as a multiple-axis accelerometer. In other instances, the sensor is a gyroscope, such as a multiple-axis gyroscope. In yet other instances, the sensor is a MEMS sensor. Additionally, the intravaginal device may further include at least one (e.g., 1, 2, 3, 4, 5, 6, 7, 8, 9, 10, 20, or more) additional sensor within the main body and/or the tether selected from the group consisting of a pressure sensor, a muscle quality sensor, a muscle strength sensor, a biomolecule sensor (e.g., a hormone sensor and/or a toxin sensor), a temperature sensor, a humidity sensor, and a pH sensor. A sensor(s) can be positioned on the surface of the intravaginal device (e.g., on the surface of the main body and/or tether), such that all or a portion of the sensor(s), makes direct contact with the tissues of the vaginal walls and/or cervix or vaginal cuff of an individual. In some instances, the sensor(s) can be positioned about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more below the exterior surface (e.g., the surface that makes direct contact with the tissues of the vaginal walls and/or cervix or vaginal cuff of an individual) of the intravaginal device (e.g., the main body and/or tether of the intravaginal device). In some instances, the sensor can be positioned such that about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more of the sensor protrudes from the exterior surface of the intravaginal device (e.g., the main body and/or tether of the intravaginal device). Alternatively, the sensors can be positioned within the intravaginal device (e.g., within the main body and/or tether), such that the sensor does not directly contact the vaginal walls and/or cervix or vaginal cuff of an individual, but are positioned to detect motion as the user conducts a PFL or PFR.

As the intravaginal device (e.g., the main body and/or tether) can be fabricated to be solid, hollow, or partially filled, a sensor that does not make direct contact with the vaginal walls/and or cervix or vaginal cuff of an individual may be positioned at a depth within the solid material from which the intravaginal device (e.g., the main body and/or tether) was fabricated or within a hollow space of the intravaginal device (e.g., main body and/or tether). The sensor(s) may be evenly or unevenly positioned at intervals on or within the intravaginal device. The sensors within the intravaginal device (e.g., within the main body and/or tether) may be positioned such that when the intravaginal device is inserted into a user the sensors face the ventral direction (e.g., anterior direction).

The tether can be up to about 14 cm (e.g., 1, 2, 3, 4, 5, 6, 7, 8, 9, 10, 11, 12, 13, or 14 cm) in length and may be divided along its length into segments contain sensors. Sensors can be positioned along the length of the tether at even or uneven intervals, e.g., at an interval of about 1 to about 140 mm (e.g., 1, 2, 3, 4, 5, 6, 7, 8, 9, 10, 20, 30, 40, 50, 60, 70, 80, 90, 100, 110, 120, 130, or 140 mm). The location of a sensor within the tether may be identified on the outside of the device by the presence of indicia (e.g., a protrusion, symbol, writing, and/or etching) on the surface of the tether. The tether may be designed to be trimmed, e.g., by cutting with scissors, so that an individual can reduce the tether to a comfortable length. The indicia indicating the location of a sensor can help guide the individual to avoid cutting a sensor.

The intravaginal device (e.g., main body (e.g., the substantially ring shaped form) and/or tether) further includes a microcontroller within the substantially ring shaped form that is configured for receiving data from the sensor(s). The microcontroller may also be configured, or can include a separate component, for non-transiently storing data from the sensor(s). The microcontroller maybe connected to the sensor(s), e.g., by a wire and/or a circuit board. The wire and circuit board may be flexible or rigid.

The intravaginal device can also include a transmitter and receiver within main body (e.g., the substantially ring shaped form) and/or tether form for communicating wirelessly or via a detachable cable with an electronic device (e.g., a handheld or portable device or a computer, such as a smartphone, tablet, or laptop). Alternatively, the transmitter and receiver may be located in an external housing and connected to the intravaginal device wirelessly or by a detachable cable. The transmitter and receiver can be connected directly or indirectly to the microcontroller, sensor(s), and/or circuit board. The transmitter and receiver can be configured for use with a Bluetooth and/or Wi-Fi enabled electronic device. Information collected by the sensor(s) may be communicated (e.g., downloaded, transferred) to the electronic device wirelessly by the transmitter and receiver and/or by using the detachable cable.

The electronic device may be a computer, tablet, and/or smartphone (e.g., an iPhone, an iPad, an iPod Touch, an Android-based system, a Microsoft Windows-based system, or other equivalent device). The electronic device can be connected wirelessly (e.g., through a Bluetooth and/or Wi-Fi connection) to the intravaginal device and/or by a detachable cable. The electronic device can be configured to receive and/or process data measured by the sensor(s) of the intravaginal device. Alternatively, the electronic device can be configured to communicate (e.g., through a wired or wireless connection, e.g., through a Bluetooth, Wi-Fi, and/or internet connection) with a database that contains data collected by the intravaginal device or with another system that receives and processes the data and conveys the information to the electronic device. Data collected by the intravaginal device, such as data collected by the sensor(s), may be stored non-transiently on the electronic device. The data may be transmitted (e.g., transmitted after a training period, substantially in real-time, and/or at least once daily upon activation by the user) to a database (e.g., a database stored on a different computer, such as a web-located and/or cloud-based database). The data may include a performance metric and/or scoring information, such as a score assigned to a muscle movement, e.g., a PFL and/or PFR, performed by the individual that is reflective of the quality of the muscle movement, e.g., a PFL and/or PFR, performed as compared to a calibrated baseline from the individual. The data may include one or more, or all, of the highest and lowest scores achieved by an individual over a training period, an average score achieved by an individual over a training period, the length of time over which a particular score was maintained by an individual, the raw data collected from the sensor(s), the start time of and the length of the training period, maximum PFL and/or PFR duration, the current pH, the average, lowest, and highest pH reached by an individual over the training period, a score related to muscle quality.

Additionally, the data may include a performance metric and/or scoring information, such as a score assigned to the overall health status of a user's urogenital system and/or pelvic floor (e.g., the muscle fibers of the levator ani, e.g., the pubococcygeus, ileococcygeus, coccygeus, puborectalis muscles and associated connective tissues). The health status score may be derived from data collected, e.g., from an intravaginal device of the invention configured to monitor a user's urogenital system and/or pelvic floor in substantially real-time, which is an optional monitoring state ("Live Mode"), as a user performs her daily activities, e.g., by one or more sensors selected from the group consisting of a movement sensor, an orientation sensor, an accelerometer, a gyroscope, a micro-electro-mechanical systems (MEMS) sensor, a G-sensor, a tilt sensor, a rotation sensor, a pressure sensor, a light detecting sensor, such as a LiDAR sensor, an EIM sensor, a hormone sensor, a toxin sensor, a pH sensor, a temperature sensor, and/or a humidity sensor, and combinations thereof. A health status score may indicate to a user whether a particular daily activity and/or metric contribute positively or negatively to the overall health of the user's urogenital system and/or pelvic floor.

The database may be located on the electronic device, on an additional electronic device, or on the Internet (e.g., a web-located and/or cloud-based database). The electronic device may be connected to the database by a detachable cable, a Bluetooth connection, a Wi-Fi connection, and/or an internet connection. Communication with a particular type of electronic device, such as an Apple device, may require the use of a special authentication chip.

Additionally, the electronic device can include a user interface. The user interface can be programmed to display data and/or to provide instructions for use of the intravaginal device.

The intravaginal device (e.g., main body (e.g., the substantially ring shaped form) and/or tether) further includes a power source (e.g., a battery). The power source can be used to operate one or more components of the device, such as the sensor(s), transmitter, receiver, and the circuit board. In some instances, the power source is positioned within the substantially ring shaped form of the intravaginal device and connected to the component(s) by a wire and/or by a circuit board. The power source may be a rechargeable battery, such as a nickel-cadmium battery or a lithium ion battery, such as one compatible with wired or wireless (e.g., inductive) charging. Additionally, the external housing may include a power source connected to the transmitter or receiver, e.g., by a wire and/or by a circuit board. An ON/OFF switch can also be included.

The intravaginal device may further include a detachable cable connected to sensor(s) either directly or indirectly, e.g., by a wire or a circuit board. The detachable cable may also be configured to connect the intravaginal device to an electronic device. The detachable cable may also be configured to assist in the removal of the intravaginal device from its position within the vaginal canal (e.g., proximal to the cervix or vaginal cuff) of a user. In some instances, the detachable cable is the tether.

The intravaginal device may further include within the main body (e.g., the substantially ring shaped form) and/or tether a sensory output component for providing biofeedback to an individual. The sensory output component may be connected to the microcontroller and/or the sensor(s), e.g., by a wire and/or by a circuit board. The biofeedback relates to at least one performance metric as measured by the sensor(s). The performance metric can be proper execution of a PFL and/or a PFR, duration of time in which the intravaginal device has been in use (e.g., the time in which the intravaginal device has been at a position proximal to the cervix or vaginal cuff of the user (i.e., total insertion time), the time over which PFLs and/or PFRs have been performed, (i.e., total training time)), pH, and/or muscle quality. A performance metric may be a measurement of the overall health status of a user's urogenital system and/or pelvic floor (e.g., a measurement of muscle movement, muscle quality, muscle, strength, a biomolecule level (e.g., a hormone and/or a toxin level), pH, temperature, and/or humidity) obtained during daily monitoring (e.g., in substantially real-time) with an intravaginal device as the user performs her daily activities. The sensory output component may be configured to produce a visual, vibrational, and/or auditory signal as the biofeedback. The intravaginal device may be configured to notify the user when to remove the intravaginal device.

The intravaginal device may also be configured to deliver at least one pharmaceutical agent (e.g., 1, 2, 3, 4, 5, or more pharmaceutical agents) useful in the treatment of a PFD, or a symptom thereof (e.g., changes to muscle tone, changes to muscle strength, bladder leakage, anal or fecal leakage, pain, frequency, and urgency), to the tissues of the vagina, e.g., by transdermal and/or transmucosal delivery. Furthermore, an intravaginal device of the invention may be configured to treat an additional condition, disease, and/or related symptom that may be present in an individual having a PFD (e.g., an individual having a PFD who may benefit from training her pelvic floor muscles with an intravaginal device of the invention). An intravaginal device of the invention may be used to release a pharmaceutical that may act, e.g., locally and/or systemically, to treat, prevent, and/or ameliorate a PFD, or a symptom thereof, and/or an additional condition, disease, or related symptom.

The intravaginal device may be configured for use with a tool for insertion. The tool for insertion is capable of deforming the intravaginal device and/or deploying the intravaginal device at a location within the user (e.g., at a position proximal to the cervix or vaginal cuff).

The device may be used at home, work, physician's office, clinic, nursing home, pelvic health or other center or other locations suitable for the individual. A physician, nurse, technician, physical therapist, or central customer support may supply support for the patient/user.

Each of the components of the intravaginal device is described below.

Incorporation of a Pharmaceutical Agent into an Intravaginal Device

The intravaginal device may be configured to deliver a pharmaceutical agent to a female subject, e.g., as part of a treatment regime for a PFD and/or for the treatment of another disease or condition. The intravaginal device may be designed to deliver the pharmaceutical agent continuously, periodically, in response to a stimuli (e.g., a change in the vaginal environment, such as change in temperature, pH, and/or moisture level), in response to user input, and/or in response to data obtained from a sensor of the intravaginal device (e.g., in response to a movement of a pelvic floor muscle). In some instances, delivery of a pharmaceutical agent may be coordinated with the performance of a pelvic floor training exercise (e.g., a PFL or PFR), such that the pharmaceutical agent is delivered prior to, during, or after the performance of the pelvic floor exercise (e.g., a PFL or PFR). Delivery of a pharmaceutical agent may be coordinated with the performance of a daily activity and/or the measurement of the overall health status of a user's urogenital system and/or pelvic floor (e.g., a measurement of muscle movement, muscle quality, muscle, strength, a biomolecule level (e.g., a hormone and/or a toxin level), pH, temperature, and/or humidity) obtained during daily monitoring (e.g., in substantially real-time) with an intravaginal device as the user performs her daily activities.

In some instances, coordinated delivery of a pharmaceutical agent(s), such as a muscle stimulator and/or a muscle relaxant, may enhance the therapeutic benefit received through training with the intravaginal device. Delivery of a pharmaceutical agent that alleviates a symptom or discomfort associated with a PFD, e.g., changes to muscle tone, changes to muscle strength, bladder leakage, anal or fecal leakage, pain, frequency, and urgency, may improve patient compliance with a treatment regime utilizing an intravaginal device of the invention.

Intravaginal Devices of the Invention Configured as a Monolithic System

An intravaginal device of the invention may be configured to release at least one pharmaceutical agent (e.g., 1, 2, 3, 4, 5, or more pharmaceutical agents) that may be evenly distributed throughout the material of the intravaginal device, e.g., of the main body or tether of the intravaginal device. A pharmaceutical agent may be mixed into the polymeric material (polymeric matrix) of an intravaginal device of the invention, e.g., in the range of about 1% to about 85% (w/w) (e.g., about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or 85% (w/w)), with respect to the total weight of the polymer matrix. For example, a therapeutically effective amount of at least one pharmaceutical agent (e.g., 1, 2, 3, 4, 5, or more pharmaceutical agents) may be mixed with a biocompatible elastomeric polymer and, optionally, a physiologically acceptable diluent, excipient, carrier, or adjuvant to form a mixture having, e.g., about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or 85% w/w ratio with respect to the total weight of the polymer; the mixture may then be cured in a mold having the shape of the intravaginal device to form a polymer matrix, which can be matured to form the intravaginal device. The amount of pharmaceutical agent may be varied depending on, for example, the desired dosing level, the particular pharmaceutical agent, the release rate effect of excipients used in the device, and/or the particular elastomeric polymer(s) employed. In some instances, the intravaginal device may be configured to have a shell design, in which the pharmaceutical agent is contained in a narrow band (e.g., an annulus) between a non-medicated central elastomeric core and a narrow, outer rate controlling non-medicated elastomeric sheath.

Non-limiting examples of suitable biocompatible elastomers that may be mixed with a pharmaceutical agent to form an intravaginal device of the invention include silicones (organo polysiloxanes including dimethylpolysiloxanes), polyethylene-co-poly (vinyl acetate), styrene-butadiene-styrene block copolymers, polyphosphazenes, poly(isoprene), poly (isobutylene), polybutadienes, polyurethanes, nitrile rubbers, neoprene rubbers or mixtures thereof.

Intravaginal Devices of the Invention Configured as a Reservoir System

In another configuration, the intravaginal device may contain within the main body and/or tether at least one delivery module or component that contains a pharmaceutical agent useful in the treatment of a PFD, or the symptoms thereof (e.g., changes to muscle tone, changes to muscle strength, bladder leakage, anal or fecal leakage, pain, frequency, and urgency), or another disease or condition affecting a female subject, e.g., as described herein. The delivery module or component may be variously arranged within the main body and/or tether and may be, for example, an inner core (e.g., a replaceable core), reservoir (e.g., a single chamber or multiple chamber reservoir, a replaceable reservoir, and/or a refillable reservoir), or other delivery module from which at least one pharmaceutical agent (e.g., 1, 2, 3, 4, 5, or more pharmaceutical agents) may be released to contact vaginal tissue. An intravaginal device may also be configured with one or more of the pharmaceutical agent delivery options (e.g., a coating and a delivery module). Not shown, but contemplated by the invention, are similar arrangements of the pharmaceutical drug delivery modules within the tether of the intravaginal device of the invention.

An intravaginal devices of the invention may include a reservoir, e.g., a reservoir containing a pharmaceutical agent. The reservoir may be formed, at least in part, by an elastomeric polymer (e.g., a hydrophilic elastomer or non-swellable elastomer) or a drug permeable material. Non-limiting examples of suitable polymeric materials that be used to form a reservoir within an intravaginal device of the invention include silicones, poly(ethylene-co-vinyl acetate), styrene-butadiene-styrene block copolymers, poly(hydroxyethylmethacrylate) (pHEMA), polyvinyl chloride, polyvinyl acetate, poly(vinyl alcohol), polyesters, poly(acrylic acid)s, polyethers, polyurethanes, polyacrylonitriles, polyethylene glycols, polyethylene, polypropylene, polymethylpentene, polybutadiene, cellulose and its derivatives and polyamides, and mixtures thereof. Suitable non-polymeric reservoir materials include, but are not limited to, pharmaceutically acceptable low-melting point waxes, such as stearyl alcohol, or semi-synthetic glycerides of saturated fatty acids (e.g., those of C8 to C18), or a mixture thereof.

The reservoir can hold (or contain) a liquid, solid, or semi-solid composition that includes at least one pharmaceutical agent (e.g., 1, 2, 3, 4, 5, or more pharmaceutical agents). These compositions can, but need not, include a pharmaceutically acceptable diluent, excipient, carrier, or adjuvant in addition to a pharmaceutical agent. Non-limiting examples of such carriers and excipients include, e.g., glycerol, cellulose (e.g., hydroxyethylcellulose), castor oil, polyethylene glycol, polyoxyethylene castor oil, silicone oil, mineral oil, and poloxamer. In some instances, the reservoir holds a solid selected from powders, pellets, nanoparticles, microcapsules, or a combination thereof. In some instances, the reservoir is filled with a solid drug-containing polymer, e.g., as pellets or as a single core. The solid may include one or more diluents, densification agents, bulking agents, lubricating agents, glidants, or osmotic agents. For example, the solid may include one or more of cellulose, starch, sugar, sodium salt, potassium salt, calcium salt, and magnesium salt. In some instances, a reservoir may be, e.g., removable and arranged within a holder positioned within the intravaginal device.

The pharmaceutical agent-containing reservoir can also include a non-swellable elastomer, such as TECOFLEX®, or a hydrophilic elastomer, including but not limited to hydrophilic poly(ether urethanes), such as TECOPHILIC®-HP-60D-60, at weight fractions ranging from 30% to 95% w/w (e.g., 30%, 40%, 50%, 60%, 70%, 80%, 90%, 95% or a range between and including any two such values) to aid in mechanical reinforcement and/or processability. In some instances, water-soluble porogens, such as salt crystals, are incorporated into a polymeric material of the intravaginal device. Such porogens dissolve upon exposure to vaginal fluid as it permeates the intravaginal device and creates pores through the tubing wall, allowing for faster drug release. In some instances, pores or holes are arranged to expose at least a portion of the reservoir to vaginal fluid, e.g., to allow release of the pharmaceutical agent by diffusion.

Intravaginal Devices of the Invention Configured with a Coating

Alternatively, the intravaginal device may have a coating, layer, and/or gel on a surface thereof that contains the at least one pharmaceutical agent (e.g., 1, 2, 3, 4, 5, or more pharmaceutical agents). The coating, layer, and/or gel may be applied at the time of manufacture of the intravaginal device or it may be applied at a later time, e.g., by an individual user or a medical practitioner. The coating, layer, and/or gel may cover all or a portion of an intravaginal device surface (e.g., 5%, 10%, 20%, 30%, 40%, 50%, 60%, 70%, 80%, 90%, or more of the surface of the intravaginal device). Release of a pharmaceutical agent from a coating, layer, and/or gel may occur, e.g, by diffusion when in contact with the fluids of the vagina.

Sensors that can be Used to Measure a Performance Metric and/or a Characteristic of a Pelvic Floor Disorder (PFD)

Sensors that can be used in the intravaginal device (e.g., within the main body (e.g., the substantially ring shaped form) and/or tether) of the invention (e.g., to measure the occurrence and/or quality of pelvic floor lifts (PFLs) and/or pelvic floor relaxations (PFRs) performed by an individual when the sensor is positioned at a location proximal to the subject's cervix or vaginal cuff) include, but are not limited to, movement sensors, accelerometers, gyroscopes, micro-electro-mechanical systems (MEMS) sensors, G-sensors, tilt sensors, rotation sensors, light detecting sensors, such as light detecting and ranging (LiDAR) sensors, and electrical impedance myography (EIM) sensors. One (e.g., 1, 2, 3, 4, 5, 6, 7, 8, 9, 10, or 20) or more sensors (e.g., movement sensors, accelerometers, gyroscopes, micro-electro-mechanical systems (MEMS) sensors, G-sensors, tilt sensors, rotation sensors, light-detecting sensors (e.g., LiDAR sensors), and EIM sensors) can be incorporated into the main body of the intravaginal device and/or within a tether (e.g., a flexible cord or ribbon) that can be optionally attached, e.g., by a removable or permanent connection, to the main body of the intravaginal device. The sensors may be arranged within the main body, tether, and/or sleeve of an intravaginal device of the invention. The sensors may be distributed evenly or unevenly throughout the main body and/or tether, such that the distribution of the sensors allows for the measurement of the quantity and quality of PFL and/or PFR performed by an individual using the intravaginal device. The device may also contain an electrode and/or a light generating component.

The sensor(s) is configured to measure a movement of at least one muscle of the pelvic floor (e.g., the levator ani, e.g., the pubococcygeus, ileococcygeus, coccygeus, and/or puborectalis muscles) or associated connective tissue during a PFL and/or PFR. An intravaginal device of the invention may be configured to provide daily monitoring, e.g., in substantially real-time, of the overall health status of the urogenital system and/or pelvic floor. An intravaginal device capable of providing daily monitoring may contain one or more sensors selected from the group consisting of a movement sensor, accelerometer, gyroscope, micro-electro-mechanical systems (MEMS) sensor, G-sensor, tilt sensor, rotation sensor, a light detecting sensor, such as a light detecting and ranging (LiDAR) sensor, and electrical impedance myography (EIM) sensor, a pressure sensor, a pH sensor, a humidity sensors, a temperature sensor, a hormone sensor, and a toxin sensor. Such an intravaginal device may be able to identify changes in vaginal conditions that may affect a user's health, such as changes in the user's muscle quality and/or muscle strength, a change in pH, in the level of a hormone and/or a toxin (e.g., a hormone and/or toxin level associated with a disease state, such as a PFD, a cancer, and/or a bacterial, fungal, or viral infection). In some instances, the movement can be an upward movement (e.g., a lifting movement, e.g., a movement in the cranial direction) of at least about 1-4 cm (e.g., about 1, 2, 3, or 4 cm). In some instances, the movement can be a downward movement (e.g., a dropping movement, e.g., a movement in the caudal direction) of at least about 1-4 cm (e.g., about 1, 2, 3, or 4 cm). The sensors within the intravaginal device (e.g., within the main body and/or tether) are positioned such that when the intravaginal device is inserted into a user the sensors face the ventral direction (e.g., anterior direction). The sensor and/or combination of sensors is capable of determining the orientation of the intravaginal device in the x, y, z-axis and can be configured to provide feedback to the individual when they have inserted the intravaginal device correctly.

In some instances, the device includes multiple sensors (e.g., 2, 3, 4, 5, 6, 7, 8, 9, 10, or 20 sensors) of the same type (e.g., multiple movement sensors, multiple accelerometers, multiple gyroscopes, multiple light sensors, such as LiDAR sensors, or multiple electrical impedance myography (EIM) sensors). In other instances, the device includes multiple sensors of different types, such as a combination of different types of sensors (e.g., at least two different types of sensors; e.g., at least two different sensors selected from the following groups: movement sensors, accelerometers, gyroscopes, lights detecting sensors, such as LiDAR sensors, EIM sensors, micro-electro-mechanical systems (MEMS) sensors, G-sensors, tilt sensors, and rotation sensors). In a particular instance, the device contains an accelerometer, such as a multiple-axis accelerometer, a gyroscope, such as a multiple-axis gyroscope, a MEMS sensor, and/or an EIM sensor. An exemplary sensor that can be used to measure PFLs and/or PFRs or muscles movements that occur while the user performs her daily activities is the STMicroelectronic LIS331DLH 3-axis liner accelerometer. The device may also include one or more electrodes and/or one or more light generating components (e.g., an optical transmitter, such as a light-emitting diode (LED) or a laser diode).

Additional sensors that can be used to measure at least one (e.g., 1, 2, 3, 4, 5, 6, 7, 8, 9, or 10) or more performance metrics and/or at least one (e.g., 1, 2, 3, 4, 5, 6, 7, 8, 9, or 10) or more characteristic of a subject's pelvic floor disorder (PFD) include, but are not limited to, pressure sensors, temperature sensors, pH sensors, and muscle quality sensors. Exemplary muscle quality sensors are described in International Publication No. WO2012149471A3, incorporated herein by reference in its entirety. The additional sensor can be incorporated into the main body of the intravaginal device and/or within a tether (e.g., a flexible cord or ribbon) that can be optionally attached, e.g., by a removable or permanent connection, to the main body of the intravaginal device.

A sensor of the invention may also be connected to a pharmaceutical delivery module or component arranged within the intravaginal device to enable the delivery of a pharmaceutical agent to an individual user in response, e.g., to data collected by a sensor(s), at a predetermined time, e.g., before, after, or during the performance of a PFL and/or PFR and/or a daily activity detected during daily monitoring. Recorded data from a sensor(s) may, e.g., be run through a control circuit that recognizes the characteristic patterns of a pelvic floor movement and in turn controls (e.g., initiates) the release of a pharmaceutical agent from a delivery module of the intravaginal device. In some instances, release may be initiated by turning on a heating element connected to the sensor, e.g., to release a pharmaceutical agent, e.g., a pharmaceutical agent inside a heat-sensitive polymeric material, reservoir, or coating. A non-limiting example of a control circuit that may be incorporated into an intravaginal device of the invention to control pharmaceutical agent release is described in, e.g., Son et al. (*Nature Nano.* 9:397-404, 2014), which is incorporated herein by reference in its entirety.

Electrical Impedance Myography (EIM) Technologies

The intravaginal device may be configured to utilize and include electrical impedance myography (EIM) technologies. The intravaginal device may contain an EIM sensor that can be used to measure a characteristic during the performance of a pelvic floor lift and/or relaxation. The EIM sensor may serve as the primary sensor or it may function as an auxiliary sensor, e.g., in combination with a MEMS sensor. An EIM sensor measures electrical bioimpedance, i.e., the effect of tissue structure and properties (e.g., muscle fiber atrophy, muscle fiber organization, deposition of fat and connective tissues, and inflammation) on the flow of an electrical current. To measure electrical bioimpedance, an electrical current, e.g., a high-frequency electrical current and/or a multi-frequency electrical current, can be applied to a tissue (e.g., pelvic floor tissues), e.g., by electrodes, and the resultant surface voltage patterns can be measured, e.g., by electrodes, and analyzed. Generally, the voltage measured is proportional to tissue resistance (R).

In practice, there is a time shift, between the application of an electrical current (sinusoid "a") by an electrode and the generation of the measured voltage difference (sinusoid "b"), due to the inherent, capacitive nature of myocyte (e.g., muscle cell) membrane lipid bilayers. This capacitive nature of muscle cells allows the electrical current (e.g., the charge) applied to a tissue to be stored and released out of phase with the applied electrical current, a process referred to as reactance (X). Reactance (X) and resistance (R) values may be combined to obtain the summary phase angle ($\theta$) via the relationship $\theta=\arc \tan(X/R)$. The obtained phase angle ($\theta$), reactance (X), and resistance (R) values may be used individually or in combination to measure a characteristic of the pelvic floor (e.g., the progression of, or resolution of, a pelvic floor disorder). For example, an increased resistance (R) value may be obtained when a tested pelvic floor tissue contains connective tissue, fat, and has a low level of muscle mass. In another example, a pelvic floor tissue experiencing muscle fiber atrophy and/or muscle fiber loss can result in a low reactance (X) value being measured.

In particular instances, disease progression can be characterized by a change (e.g., an increase and/or a decrease) in the value of the phase angle ($\theta$), reactance (X), and/or resistance (R), as compared to a reference (e.g., baseline) value. A reference value may be obtained, e.g., during the first use of the intravaginal device, such as during a calibration step. The reference values of the phase angle ($\theta$), reactance (X), and/or resistance will depend on the status, e.g., health, of the pelvic floor tissues. In general, phase angle ($\theta$) and reactance (X) values will decrease, as compared to the reference levels, as a pelvic floor disorder characterized by the loss of muscle tone (e.g., muscle fiber atrophy) advances. In particular instances, during treatment with an intravaginal device of the invention, an increase of about 5% or more (e.g., 5, 10, 20, 30, 40, 50, 60, 70, 80, 90, or 100%) in the phase angle ($\theta$) and/or the reactance (X) values, as compared to a reference value, may indicate an improved status (e.g., increased muscle quality) of the pelvic floor tissues. Furthermore, a decrease in the resistance (R) of about 5% or more (e.g., 5, 10, 20, 30, 40, 50, 60, 70, 80, 90, or 100%), as compared to a reference value, may indicate an improved status (e.g., increased muscle quality) of the pelvic floor tissues.

Two additional aspects of EIM technologies are applicable to their use in the intravaginal device of the invention. The measured values of phase angle ($\theta$), reactance (X), and/or resistance (R) can be dependent on the frequency of the electrical current used to obtain EIM data. Thus, performing EIM measurements across a range of frequencies may help to characterize tissue, e.g., by using an electrical current with a frequency and/or multiple frequencies (e.g., a high-frequency alternating current) between about 1 kHz to about 10 MHz (e.g., 1, 2, 3, 4, 5, 6, 7, 8, 9, 10, 20, 30, 40, 50, 60, 70, 80, 90, 100, 200, 300, 400, 500, 600, 700, 800, 900, or 1000 kHz; or 1, 2, 3, 4, 5, 6, 7, 8, 9, 10 MHz). Additionally, EIM data demonstrates electrical anisotropy-directional dependence of current flow, because electrical current generally flows more easily parallel to the orientation of muscle fibers than perpendicular to the orientation of muscle fibers. Alterations in electrical anisotropy can also be used to measure a characteristic of the pelvic floor muscles, e.g., to monitor the progression of a pelvic floor disorder. For example, in pelvic floor disorders characterized by a loss of muscle tone (e.g., muscle fiber atrophy) a decrease in anisotropy, as compared to a reference level of anisotropy, can indicate an improved status of the pelvic floor tissues (e.g., an increase in muscle quality). In some instances, the angle at which the EIM sensor contacts the vaginal tissues may be adjustable, to collect data from multiple angles. In other embodiments, more than one (e.g., 1, 2, 3, 4, 5, 6, 7, 8, 9, 10, or 20) EIM sensor is positioned to contact vaginal tissues at varying angles, such an overall value for electrical anisotropy within a pelvic floor tissue can be calculated.

In particular, the intravaginal device may be configured to deliver and to measure the effect of an electrical current (e.g., a high-frequency alternating current) applied to the tissues (e.g., the musculature and nerves) of the pelvic floor. The EIM technology included in the intravaginal device can be used to determine at least one characteristic of a tissue of the pelvic floor, such as a characteristic selected from the group consisting of muscle quality and/or function, relative force-generating capacity, fat percentage, and/or status (e.g., progression) of a pelvic floor disorder. Exemplary EIM sensors, such as a SKULPT® sensor, are described in International Publication Nos. WO2012149471A2, WO2015031278A1, and WO2016099824A; in U.S. Publication Nos. US20160038053A1 and US20160157749A1; and in U.S. Pat. Nos. 8,892,198 and 9,113,808, which are incorporated herein by reference in their entirety.

The intravaginal device may also include at least one electrode (e.g., 1, 2, 3, 4, 5, 6, 7, 8, 9, 10, or 20 electrodes) configured to deliver an electrical current, such as a high-frequency alternating current, to the tissues of the pelvic floor. Additionally, the intravaginal device may include at least one electrode (e.g., 1, 2, 3, 4, 5, 6, 7, 8, 9, 10, or 20 electrodes) configured to measure bioimpedance of the tissues of the pelvic floor. The delivery of an electrical current to and/or the measurement of bioimpedance of the tissues of the pelvic floor can be achieved through the inclusion of at least one EIM sensor (e.g., 1, 2, 3, 4, 5, 6, 7, 8, 9, 10, or 20 EIM sensors), such as a SKULPT® sensor, in the intravaginal device. The electrode may be integrated with, and part of, the bioimpedance sensor (e.g., an EIM sensor) or the electrode may be a separate component. In particular embodiments, the intravaginal device includes at least one SKULPT® sensor (e.g., 1, 2, 3, 4, 5, 6, 7, 8, 9, 10, or 20). The electrode(s), EIM sensor(s), and/or SKULPT® sensor(s) may be located within the main body and/or tether of the intravaginal device.

The sensors may be disposed along the tether and/or around the main body (e.g., a complete or incomplete ring form). A measure of bioimpedance of the vaginal canal could be computing using the characteristics of the voltage signal measured by electrodes 915 and the current applied by another electrodes 910. The bioimpedance could then be used to infer characteristics of the tissue, including muscle quality and fat content. A measure of bioimpedance of the pelvic floor muscles could be computed using the characteristics of the voltage signal measured by electrodes 905 and the current applied by electrodes 900. The bioimpedance could then be used to infer characteristics of the tissue including muscle quality and fat content.

The SKULPT® sensor(s) of the intravaginal device may also be connected to a delivery module or component of the intravaginal device and configured to deliver a pharmaceutical agent to an individual user, e.g., in response to a measurement of muscle quality obtained by a SKULPT® sensor(s). Recorded data from a SKULPT® sensor(s) may, e.g., be run through a control circuit that recognizes the characteristic patterns of a pelvic floor movement and/or a change in muscle quality and in turn controls (e.g., initiates) the release of a pharmaceutical agent from a delivery module (e.g., polymeric material, reservoir, or coating) of the intravaginal device.

Light Detecting Sensors

The intravaginal device may also be configured to utilize and include sensing technologies based on light, e.g., laser or LED light, such as light detection and ranging (LiDAR) sensors. In the art, LiDAR sensors have been used for generating high-resolution maps, e.g., three-dimensional (3D) maps of surfaces and objects, and for the tracking of an object's movements. In practice, LiDAR sensors measure, e.g., how far away each pixel in a 3D space is from the emitting device (e.g., an intravaginal device containing a LiDAR sensor), as well as the direction to that pixel, which allows for the creation of a full 3D model of the area around the sensor (e.g., the pelvic floor and vaginal canal). A LiDAR sensor is configured to transmit a beam of light, and then measure the returning signal when the light reflects off an object (e.g., the tissues of the pelvic floor and vaginal canal). The time that the reflected signal takes to return to the LiDAR sensor provides a direct measurement of the distance to the object (e.g., a tissue comprising the pelvic floor and/or vaginal canal). Additional information about the object, e.g., velocity or material composition, can also be determined by measuring certain properties of the reflected signal, such as the induced Doppler shift (e.g., a change in frequency). Finally, by steering the transmitted light and/or the incorporation of multiple LiDAR sensors, many different points of an environment can be measured to create a full 3D model. Exemplary LiDAR sensors are described in, e.g., U.S. Publication No. US20150346340A1, incorporated herein by reference in its entirety.

The intravaginal device may include at least one light detecting sensor, such as a LiDAR sensor (e.g., 1, 2, 3, 4, 5, 6, 7, 8, 9, 10, or 20 LiDAR sensors), for example an on-chip LiDAR sensor. Inclusion of the LiDAR sensor would allow the intravaginal device to collect mapping data, e.g., data on the size, shape, contour, structure, and/or texture of the pelvic floor and of the vaginal canal to generate a three-dimensional (3D) model of the pelvic floor tissues and vaginal canal. Additionally, one or more LiDAR sensors may be configured to measure a pelvic floor lift and/or relaxation. The intravaginal device may contain a LiDAR sensor that is configured to measure the performance of a pelvic floor lift and/or relaxation. The LiDAR sensor may serve as the primary sensor or it may function as an auxiliary sensor. A LiDAR sensor may be located within the main body and/or tether of the intravaginal device. The data collected from other sensors, for example can be integrated with the 3D model to monitor the status (e.g., strength) of particular muscles of the pelvic floor during treatment with the intravaginal device. A light generating component may be integrated with, and part of, the light detecting sensor (e.g., a LiDAR sensor) or the light generating component may be a separate component.

The light sensor(s) (e.g., a LiDAR sensor) of the intravaginal device may also be connected to a delivery module or component of the intravaginal device and configured to deliver a pharmaceutical agent to an individual user, e.g., in response to a measurement obtained by a light sensor(s) (e.g., a LiDAR sensor). Recorded data from a LiDAR sensor(s) may, e.g., be run through a control circuit that recognizes the characteristic patterns of a pelvic floor movement and in turn controls (e.g., initiates) the release of a pharmaceutical agent from a delivery module (e.g., polymeric material, reservoir, or coating) of the intravaginal device.

Hormone and Toxin Sensors

The intravaginal device may also have a sensor that is capable of detecting, identifying, and/or measuring a molecule (e.g., a hormone, a toxin, a small molecule, a polynucleotide, and/or a polypeptide). Such a sensor may be capable of detecting a 1%, 2%, 3%, 4%, 5%, 6%, 7%, 8%, 9%, 10%, 20%, 30%, 40%, 50%, 60%, 70%, 80%, 90%, or more change (e.g., increase and/or decrease) in the level of a molecule (e.g., a hormone, a toxin, a small molecule, a polynucleotide, and/or a polypeptide) as compared to a reference level obtained, e.g., during calibration with an intravaginal device of the invention and/or known in the art. The level of a molecule (e.g., a hormone, a toxin, a small molecule, a polynucleotide, and/or a polypeptide) that may contribute to and/or be associated with the onset and/or progression of a PFD and/or another disease or condition, as described herein, is well known in the art. Non-limiting examples of such sensors are described in, e.g., U.S. Pat. No. 5,209,238 and in U.S. Publication No. US20090299156A1, which are each incorporated herein by reference in their entirety.

An Exchangeable, Separable, and/or Modular Tether

An intravaginal device of the invention may include an optional tether and/or sleeve. A tether of the invention may include one or more tether modules or separable tether portions (e.g., 1, 2, 3, 4, 5, 6, 7, 8, 9, 10, 20, 30, or more tether modules or separable tether portions). Each tether module or separable tether portion may include a connector, e.g., a flexible connector, by which multiple tether modules or separable tether portions may be connected, e.g., linked, to form a tether of varying length. A sleeve of the invention may be, e.g., a flexible cover, that may be arranged to surround and encapsulate a tether (e.g., 1, 2, 3, 4, 5, 6, 7, 8, 9, 10, 20, 30, or more tether modules or separable tether portions). A sleeve of the invention may alternatively, or additionally, cover the main body of an intravaginal device of the invention.

A tether or one or more tether modules or separable tether portions and/or a sleeve may be configured with one or more sensors (e.g., 1, 2, 3, 4, 5, 6, 7, 8, 9, 10, 20, or more sensors), as described herein, and including at least one sensor selected from the group consisting of a movement sensor, accelerometer, gyroscope, micro-electro-mechanical systems (MEMS) sensor, G-sensor, tilt sensor, rotation sensor, a light detecting sensor, such as a light detecting and ranging (LiDAR) sensor, and electrical impedance myography (EIM) sensor, a pressure sensor, a pH sensor, a humidity sensors, a temperature sensor, a hormone sensor, and/or a toxin sensor. A tether or one or more tether modules or separable tether portions may be configured with one or more energy transmitters (e.g., RF transmitters).

Alternatively, or additionally, a tether or one or more tether modules or separable tether portions and/or a sleeve may be configured to deliver one or more pharmaceutical agents (e.g., 1, 2, 3, 4, 5, 6, 7, 8, 9, 10, 20, or more pharmaceutical agents), as described herein. In some instances, a tether or one or more tether modules or separable tether portions and/or a sleeve may include one or more delivery modules or components (e.g., 1, 2, 3, 4, 5, 6, 7, 8, 9, 10, 20, or more delivery modules or components), such as those described herein and including an inner core, reservoir, coating layer, and/or gel.

Figure 26:
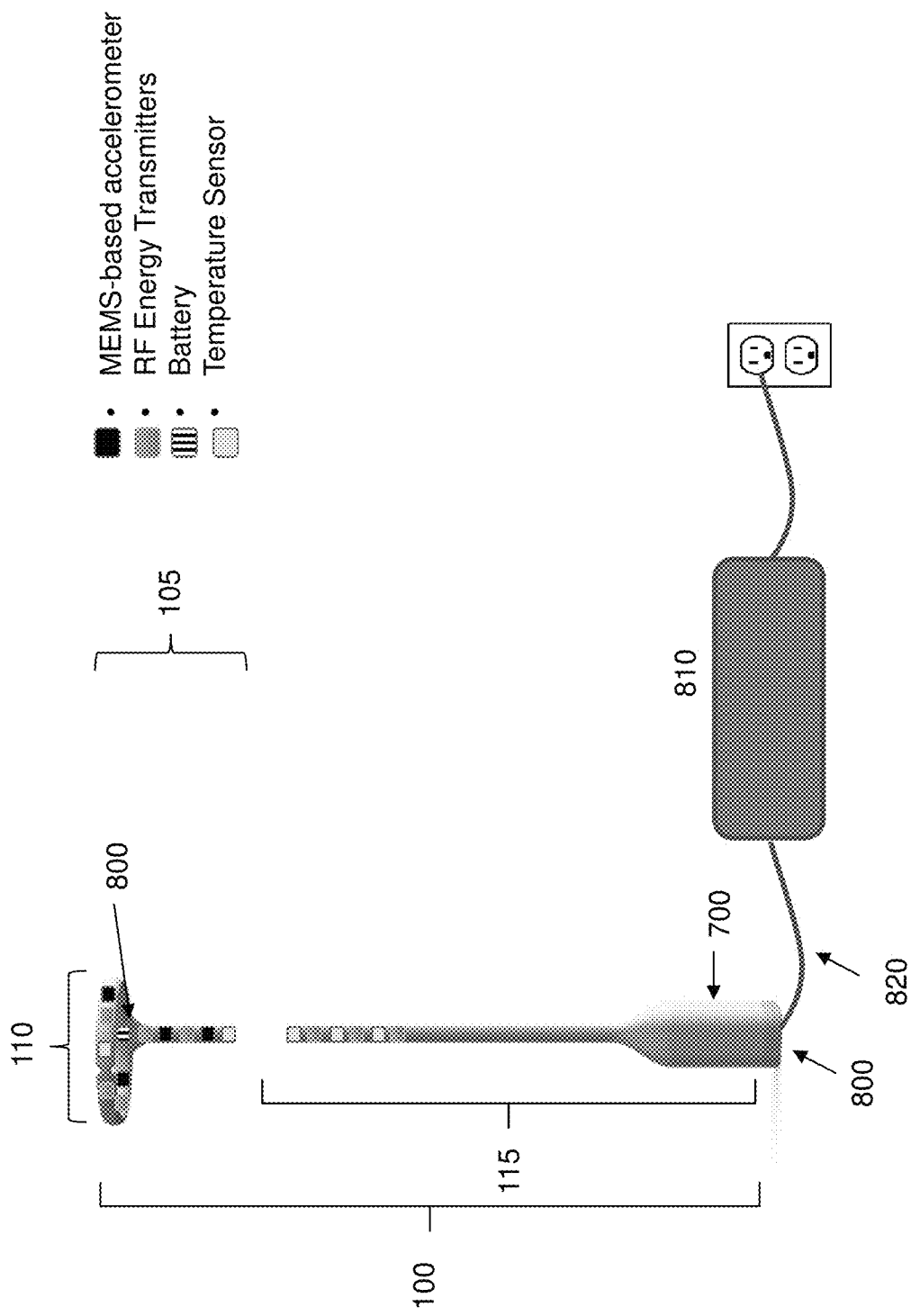
FIG. 26 is a schematic showing intravaginal device 100 with main body 110, tether 10, circuit board 700, and power box 810, which is part of power cord 820 that connects intravaginal device 100, and may also be connected to an AC power source. Intravaginal device 100 contains MEMS accelerometers, RF energy transmitters, and temperature sensors, positioned around main body 110 and along the length of tether 10. Tether 10 is configured with separable tether 115 that can connect to main body 100 and a portion of tether 10 that can remain in the vagina as a long-term wearable device 105. Separable tether 115 functions as a short-term device that can be connected to power cord 820 to power the long term wearable device (e.g., with external power source 810) or to recharge a battery in battery 800, if present.
Figure 27:
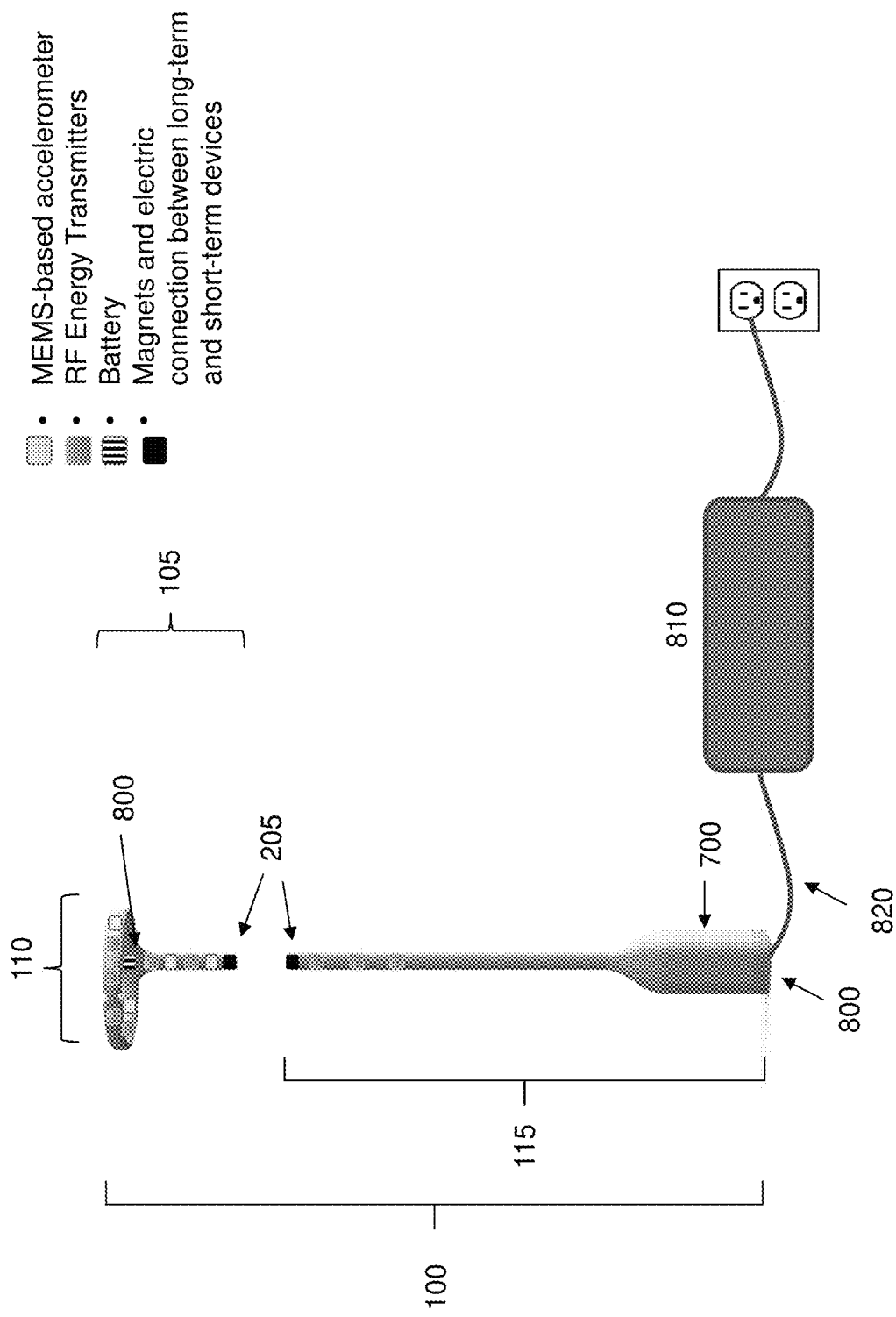
FIG. 27 is a schematic showing intravaginal device 100 with separable tether 115. Magnets and/or electrical connections 205 are present at the contact point between the top part and the bottom part of tether 10. Magnets and/or electrical connections 205 provide communication between the long-term wearable devices and separable tether 115. Separable tether 115 functions as a short-term device that can be connected to power cord 820 to power the long term wearable device (e.g., with external power source 810) or to recharge a battery in battery 800, if present.

In certain embodiments, the tether is configured as a separable tether, which may be a single separable piece of the tether or may be two or more separable portions of the tether. The separable tether(s) can be connected, for example, by a magnetic or interlocking connection. The contact point can also include an electrical connection that allows communication between the separable tether(s) and, e.g., a power supply (e.g., an AC power supply or a battery-powered supply; FIGS. 26-27). This may be useful for applications where recharging the device is necessary or in order to power the device during certain therapeutic applications.

Energy Transmitters

Energy transmitters 210, such as energy transmitters, lasers, or electrical stimulation transmitters may be integrated into the intravaginal device. RF transmitters operate at frequencies, for example, from 1 kHz to 100 MHz. The power level of RF transmitters may vary from 1 mW to 500 W. RF transmitters emit energy in the form of heat and can be used to provide thermal energy to local tissue area of the vagina and vaginal canal that comes into contact with or is in proximity of the transmitters. RF transmitters may emit pulses of energy (e.g., in 1-5 second bursts) or may emit energy for extended durations (e.g., 1-30 minutes). RF transmitters may be powered wirelessly or by a wired power source. The energy transmitters can communicate, e.g., via a wireless communication (e.g., Bluetooth or Wi-Fi), such as with an antennae and/or an authentication chip (e.g., for communicating with and transmitting data to a peripheral device, such as a smart product, e.g., tablets, computers, and smartphones (e.g., iPhone, iPads, and other Apple or Android computing devices).

Microcontrollers

A microcontroller (e.g., microcontroller unit (MCU)) is a small computer (e.g., a system on a chip (SOC)) that integrates all components of a computer or other electronic system into a single chip (e.g., an integrated circuit (IC) or microchip) and may contain a processor core, memory (e.g., non-transient storage), and programmable input/output peripherals (e.g., sensors). The MCU can be used within an embedded system, such as an intravaginal device, with a dedicated function, such as monitoring the performance of pelvic floor exercises and providing biofeedback. The MCU will typically contain a central processing unit (CPU) (e.g., a 4-bit to 64-bit processing unit, e.g., a 4-bit, a 32-bit, or a 64-bit processor), volatile memory (RAM) for data storage, operating parameter storage (e.g., ROM, EPROM, EEPROM, and/or Flash memory), discrete input and output pins (e.g., general purpose input/output pins (GPIO), serial input/output pins (e.g., universal asynchronous receiver/transmitter (UARTS), e.g., serial input/output pins for communication standards such as TIA (formerly EIA) RS-232, RS-422, and/or RS-485), other serial communication interfaces (e.g., Inter-Integrated Circuit (I$^2$C), Serial Peripheral Interface (SPI), Universal Serial Bus (USB), and Ethernet), peripherals, clock generator, converters (e.g., analog-to-digital and/or digital-to-analog converters), and in-circuit programming (ICSP) and/or in-circuit debugging (ICD) support.

Microcontrollers can contain at least one (e.g., 1, 2, 3, 4, 5, 6, 7, 8, 9, 10, 15, 20, 25, 30, 40, 50, 60, 70, 800, 80, 100, 150, or more) general purpose input and/or output pins (GPIO). GPIO pins are software configurable to either an input or an output state. GPIO pins configured to an input state are used to read sensors (e.g., movement, acceleration, rotation, pH, and/or muscle quality sensors) or other external signals. GPIO pins configured to the output state can drive an external device, such as a device capable of providing biofeedback (e.g., LEDs, motors).

An exemplary microcontroller useful in the featured invention is the Texas Instruments® MSP430F5438A, however other suitable microcontrollers may be used. This can be used to control the sensors, energy transmitters, and route power to any components within the intravaginal device.

Transmitter and Receiver

A transmitter and receiver may be positioned within the intravaginal device along with any additional components required to enable wireless communication (e.g., Bluetooth or Wi-Fi), such as an antennae and/or an authentication chip (e.g., for communicating with Apple products, e.g., iPhone, iPads, and other Apple computing devices). For example, Bluetooth communication can be performed by Roving Network's RN42APL-I/RM microchip. For authentication, for example, an Apple Authentication Chip 2.0C can be used to connect to the RN42APL-I/RM microchip via I$^2$C and allow the intravaginal device to communicate with Apple products. One example of an Apple chip is the iPod Authentication Coprocessor, with part number P/N MFI337S3959. The transmitter and receiver may also be housed in an external box and connected to the intravaginal device by a detachable cable.

Power Source

The power source may be a battery located within the intravaginal device (e.g., an internal battery) and can be connected to the electronic components that it will power (e.g., sensor(s), microcontroller, transmitter and receiver, RF transmitter, and sensory output component(s)) by either a circuit board (e.g., a flexible circuit board) or a wire. The intravaginal device can include an ON/OFF switch (e.g., a button), that can be activated, e.g., prior or post insertion of the intravaginal device, by the individual. The power state of the intravaginal device can be indicated to the individual, e.g., by a light (e.g., an LED), a vibration, and/or by a notification displayed on the user interface of the electronic device, e.g., via an accompanying software application). The internal battery may be rechargeable and/or replaceable, such as a nickel-cadmium battery or a lithium ion battery. The intravaginal device may be configured to allow for the battery to be charged by a charging cradle (e.g., a charging case), a detachable cable, and/or by inductive wireless charging technology.

In some instances, the internal battery has a sufficient charge to power the intravaginal device for an entire treatment period (e.g., about one day to about three years (e.g., about three to six weeks (e.g., at least one week) or three to six months)). The internal battery can be configured to modulate its power output level based on the usage state of the intravaginal device, e.g., by entering a lower-power state when the intravaginal device is not being used to measure a pelvic floor muscle movement (e.g., a pelvic floor lift (PFL) and/or a pelvic floor relaxation(PFR)). The usage state may be detected automatically by the intravaginal device, or be communicated to the intravaginal device by the electronic device and user interface, e.g., by the individual beginning a training session using the accompanying software application. The ON/OFF switch may also be configured to communicate to the intravaginal device when a training session will begin and thereby modulate the power state of the device. For example, the ON/OFF switch can be configured to respond to one long press (e.g., a 5-15 second press and hold) by turning on, while one short press (e.g., a 1-3 second press and hold) can cycle the intravaginal device into a training state during which sensor data can be collected, and a second short press (e.g., one 1-3 second press and hold) or a double press (e.g., two 1-3 second press and holds) can end a training session and place the intravaginal device into a power-saving (e.g., low-power) state.

In some instances, the power source is a battery located in a separate housing (e.g., an external battery) and connected to the intravaginal device, e.g., by a detachable cable. For example, power may be supplied through two replaceable and/or rechargeable AA batteries (e.g., 1.5V batteries). In some instances, the power is provided by a power cord that connects to, for example, a power box (e.g., an external battery) or AC outlet.

Materials

The intravaginal device (e.g., main body (e.g., the substantially ring shaped form) sleeve, and/or tether) may be fabricated from a variety of biocompatible materials. For example, silicone, polyethylene, polypropylene, polystyrene, polyester, polycarbonate, polyvinyl chloride, polyethersulfone, polyacrylate, hydrogel, polysulfone, polyetheretherketone, thermoplastic elastomers, poly-p-xylylene, fluoropolymers, rubber, and latex are suitable materials from which to fabricate the intravaginal device. Additionally, the intravaginal device (e.g., main body (e.g., the substantially ring shaped form) and/or tether) may be fabricated from or include components fabricated from metals and/or plastics. For example, the intravaginal device may contain a flexible spring, wire, or core structure (e.g., for providing tension, e.g., pushing against the vaginal walls of the individual to position and orient the intravaginal device at a location proximal to the individual's cervix or vaginal cuff) made from metal and/or plastic. The materials from which the intravaginal device is fabricated may be flexible or inflexible. In some instances, the intravaginal device (e.g., main body (e.g., the substantially ring shaped form) and/or tether) contains both flexible and inflexible materials.

When configured for delivery of a pharmaceutical agent the material of the intravaginal device (e.g., materials of the main body, tether, and/or a delivery module) may comprise a biocompatible polymeric material, e.g., that is permeable to the passage of the pharmaceutical agent. Acceptable polymeric materials include those that may release a pharmaceutical agent, e.g., by diffusion or through micropores or holes. The polymeric material may comprise, e.g., a thermoplastic polymer, such as a silicone elastomer, a polysiloxane, a polyurethane, a polyethylene., a polyethylene vinyl acetate (PEVA), ethylene-vinyl acetate (EVA), a cellulose, a polystyrene, a polyacrylate, a polyamide, and/or a polyester polymer. An EVA material may be useful due to its mechanical and physical properties (e.g., solubility of the drug in the material). The EVA material may be any commercially available ethylene-vinyl acetate copolymer, such as ELVAX®, EVATANE®, LUPOLEN®, MOVRITON®, ULTRATHENE®, ATEVA®, and VESTYPAR®, Additional non-limiting examples of materials useful in the manufacture of an intravaginal device configured for delivery of a pharmaceutical agent are described in, e.g., Malcolm et al. (*Int. J. Women. Health.* 4:595-605, 2012), U.S. Publication No. US20090004246A1, and U.S. Pat. Nos. 3,545,439, 4,822,616, 4,292,965, 8,858,977, 7,829,112, 4,215,691, 4,155,991, 7,910,126, and 4,012,496, each of which are herein incorporated by reference in their entirety.

Coatings

The intravaginal device (e.g., main body (e.g., the substantially ring shaped form), sleeve, and/or tether) may be coated with a substance, such as a biomaterial, to improve a property of the device, such as, e.g., adhesion of the intravaginal device to the tissue of the vaginal canal (e.g., the vaginal walls and/or the cervix). The biomaterial may be a biocompatible adhesive, such as a hydrogel e.g., hyaluronic acid (HA) or a derivative thereof. Optimally, the biomaterial is a biodegradable material. Additionally, the biomaterial may be formulated such that it performs its desired function (e.g., adhesion) for a predictable period of time (e.g., a time corresponding to the treatment period for an individual). The intravaginal device may also be coated with a lubricant, e.g., to ease insertion or removal of the device from the vagina.

The intravaginal device (e.g., the main body, tether, including tether module(s), and/or sleeve) may also have a coating, a layer, and/or a gel (e.g., on a surface of the device, such as an exterior surface) containing at least one pharmaceutical agent (e.g., 1, 2, 3, 4, 5, or more pharmaceutical agents) useful in the treatment of a PFD or the symptoms thereof (e.g., changes to muscle tone, changes to muscle strength, bladder leakage, anal or fecal leakage, pain, frequency, and urgency), or another disease or condition affecting a female subject, e.g., as described herein. For example, the device may be coated with a layer comprising a pharmaceutical agent either completely or partially. Such a coating may be a temperature-sensitive material, such as wax, that melts at the body temperature. Alternatively, the coating may comprise a biodegradable polymer designed to allow pharmaceutical agent release by bulk or surface erosion and include natural and synthetic polymers alone or in combination with other materials, for example, polysaccharides (e.g., alginate, dextran, cellulose, collagen, and chemical derivatives thereof), proteins (e.g., albumin and gelatin and copolymers and blends thereof), polyhydroxy acids (e.g., polylactides, polyglycolides, polyethylene terephthalate, polybutyric acid, polyvaleric acid, polylactide-cocaprolactone, polyanhydrides, polyorthoesters, and blends and co-polymers thereof). The coating may also comprise a non-degradable polymer (e.g., polyamides, polyethylene, polypropylene, polystyrene, polyvinyl chloride, polymethacrylic acid, and derivatives thereof), or any other suitable coating material that coats all or at least a portion of the device.

Physical and chemical properties of the coatings can be tailored to optimize their intended use, such as controlling the rate of release of the pharmaceutical agent incorporated therein. Pharmaceutical agent release from the coating can occur, e.g., by diffusion or erosion, or by a combination of both, leading to immediate or controlled, rapid, slow, continuous, or pulsed delivery of the pharmaceutical agent to and/or through the vaginal tissue. The rate of agent release may be affected by the physicochemical properties of the agent, the composition of the coating, and/or on the surrounding media at the site of administration.

Non-limiting examples of coatings useful in the manufacture of an intravaginal device configured for delivery of a pharmaceutical agent are described in, e.g., U.S. Publication No. US20050276836A1 and U.S. Pat. No. 4,292,965, which are herein incorporated by reference in their entirety.

A Tool for Insertion of the Intravaginal Device

The intravaginal device may be inserted with an insertion tool (see, e.g., PCT Application No. PCT/US2017/044444, the disclosure of which is hereby incorporated in its entirety). The insertion tool may deform (e.g., bend, twist, compress, pull, and/or shape) and hold the intravaginal device in such a way that it can be deployed from the insertion tool at an appropriate location (e.g., a location proximal to the cervix or vaginal cuff of an individual) and in an appropriate orientation (e.g., a position that allows for optimal sensor measurements to be obtained) within an individual. The insertion tool may comprise a device housing configured to hold and shape the intravaginal device, and a plunger configured to apply the necessary force to push the intravaginal device from the device housing an deploy the intravaginal device inside the individual. The insertion tool can be configured for use with or coated with a lubricant to ease the insertion process. Insertion tool 400 contains an elongated shaft applicator, which houses intravaginal device 100. Insertion tool 400 may also contain upper portion 610 and lower portion 620, which may be joined near the distal end by hinge 630. Upper portion 610 and lower portion 620 may clasp the intravaginal device 100 before insertion into the vagina. After insertion, the ends of upper portion 610 and lower portion 620 may be pressed to release the device while removing insertion tool 400, leaving intravaginal device 100 in place inside the vagina. The insertion tool or applicator may be disposable or may be reused, e.g., after cleaning by methods known in the field (e.g., water and soap or other hygienic or sterilization methods). As the main body of the intravaginal device can have a diameter of about 20 mm to about 80 mm and a thickness of about 0.1 mm to about 1 mm, and the tether can have a length of about 14 cm or less and a width of about 1 to about 10 mm, the insertion tool may be configured to comprise slightly larger dimensions such that it can enclose or deform the device. The X dimension may be, e.g., from about 0.2 mm (about twice the thickness of the ring) to about 100 mm (slightly larger than the diameter of the ring when not deformed), the Y dimension may be e.g., from about 0.1 mm to about 50 mm, and the Z dimension may be e.g., from about 0.2 mm to about 115 mm.

A Database

The database may be located on a local electronic device (e.g., a computer, phone, or tablet) or on a remote electronic device that can communicate via the internet (e.g., a web-located and/or cloud-based database). The database can be a central database that collects, stores, and performs calculations with the sensor data collected from an intravaginal device used by an individual. Sensor data and additional data provided by an individual (e.g., information provided by an individual on symptoms of a pelvic floor disorder that they have experienced, e.g., answers to a questionnaire) may be communicated to (e.g., uploaded to) the database on a periodic basis from the intravaginal device. In some instances, communication with the database is substantially continuous (e.g., upload of data occurs in substantially real-time during the performance of a pelvic floor exercise). In other instances, communication with the database occurs on an hourly or daily basis (e.g., at least one per hour and/or at least once per day) or when initiated by the user. The database can be reviewed by the user after treatment to assess the progress. The data could also been transmitted to the healthcare provider (e.g., automatically, by a third party, or by the user).

A User Interface

The user interface may comprise a software application configured to provide an interactive display to an individual of her (i) present, daily, weekly, monthly, and overall training progress with an intravaginal device of the invention and/or (ii) present, daily, weekly, monthly, and overall health status of her urogenital system and/or pelvic floor (e.g., the muscle fibers of the levator ani, e.g., the pubococcygeus, ileococcygeus, coccygeus, puborectalis muscles and associated connective tissues). In particular, the application is designed to guide, coach and motivate a user through positioning (e.g., orienting) the intravaginal device within her vagina (e.g., proximal to the cervix or vaginal cuff) and completing a training program including the performance of pelvic floor lifts (PFLs) and/or pelvic floor relaxations (PFRs). The application provides a step-by-step guide and real-time feedback (e.g., corrective instruction) on positioning the intravaginal device within the vagina and on the specific movements (e.g., pelvic floor muscle engagement and relaxation) which comprise a PFL and/or PFR.

The application may also provide feedback to an individual on how the performance of an everyday movement or activity (e.g., an index event) affects the health status of her urogenital system and/or pelvic floor (e.g., feedback based on data produced by one or more of the sensors in the device). The feedback provided by the application may be reviewed by the individual and/or a medical practitioner and/or a third party in substantially real-time or the feedback may be stored by the application, e.g., in the memory of the intravaginal device, a connected electronic device (e.g., a computer, tablet, and/or smartphone), or a database (e.g., a local database or a remote database, such as an internet-based database).

The application can include several screens: Welcome and/or Login, Calibration and Orientation, Dashboard, Training and Coaching, Live Mode, Menu, Introduction, Device, Exercise History, and Symptoms.

On first use of the application, the Welcome and/or Login screen can allow a user to establish a training account on the database where the user's training data (e.g., sensor data) will be stored. This step can include the registration of her intravaginal device and the creation of a username and password. The user can also elected to connect with a healthcare professional, who is overseeing her training, with whom they will share her training data.

The user may also be prompted to insert and calibrate her intravaginal device using the Calibration and Orientation screen. The Calibration and Orientation screen will coach the user through inserting and orienting the intravaginal device. The application may show the user a schematic diagram of the intravaginal device and prompt the user to identify the indicia on her own device that marks the device's top and front sides. The user may be asked to insert the device by hand or by using the insertion tool, such that the top indicia will be facing the top of the vagina and the front indicia will be facing the user's anterior. In real-time the application can provide the orientation of the intravaginal device on its x, y, and z-axis during the insertion step and will coach the user to orient the device parallel to the top of the vaginal canal and proximal to the cervix or vaginal cuff. When the correct orientation is obtained, the application can prompt the user to confirm that the indicia marking the front (e.g., anterior) side of the intravaginal device is facing the anterior side of her body. This orientation step could be conducted on insertion of the device. If the device is removed and subsequently replaced the orientation step may be repeated. Next, the application can coach the individual through performing a series of exercises, such as pelvic floor lifts (PFLs) and pelvic floor relaxations (PFRs), to establish a baseline of measurements from which the progress of the user of the intravaginal device can be determined over time. The calibration step can be repeated at any time chosen by the user.

The application may also include a Dashboard screen displaying the total power charge of the intravaginal device substantially in real-time, the total time the intravaginal device has been in place inside the user, the total number of PFLs and PFRs performed on a given day, a pH measurement (e.g., a pH measurement taken substantially in real-time and/or an average pH measurement for a given day and/or hour), a score related to the pelvic floor muscle quality of the user, and at least one score related to the overall progress of the user during the treatment period. The Dashboard may also provide a summary of data collected during the use of the optional Live Mode, which can be used for substantially real-time monitoring of the overall health status of a user's urogenital system and/or pelvic floor (e.g., the muscle fibers of the levator ani, e.g., the pubococcygeus, ileococcygeus, coccygeus, puborectalis muscles and associated connective tissues). The Dashboard may provide the total number of PFLs and PFRs that were performed, e.g., intentionally or unintentionally, by a user as they performed her daily activities, and a score related to the amount of stress that has been placed on the pelvic floor muscles during a time period in which Live Mode was active.

The overall progress score of the user can be calculated based on a set of baseline measurements obtained during the calibration session. The data collected during the calibration session can include, but is not limited to, maximum number of PFLs and/or PFRs performed until pelvic floor muscle exhaustion is reached (e.g., the user can no longer perform PFL and/or a PFR), maximum change in distance from the insertion position of the intravaginal device during a PFL and a PFR, a measurement of muscle quality and/or strength, and a pH measurement. During the calibration step, if a light detecting sensor, such as a LiDAR sensor, is included in the intravaginal device, reference (e.g., baseline) measurements can be collected on the three-dimensional (3D) structure of the pelvic floor and vaginal tissues, such that an initial (e.g., reference) 3D model of the user's pelvic floor and vaginal tissues can be generated. Additionally, if an electrical impedance myography (EIM) sensor is included in the intravaginal device, reference (e.g., baseline) values of the phase angle (θ), reactance (X), and/or resistance (R) can be obtained. The EIM reference levels measured by the intravaginal device may be used to calculate a reference score, e.g., a reference muscle quality score, which may be displayed to the user. A reference muscle quality score may be assigned to a particular muscle and/or tissue of the pelvic floor, or to the pelvic floor as a whole (e.g., an overall reference muscle quality score). An additional component of the calibration step may include the completion of a questionnaire designed to assign a symptom score reflective of the severity of the user's PFD. Additionally, if a hormone sensor is included in the intravaginal device, reference (e.g., baseline) values for at least one reproductive hormone (e.g., gonadotropin-releasing hormone (GnRH), follicle-stimulating hormone (FSH), lutenizing hormone (LH), estrogen, progesterone, human chorionic gonadotropin (HCG) and derivatives thereof) can be obtained. If a toxin sensor is included in the intravaginal device, a reference (e.g., baseline) values for a toxin (e.g., a bacterial toxin, a fungal toxin, a viral toxin, and/or a toxin produced by a parasite) may be compared to a predetermined level, such as a level known in the art or set by a medical practitioner. An overall progress score can be calculated from the calibration measurements alone or from the calibration measurements and the symptom score together. A score related to the overall health status of a user's urogenital system and/or pelvic floor may also be generated. Alternatively, the symptom score may also be displayed on the Dashboard.

If the device includes an EIM sensor, such as a SKULPT® sensor, a score (e.g., a muscle quality score) related to a user's phase angle (θ), reactance (X), and/or resistance (R) values, as compared to a reference level, can be displayed by the application on the user interface. Depending on the arrangement of the EIM sensors within the intravaginal device, particular muscles of the pelvic floor may be specifically identified with a muscle quality score. In some instances, an overall muscle quality score for the pelvic floor can be calculated.

If the device includes a light detecting sensor, such as a LiDAR sensor, the application may also display to the user on the user interface a 3D model of her pelvic floor and vaginal tissues. Specific scoring data (e.g., a muscle quality score), such as may be calculated from data collected by other sensors within the intravaginal device (e.g., a movement sensor, accelerometer, gyroscope, micro-electro-mechanical systems (MEMS) sensor, G-sensor, tilt sensor, and rotation sensor, EIM sensor, pressure sensor, muscle quality sensor, and/or pH sensor), can be displayed overlaid onto the 3D model to identify particular regions of the pelvic floor that need additional training (e.g., strengthening and/or relaxing). A 3D model of the patient's vaginal canal and pelvic floor tissues can be generated at any time during the treatment period and/or be generated substantially continuously.

The Dashboard display on the user interface can include an operative button for launching a Training and Coaching screen. The Training and Coaching screen can provide the user with real-time visual feedback on her performance of a PFL and/or a PFR. For example, the user can be coached through the performance of a particular series of PFLs and/or PFRs, such as a series including performing PFLs and/or PFRs over a set time interval (e.g., 1-5 minutes, 1-60 seconds, or 15 seconds) and a set time interval of rest (e.g., 1-5 minutes, 1-60 seconds, or 15 seconds). The user can be instructed to repeat the series one or more (e.g., 1, 2, 3, 4, or 5) times. A graph can be generated to indicate the strength of each PFL and/or a PFR performed by the user.

The Dashboard display on the user interface can include an operative button for launching a Live Mode screen. The Live Mode screen may present the user with the option of activating Live Mode (e.g., real-time monitoring) and allow the user to establish a preference setting that determines which sensors are actively collecting data during Live Mode and how feedback should be displayed to the user. The Dashboard may provide a summary of the information collected by the sensors in Live Mode.

The Introduction screen displayed by the application on the user interface provides educational material on PFDs and an explanation of how the intravaginal device can be used to treat PFDs. The Device screen displayed by the application on the user interface provides specific information on a user's intravaginal device. For example, this screen can provide information on the battery level (e.g., charge) of the intravaginal device and how long (e.g., how many days) the intravaginal device has been inside the user. The Exercise History screen displayed by the application on the user interface provides information on past training sessions performed by the user. The Symptoms screen displayed by the application on the user interface provides information for a user to track the symptoms of a PFD that they are experiencing on a given day, such as a form-based questionnaire (e.g., an optional daily survey and/or diary). The Menu screen displayed by the application on the user interface provides easy navigation to all other screens included in the software application.

The user interface may also include a function that allows the user to view charts showing her progress during treatment and during daily monitoring. The data shown using this charting function can be transmitted by the user to her healthcare provider or to a third party (e.g., automatically or by the user).

The user interface may also include a function that allows the user to deliver a pharmaceutical agent, e.g., by an intravaginal device of the invention, to tissue of the vagina. The user interface may allow the user to change, e.g., the dosage of a pharmaceutical agent and/or the frequency of dose administration by the intravaginal device. The user interface may also include a function that instructs the user on how to refill a delivery module, such as a reservoir, with pharmaceutical agent or how to apply a coating, layer, or gel to a surface of the intravaginal device. In some instances, the user interface may allow the user to alter how a pharmaceutical agent is delivered in response, e.g., to sensor data obtained by the intravaginal device. For example, a user or a medical practitioner may elect to have a pharmaceutical agent administered before, during, or after the performance of a pelvic floor exercise (e.g., a PFL and/or PFR). The user interface may also provide information to the user on the level or amount of the pharmaceutical agent remaining in the intravaginal device so that the user can replace the device or refill the pharmaceutical agent. The user interface can also include a function that allows the user to establish (e.g., set a preference) how an intravaginal device of the invention may deliver a pharmaceutical agent, as described herein, in response to a measurement obtained while the intravaginal device performs daily monitoring.

The user interface may also include a function to control the RF transmitters to deliver energy. For example, the power, frequency, and duration of energy transmission may be modulated by the user interface based on user preferences and physician recommendations. The intravaginal device may have temperature sensors that sense the temperature changes as a result of the RF transmitters. Upon sensing a temperature that is too high, it may communicate with the user interface to alert the user to lower the power, frequency, and/or duration of RF treatments. The device may also automatically turn the RF emitters up or down in response to a predetermined temperature threshold being or not being crossed.

III. Pelvic Floor Disorders (PFDs) that can be Treated with the Intravaginal Device Pelvic floor disorders (PFDs) that can be treated by the intravaginal device and the methods described herein include a wide range of conditions that occur when the muscles of the pelvic floor (PF) are weak (e.g., hypotonic), tight (e.g., hypertonic), or there is an impairment of or damage of the sacroiliac joint, lower back, coccyx, or hip joints. Neurogenic factors, including lumbosacral nerve damage, such as the nerve damage seen in multiple sclerosis and stroke patients, can also contribute to the development and progression of PFDs (National Clinical Guideline Centre (UK). *NICE Clinical Guidelines.* 148, 2012). Pelvic surgery (e.g., hysterectomy), vaginal childbirth, age, obesity, diabetes, connective tissue disorders, and genetic predisposition have also been identified as risk factors for the development of PFDs (Memon et al., *Womens Health (Lond. Engl.).* 9(3), 2013).

Symptoms of PFDs include changes to muscle tone, changes to muscle strength, bladder leakage, anal or fecal leakage, pain, frequency, and urgency. Exemplary PFDs include, but are not limited to, urinary incontinence (UI), stress urinary incontinence (SUI), urge incontinence, mixed stress and urge urinary incontinence, dysuria (e.g., painful urination), anal or fecal incontinence, pelvic organ prolapse (POP) (e.g., urethra prolapse (urethrocele), bladder prolapse (cystocele), or both urethra and bladder prolapse (cystourethrocele), vaginal vault and cervix prolapse (vaginal vault prolapse), uterus prolapse (uterine prolapse), rectum prolapse (rectocele), sigmoid colon prolapse (sigmoidocele), and small bowel prolapse (enterocele)), pelvic pain, sexual dysfunction (e.g., coital incontinence, a sexual pain disorder, dyspareunia, vaginismus, and/or impaired sexual arousal), weak or impaired pelvic floor muscle function, post-labor issues or damage, pain and/or incontinence caused by damage to a lumbosacral nerve, and nonrelaxing pelvic floor dysfunction.

a. Incontinence

Forms of urinary and anal or fecal incontinence that can be treated by pelvic floor muscle training (e.g., by the performance of a pelvic floor lift (PFL) using, e.g., the device and methods described herein include, but are not limited to, urinary incontinence (UI), stress urinary incontinence (SUI), urge incontinence, mixed stress and urge urinary incontinence, and anal or fecal incontinence.

The urethra is the canal leading from the bladder that discharges urine externally. In females, the urethra is a ~4 cm canal passing from the bladder, in close relation with the anterior wall of the vagina and having a long axis that parallels that of the vagina opening in the vestibule of the vagina posterior to the clitoris and anterior to the vaginal orifice. (See STEDMAN's MEDICAL DICTIONARY, at page 2072 ($28^{th}$ edition, 2005). The urinary bladder refers to a musculomembranous elastic bag serving as a storage place for the urine, filled via the ureters and drained via the urethra. The bladder neck is the smooth muscle of the bladder, which is distinct from the detrusor muscle. In females, the bladder neck consists of morphologically distinct smooth muscle. The large diameter fasciculi extend obliquely or longitudinally into the urethral wall. In a normal female, the bladder neck above the pelvic floor is supported predominantly by the pubovesical ligaments, the endopelvic fascia of the pelvic floor, and levator ani. These support the urethra at rest; with elevated intra-abdominal pressure, the levators contract increasing urethral closure pressure to maintain continence. This anatomical arrangement commonly alters after parturition and with increasing age, such that the bladder neck lies beneath the pelvic floor, particularly when the intra-abdominal pressure rises. This mechanism may fail to maintain continence, leading to incontinence as a result of urethral hypermobility, whereas a normal woman has no issues with any urinary or anal or fecal leakage.

Exercise using an intravaginal device of the invention, as described herein, can be used to strengthen the pelvic floor muscles, which can restore an anatomical arrangement that promotes continence.

b. Organ Prolapse

Pelvic organ prolapse (POP) that can be treated by pelvic floor muscle training (e.g., by the performance of a pelvic floor lift (PFL) and/or a pelvic floor relaxation (PFR)) using, e.g., the device and methods described herein include, but are not limited to, urethra (urethrocele), bladder (cystocele), or both urethra and bladder (cystourethrocele), vaginal vault and cervix (vaginal vault prolapse), uterus (uterine prolapse), rectum (rectocele), sigmoid colon (sigmoidocele), and small bowel (enterocele) prolapse. A detailed description of pelvic organ prolapse can be found at (www.acog.org/Resources-And-Publications/Practice-Bulletins/Committee-on-Practice-Bulletins-Gynecology/Pelvic-Organ-Prolapse), which is hereby incorporated by reference. A standardization of the terminology associated with POP is described in Bump et al. *American J. Obstet. Gynec.* 175.1 (1996): 10-17, which is hereby incorporated by reference.

In general, the various stages of POP are based on the maximal extent of prolapse relative to the hymen, in one or more compartments. A normal patient is considered stage 0 while stage I (least severe) to stage IV (most severe) are quantified by the distance of the prolapse as follows:

Stage 0: No prolapse; anterior and posterior points are all −3 cm.

Stage I: The criteria for stage 0 are not met, but the most distal portion of the prolapse is >1 cm above the level of the hymen.

Stage II: The most distal portion of the prolapse is ≤1 cm proximal to or distal to the plane of the hymen.

Stage III: The most distal portion of the prolapse is >1 cm below the plane of the hymen but protrudes no further than 2 cm less than the total vaginal length in cm.

Stage IV: Essentially, complete eversion of the total length of the lower genital tract is demonstrated. The distal portion of the prolapse protrudes to at least 2 cm. In most instances, the leading edge of stage IV prolapse will be the cervix or vaginal cuff scar.

A device of the invention may detect hypermobility of a woman's pelvic floor muscles (e.g., a woman with stage I, II, III, or IV POP (such as mild to severely symptomatic patients)). For example, sinusoidal-type curvature of the device may occur upon performing a lift exercise, suggesting that the musculature of the pelvic floor is too weak to constrain the device in a linear fashion. A woman with stage IV, or total prolapse, exhibits pelvic floor collapse and the inability to "raise" the device of the invention during a PFL exercise. Additionally, the device may be completely extruded from the vagina or urethra.

Other routine activities may increase abdominal pressure and cause pelvic floor damage. Examples of activities that can cause pelvic floor damage include, for example weightlifting (e.g., deadlifts, CrossFit® training), lifting heavy objects (e.g., children), running, chronic coughing, childbirth, and constipation. These activities can be monitored during use of an intravaginal device of the invention and the user can receive a signal warning them that the activities may negatively affect their pelvic floor health.

c. Sexual Dysfunction

Sexual dysfunction that can be treated by pelvic floor muscle training (e.g., by the performance of a pelvic floor relaxation (PFR)) using, e.g., the device and methods described herein, can be divided into two basic groups: (1) individuals with damage or weakness in a muscle of the pelvic floor (PF) (e.g., individuals having pelvic floor muscle hypotonus), and (2) individuals having high pelvic floor muscle tone (e.g., high contraction), pelvic floor muscle spasm, and/or pain (e.g., individuals having pelvic floor muscle hypertonus) (Rogers. *Can. Urol. Assoc. J.* 7:S199-S201, 2013; Bozkurt et al. *Taiwanese Journal of Obstetrics & Gynecology.* 53:452-458, 2014; Rosenbaum. *J. Sexual Med.* 4(1):4-13, 2007). Group 1 individuals may include, for example, individuals having urinary and/or anal or fecal incontinence, pelvic organ prolapse (POP), and coital incontinence. Group 2 individuals may include, for example, individuals having coital incontinence, a sexual pain disorder, dyspareunia, vaginismus, and/or impaired sexual arousal.

d. Neurological Disease or Injury

Pelvic floor disorders (PFDs) that can be treated by pelvic floor muscle training (e.g., by the performance of a pelvic floor lift (PFL) and/or a pelvic floor relaxation (PFR)) using e.g., the device and methods described herein, may occur in individuals experiencing neurological disease or injury, such as brain conditions, suprasacral spinal cord conditions, and sacral spinal cord or peripheral nerve conditions. For example, multiple sclerosis (MS) or stroke patients commonly experience a PFD and present with a variety of symptoms including urgency, urge incontinence, daytime frequency, nocturia, and nocturnal enuresis, involuntary leakage of urine, voiding frequency >8 per 24 hours, voiding dysfunction such as hesitancy, straining, poor stream, and incomplete emptying.

IV. Vaginal Conditions

The intravaginal device of the invention may be configured to administer energy from one or more energy transmitters, which may be used in therapeutic applications to treat a pelvic floor or vaginal disorder. Exemplary vaginal disorders are vaginal laxity, pelvic organ prolapse, incontinence, tissue tone (e.g., moisture and tightness), nerve sensitivity, orgasmic dysfunction, vulvovaginal laxity (e.g., in labial and vaginal tissues), atrophic vaginitis, stress incontinence, and pubocervical fascia tightening. The energy transmitters may be, for example, radio frequency transmitters, lasers, or electrical stimulators. RF transmitters provide nonablative radio frequency in the form of thermal energy to treat vaginal and pelvic floor disorders by heating tissue. By applying heat to the affected tissue, the thermal damage stimulates collagen production in deep layers of the skin and subcutaneous tissue to strengthen and fortify the collagen network in the vagina and surrounding area. This strengthens the tissues in areas critical for maintaining pelvic floor and vaginal health.

V. Drug Delivery

An intravaginal device of the invention may be configured to administer, e.g., locally or systemically, a pharmaceutical agent (e.g., a composition comprising a pharmaceutical agent) useful in the treatment of a pelvic floor disorder (PFD) such as, but not limited to, urinary incontinence (UI), stress urinary incontinence (SUI), urge incontinence, mixed stress and urge urinary incontinence, dysuria (e.g., painful urination), anal or fecal incontinence, pelvic organ prolapse (POP) (e.g., urethra prolapse (urethrocele), bladder prolapse (cystocele), or both urethra and bladder prolapse (cystourethrocele), vaginal vault and cervix prolapse (vaginal vault prolapse), uterus prolapse (uterine prolapse), rectum prolapse (rectocele), sigmoid colon prolapse (sigmoidocele), and small bowel prolapse (enterocele)), pelvic pain, sexual dysfunction (e.g., coital incontinence, a sexual pain disorder, dyspareunia, vaginismus, and/or impaired sexual arousal), weak or impaired pelvic floor muscle function, post-labor issues or damage, pain and/or incontinence caused by damage to a lumbosacral nerve, nonrelaxing pelvic floor dysfunction, and/or the symptoms thereof (e.g., changes to muscle tone, changes to muscle strength, bladder leakage, anal or fecal leakage, pain, frequency, and urgency), or another disease or condition affecting a female subject, e.g., as described herein).

Delivery of a pharmaceutical agent to the tissues of the vagina may be coordinated with the performance of a pelvic floor training exercise (e.g., a PFL or PFR), such that the pharmaceutical agent is delivered prior to, during, or after use of the intravaginal device to perform a pelvic floor exercise (e.g., a PFL or PFR). In some instances, administration of a pharmaceutical agent may be delivered by an intravaginal device of the invention that is configured to provide daily monitoring (e.g., in substantially real-time) in response to a measurement while a user performs her daily activities. Selection of a pharmaceutical agent to be incorporated into an intravaginal device of the invention may be made by, e.g., a medical practitioner, e.g., overseeing the treatment of an individual having a PFD or by the device user. The pharmaceutical agent may be one that is used to treat or ameliorate a PFD, or a symptom thereof. Alternatively, or in addition to, the intravaginal device may be configured to deliver a pharmaceutical agent suitable for the treatment a condition and/or disease of the vaginal tissues and/or female organs that, e.g., although unrelated to pelvic floor dysfunction, may be present in patients, such as those having a PFD. Non-limiting examples of such diseases and/or conditions include sexually transmitted diseases (STDs), yeast infections (e.g., candida vulvovaginitis), bacterial infections (e.g., bacterial vaginosis), parasitic infections (e.g., trichomoniasis), infection of the cervix (e.g., cervicitis), cancer (e.g., vaginal, vulva, cervical, ovarian, endometrial, and/or breast cancer), vaginitis (e.g., infectious and/or noninfectious vaginitis), endometriosis, vaginal pain, vulvar pain (e.g., vulvodynia), vulvar or vaginal injury, pudendal neuralgia, and vaginal skin conditions (e.g., vaginal dermatitis).

To treat a PFD and/or a condition of the vaginal tissue and female organs, or a symptom thereof, the intravaginal device may be inserted into the vaginal cavity and the pharmaceutical agent (e.g., a composition comprising a pharmaceutical agent) may be released and absorbed by the surrounding vaginal tissue, e.g., transdermally and/or transmucosally. In some instances, the pharmaceutical agent may be, e.g., uniformly dispersed or dissolved throughout the material of the intravaginal device (e.g., the material of the main body and/or tether). In some instances, the pharmaceutical agent may be confined to a delivery module or component (e.g., 1, 2, 3, 4, 5, 6, 7, 8, 9, 10 or more delivery modules or components), such as an inner core or reservoir arranged within the main body and/or tether of the intravaginal device. Non-limiting examples of delivery modules that may be incorporated into an intravaginal device of the invention are described in, e.g., Malcolm et al. (*Int. J. Women. Health.* 4:595-605, 2012); U.S. Publication Nos. US20090004246A1 and US20070043332A1; U.S. Pat. Nos. 6,394,094, 5,972,372, 8,333,983, 6,436,428, and 6,126,958, 3,991,760, 4,215,691, and 4,402,695; and International Publication Nos. WO200170154 and WO2012065073A2, each of which are herein incorporated by reference in their entirety. A pharmaceutical agent may also be applied to the surface of the intravaginal device (e.g., the main body and/or tether) as a coating, layer, or gel.

A pharmaceutical agent may be released from an intravaginal device of the invention, e.g., at a rate that does not change with time (zero-order release). During zero-order release a therapeutically effective dose is maintained by the delivery system, e.g., the intravaginal device comprising a delivery module. For example, sustained pharmaceutical agent delivery may be obtained with an intravaginal device of the invention that has been configured to contain a reservoir system, which consists of, e.g., tubes, fibers, laminates, or microspheres. In these systems, a reservoir may be coated in a rate-controlling membrane. Pharmaceutical agent diffusion across the membrane is rate limiting and is constant (zero order) as long as the membrane's permeability does not change and as long as the concentration of pharmaceutical agent in the reservoir is constant.

In another example, when a pharmaceutical agent is dispersed through a material (e.g., a polymeric material, e.g., a monolithic system) of the intravaginal device (e.g., the main body and/or tether), the pharmaceutical agent may be released as it diffuses through the material. In this example, the pharmaceutical agent is released from the outer surface of the material first. As this outer layer becomes depleted the pharmaceutical agent is released from further within the material. Because the pharmaceutical agent must also diffuse through the depleted material, the net result is that the release rate slows down producing a delayed release effect.

The configuration of the intravaginal device can be selected, e.g., by a medical practitioner, to suit the therapeutic needs of the individual patient, e.g., a patient having a PFD and suitable for treatment with an intravaginal device of the invention. Additionally, a plurality of design configurations may be combined so as to allow more than one pharmaceutical agent (e.g., 1, 2, 3, 4, 5, or more pharmaceutical agents) to be released according to established guidelines, e.g., at dosage amounts authorized by the FDA or other regulatory agency. An intravaginal device of the invention may contain a combination of a delivery module or component and a core of material containing a pharmaceutical agent for sustained or directed release. For example, the intravaginal device may be composed of a material in which a pharmaceutical agent is dispersed and also include at least one additional inner core or reservoir (e.g., 1, 2, 3, 4, 5, 6, 7, 8, 9, 10, or more additional inner cores or reservoirs) containing the pharmaceutical agent(s).

Use of an intravaginal device of the invention to administer a pharmaceutical agent may allow for nondaily, low dose, and continuous dosing with a pharmaceutical agent, which may result in, e.g., stable drug levels, a lower incidence of side effects, and/or improved patient compliance with a treatment regime, e.g., one provided by a medical practitioner, including administration of the pharmaceutical agent and/or a pelvic floor training exercise (e.g., a PFL or PFR).

Non-limiting examples of pharmaceutical agents, or combinations thereof, that can be administered using an intravaginal device of the invention are described below and may include those described. e.g., in, e.g., Drutz et al. ("Female Pelvic Medicine and Reconstructive Pelvic Surgery." Springer, London. 2003), Hussain et al. (*J. of Controlled Release.* 103:301-313, 2005), Santoro et al. ("Pelvic Floor Disorders: Imaging and Multidisciplinary Approach to Management." Springer, London. 2010), and U.S. Publication No. US20110045076A1, each of which are herein incorporated by reference in their entirety.

Anticholinergic (Antimuscarinic) Agents

Anticholinergic agents block the neurotransmitter acetylcholine in the central and the peripheral nervous system and may depress both voluntary and involuntary bladder contractions, thereby, e.g., suppressing involuntary bladder contraction. Anticholinergic agents are commonly used in the treatment of, e.g., urge urinary incontinence (UUI), overactive bladder syndrome (OAB), and nocturnal enuresis. In addition, they may increase the urine volume at which first involuntary bladder contraction occurs, decrease the amplitude of the involuntary bladder contraction, and increase bladder capacity. Non-limiting examples of anticholinergic agents that may be delivered to a subject in need of treatment for, e.g., involuntary bladder contraction using an intravaginal device of the invention include, e.g., atropine (e.g., ATROPEN®), scopolamine (e.g., TRANSDERM SCOP®), dicyclomine hydrochloride (e.g., BENTYL®), darifenacin (e.g., ENABLEX®), solifenacin succinate (e.g., VESICARE®), hyoscyamine sulfate (e.g., LEVSIN® and CYSTOSPAZ-M®), propantheline (e.g., PRO-BANTHINE®), tolterodine (e.g., DETROL® and DETROL LA®), propiverine (e.g., DETRUNORM®), trospium (e.g., SANCTURA®), fesoterodine (e.g., TOVIAZ®), bethanechol (e.g., URECHOLINE®), and carbachol (e.g., MIOSTAT® and CARBASTAT®).

Anticholinesterase Inhibitors

Acetylcholinesterase inhibitors inhibit the acetylcholinesterase enzyme from breaking down acetylcholine, thereby increasing both the level and duration of action of the neurotransmitter acetylcholine. Acetylcholinesterase inhibitors have been used to treat, e.g., overflow incontinence. A non-limiting example of an acetylcholinesterase inhibitor that may be delivered to a subject in need of treatment for, e.g., overflow incontinence using an intravaginal device of the invention is distigmine.

Alpha-Adrenergic Agonists

Alpha-adrenergic agonists (e.g., α1 and α2 agonists) selectively stimulate alpha-adrenergic receptors (e.g., α1 and α2 receptors) and may be useful, e.g., in increasing bladder outlet resistance by contracting the bladder neck, and may be delivered to a subject in the treatment of, e.g., mild to moderately severe stress urinary incontinence (SUI) using an intravaginal device of the invention. Non-limiting examples of alpha-adrenergic agonists that may be delivered with an intravaginal device of the invention include, e.g., midodrine (e.g., AMATINE®, PROAMATINE®, and GUTRON®), pseudoephedrine hydrochloride (e.g., SUDAFED®), phenylpropanolamine, ephedrine, and norephedrine.

Alpha-Adrenergic Antagonists

Alpha-adrenergic antagonists (e.g., alpha-blockers, such as α1- and α2-blockers) act as neutral antagonists or inverse agonists of alpha-adrenergic receptors (e.g., α1 and α2 receptors) and have been used, e.g., to treat UUI and OAB. They have shown some success, e.g., in patients who have decentralized or autonomous bladders as the result of myelodysplasia, spinal cord injury, or radical pelvic surgery. Non-limiting examples of alpha-adrenergic antagonists that may be delivered with an intravaginal device of the invention to a subject in need of treatment for, e.g., UUI and/or OAB, include phenoxybenzamine (e.g., DIBENZYLINE®), prazosin (e.g., MINIPRESS®), alfuzosin (e.g., UROXATRAL®), doxazosin (e.g., CARDURA®), terazosin (e.g., HYTRIN®), and tamsulosin (e.g., FLOMAX®).

Beta-Adrenergic Agonists

Beta-adrenergic agonists act upon the beta adrenoceptors (e.g., β1- and β2-receptors), e.g., to increase intraurethral pressure and to treat SUI, UUI, and OAB. Non-limiting examples of beta-adrenoceptor agonists that may be delivered with an intravaginal device of the invention to a subject in need of treatment for, e.g., SUI, UUI, and/or OAB, include terbutaline (e.g., BRETHINE®, BRICANYL®, and BRETHAIRE®), clenbuterol (e.g., SPIROPENT® and VENTIPULMIN®), and salbutamol (e.g., VENTOLIN®)

Antispasmodic Agents

Antispasmodic agents, e.g., relax the smooth muscles of the urinary bladder. By exerting a direct spasmolytic action on the smooth muscle of the bladder, these medications have been reported to, e.g., increase bladder capacity and effectively decrease or eliminate urge incontinence. Non-limiting examples of antispasmodic agents that may be delivered with an intravaginal device of the invention to a subject in need of treatment for, e.g, to increase bladder capacity and/or to decrease or eliminate urge incontinence, include, e.g., calcium antagonists, potassium channel openers, oxybutynin chloride (e.g., DITROPAN® IR, DITROPAN XL®, and GELNIQUE®), flavoxate (e.g., URISPAS®), emepronium bromide (e.g., CETIPRIN®), imidafenacin (e.g., URITOS®), meladrazine, mirabegron (e.g., MYRBETRIQ®), and terodiline.

Antidepressants

Tricyclic antidepressants (TCAs) have been traditionally used to treat major depression, however, TCAs have an additional use in the treatment of bladder dysfunction, e.g., SUI. TCAs function to increase norepinephrine and serotonin levels and may exhibit, e.g., an anticholinergic and direct muscle relaxant effect on the bladder. Non-limiting examples of TCAs that may be delivered with an intravaginal device of the invention to a subject in need of treatment for, e.g, SUI, include, e.g., imipramine hydrochloride (e.g., TOFRANIL®) and amitriptyline hydrochloride (e.g., ELAVIL®). Other antidepressants, such as serotonin/norepinephrine reuptake inhibitors may also improve, e.g., stress incontinence. Non-limiting examples of serotonin/norepinephrine reuptake inhibitors that may be delivered with an intravaginal device of the invention to a subject in need of treatment for, e.g, stress incontinence, include, e.g., duloxetine (e.g., CYMBALTA®).

Hormones

Hormones such as estrogens, progestogens, testosterone, post-menopausal hormones, and derivatives thereof may be delivered with an intravaginal device of the invention. Treatment with hormones may serve, e.g., to nourish and strengthen the tissues of the pelvic floor. For example, estrogens may be able to increase urethral closure pressure, improve the transmission of abdominal pressure to the proximal urethra, and increase the sensitivity threshold of the bladder. Estrogens have been used, e.g., to treat SUI, in combination with other drugs, such as alpha-adrenergic agonists.

Non-limiting examples of estrogens that may be delivered with an intravaginal device of the invention to a subject in need of treatment for, e.g, SUI and/or to increase urethral closure pressure, improve the transmission of abdominal pressure to the proximal urethra, and/or to increase the sensitivity threshold of the bladder include, e.g., conjugated estrogen (e.g., PREMARIN®), estradiol, estrone, estriol, 17α-estradiol, 4-hydroxyestradiol, 2-hydroxyestradiol, estrone 3-sulfate, moxestrol, diethylstilbestrol, hexestrol, dienestrol, tamoxifen, 4-hydroxytamoxifen, clomifene, nafoxidine, ICI-164384, 5-androstenediol, 4-androstenediol, 3β-androstanediol, 3α-androstanediol, dehydroepiandrosterone, 4-androstenedione, coumestrol, genistein, β-zearalanol, and bisphenol A.

Non-limiting examples of progestogens that may be delivered with an intravaginal device of the invention to a subject in need of treatment for, e.g, SUI and/or to increase urethral closure pressure, improve the transmission of abdominal pressure to the proximal urethra, and/or to increase the sensitivity threshold of the bladder include, e.g., progesterone, dydrogesterone, chlormadinone acetate, cyproterone acetate, megestrol acetate, medroxyprogesterone, medrogestone, demegestone, nomegestrol acetate, promegestone, trimegestone, segesterone acetate, norethisterone, norethisterone acetate, lynestrenol, noretynodrel, levonorgestrel, norgestimate, desogestrel, etonogestrel, gestodene, dienogest, tibolone, and drospirenone.

Prostaglandin Synthesis Inhibitors

Prostaglandin synthesis inhibitors are agents that prevent the production of prostaglandins, which may cause contraction of the bladder, e.g., by inhibition of the cyclooxygenase (COX) enzymes. Prostaglandin synthesis inhibitors have been used, e.g., to treat UUI and OAB. Non-limiting examples of prostaglandin synthesis inhibitors that may be delivered with an intravaginal device of the invention to a subject in need of treatment for, e.g, UUI and/or OAB, include, e.g., nonsteroidal anti-inflammatory agents (NSAIDs) (e.g., salicylates, propionic acid derivatives, acetic acid derivatives, enolic acid derivatives, anthranilic acid derivatives, selective COX-2 inhibitors, and sulfonanailides) and steroidal anti-inflammatory agents. For example, the NSAID may be selected from indomethacin (e.g., INDOCIN® and TIVORBEX®), flurbiprofen (e.g., OCUFEN®), aspirin, celecoxib (CELEBREX®), diclofenac (CATAFLAM®, ZIPSOR®, ZORVOLEX®), diflunisal, etodolac, ibuprofen (MOTRIN®, ADVIL®), indomethacin (INDOCIN®), ketoprofen, ketorolac, nabumetone, naproxen (ALEVE®), oxaprozin (DAYPRO®), piroxicam (FELDENE®), salsalate, sulindac, and tolmetin Vasopressin Analogues Vasopressin analogues are similar in function but not necessarily similar in structure to vasopressin (ADH) and have been used, e.g., to reduce detrusor over-activity in the treatment of OAB. A non-limiting example of a vasopressin analogue that may be delivered with an intravaginal device of the invention to a subject in need of treatment for, e.g., OAR includes, e.g., desmopressin (e.g., DDAVP®).

Botulinum Toxins

Botulinum toxin is a neurotoxic protein produced by the bacterium *Clostridium botulinum* and is used to treat a number of disorders characterized by overactive muscle movement, e.g., OAB. For example, injections with botulinum toxin have been shown to decrease episodes of urinary leakage, reduce bladder voiding pressures, and post-void residual urgency. Non-limiting examples of botulinum toxins that may be delivered with an intravaginal device of the invention to a subject in need of treatment for, e.g, OAB, include, e.g., botulinum toxin A (e.g., BOTOX®) and botulinum toxin B (e.g., MYOBLOC®).

Muscle Relaxants

Non-limiting examples of muscle relaxants that may be used to treat a patient with, e.g., pelvic floor pain, high pelvic floor muscle tone and/or muscles spasms, may be delivered with an intravaginal device of the invention include, e.g., baclofen (e.g., LIORESAL®), chlorzoxazone (e.g., LORZONE®), carisoprodol (e.g., Soma®), cyclobenzaprine (e.g. AMRIX®), dantrolene (e.g., DANTRIUM® and RYANODEX®), diazepam (e.g., VALIUM®), metaxalone (e.g., SKELAXIN®), methocarbamol (e.g. ROBAXIN®), and tizanidine (e.g., ZANAFLEX®).

Agents that Stimulate Muscles and/or Prevent Muscle Mass Loss

Non-limiting examples of agents that stimulate muscles and/or prevent muscle mass loss that may be delivered, e.g., to aging patients, to treat, e.g., a PFD including muscle atrophy, with an intravaginal device of the invention include, e.g., β-hydroxy β-methylbutyrate (HMB), amino acids (e.g., such as lysine and the branched chain amino acids (BCAAs) leucine, isoleucine, and valine), anabolic steroids (e.g., methandrostenolone), and selective androgen receptor modulators (SARMs).

Other Pharmaceutical Agents

In addition to delivering pharmaceutical agents useful in the treatment of a PFD, or a symptom thereof, an intravaginal device of the invention may be configured to deliver a pharmaceutical agent useful in the treatment of an additional disease or condition that may be present in an individual having a PFD. In some instances, an individual identified as having a PFD suitable for treatment with an intravaginal device of the invention may already be using a vaginal device (e.g., a contraceptive or hormone replacement device), pessary, or suppository to administer a pharmaceutical agent to treat an additional disease or condition. In some instances, the additional disease or condition is identified after the individual has begun treatment for a PFD with an intravaginal device of the invention. To improve patient compliance with treatment for a PFD using an intravaginal device of the invention, the intravaginal device may be configured to deliver a pharmaceutical agent used to treat the additional disease or condition, e.g., to reduce the occurrence of the intravaginal device being removed during treatment for the secondary disease or condition and not reinserted. Additionally, an intravaginal device of the invention may be configured to deliver a pharmaceutical agent, e.g., a contraceptive agent, to substitute a contraceptive device that could not be worn during treatment for a PFD with an intravaginal device of the invention.

Non-limiting examples of other agents that may be delivered with an intravaginal device of the invention to treat an additional disease or condition, e.g., such as those described herein, include, e.g., microbicides (e.g., to reduce the infectivity of microbes, such as viruses or bacteria); hormone replacement and/or contraceptive agents (e.g., a estrogenic compound, a progestational compound, and/or a gonadotropin releasing hormone); estrogen receptor modulators (e.g., to treat vaginal atrophy and/or dyspareunia), antiviral agents (e.g., to treat sexually transmitted diseases, such as HIV), antibacterial agents (e.g., to treat bacterial vaginosis), anticancer agents (e.g., to treat endometrial, ovarian, cervical, vulvar, vaginal, or fallopian tube cancer), therapeutic peptides and proteins (e.g., to treat vaginal infections), benzodiazepines (e.g., to treat interstitial cystitis (IC)), and analgesics (e.g., to treat pain associated with a PFD and/or a cancer).

Formulation

Also featured are methods for treating a pelvic floor disorder (PFD), or the symptoms thereof, that include the administration of at least one pharmaceutical agent (e.g., 1, 2, 3, 4, 5, or more pharmaceutical agents) to vaginal tissue of an individual by an intravaginal device of the invention. For delivery of a pharmaceutical agent useful in the treatment of a PFD, the pharmaceutical agent may be formulated, e.g., as a composition, with a pharmaceutically acceptable diluent, excipient, carrier, or adjuvant that is compatible with a method of delivery using an intravaginal device of the invention. Suitable pharmaceutically acceptable diluents, excipients, carriers, and adjuvants are known in the art and may include, but are not limited to, ion exchangers, alumina, aluminum stearate, lecithin, self-emulsifying drug delivery systems (SEDDS) such as da-tocopherol polyethyleneglycol 1000 succinate, surfactants used in pharmaceutical dosage forms, such as TWEEN® surfactants or other similar polymeric delivery matrices, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat. Other formulations may include time-release, delayed release, or sustained release formulations, which may be incorporated into an intravaginal device of the invention.

The pharmaceutical agent may be dissolved or dispersed in the pharmaceutically acceptable diluent, excipient, carrier, or adjuvant as a powder, a liquid, in microcapsules, in nanoparticles, or any other form for being delivered by an intravaginal device of the invention transdermally and/or transmucosally to the vaginal tissues. In some instances, the pharmaceutical agent is mixed with a substance that facilitates, e.g., the delivery and/or absorption of the pharmaceutical agent by the vaginal tissues, such a moisturizing agent and/or an emollient component. A moisturizing and/or emollient component may include oil-in-water emulsions, water-in-oil emulsions, water-soluble lubricants, emulsions including cetyl alcohol, silicone-derivatives, grape seed oil, dimethicone, argan oil, jojoba oil, palm oil, olive oil, or combinations thereof. Additionally or alternatively to including moisturizers, the composition may include an element for stimulating fluid production. Elements for stimulating fluid production include, but are not limited to, estrogen, progesterone, or ospemifene. In some instances, the pharmaceutical composition may include a compound that enhances absorption or penetration of the pharmaceutical agent. Absorption enhancing compounds include compounds that enhance skin permeation, such as, by altering the stratum corneum lipids and/or proteins, or by increasing partitioning of the pharmaceutical agent into the stratum corneum. Examples of absorption enhancing compounds include, but are not limited to, oleic acids or non-ionic surfactants.

Dosages

The dose of a pharmaceutical agent(s), such as those described herein, and the duration of treatment (e.g., about 1-week, 2-weeks, 3-weeks, 4-weeks, 2-months, or 3-months, e.g., about 7-21 days, 7-35 days, 7-49 days, 7-63 days, 7-77 days, 7-91 days, or 7-105 days, e.g., about 2-8 weeks) with an intravaginal device of the invention may be increased or decreased based on the severity of, occurrence of, or progression of a pelvic floor disorder (PFD) in the subject (e.g., based on the severity of one or more symptoms of the PFD or other disease or condition to be treated).

The pharmaceutical agents described herein can be administered in a therapeutically effective amount by an intravaginal device of the invention to treat a PFD and/or to provide a reduction in the severity of at least one symptom associated with a PFD. In some instances, a pharmaceutical agent may be administered, e.g., in a dose according to guidelines known in the art and/or determined by a medical practitioner for the selected pharmaceutical agent(s). In some instances, a pharmaceutical agent described herein may be administered in a dose of about 1 μg to about 10 mg per day (e.g., at least 10 μg, 20 μg, 30 μg, 40 μg, 50 μg, 60 μg, 70 μg, 80 μg, 90 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1 mg, 2 mg, 3 mg, 4 mg, 5 mg, 6 mg, 7 mg, 8 mg, or 9 mg or more per day). The dosage administered, e.g., by an intravaginal device of the invention, can vary depending on, e.g., the subject to be treated, the pharmaceutical agent administered, the form of administration (e.g., as a solid or liquid), and the severity of the PFD, or the symptoms thereof, being treated to control the rate of pharmaceutical agent release and/or to enable the delivery (e.g., simultaneous and/or consecutive delivery) of more than one pharmaceutical agent (e.g., 1, 2, 3, 4, 5, or more pharmaceutical agents). The dosage of the pharmaceutical agent can also be established as an amount authorized by the FDA or other regulatory agency.

VI. Devices of the Invention

Figure 2A:
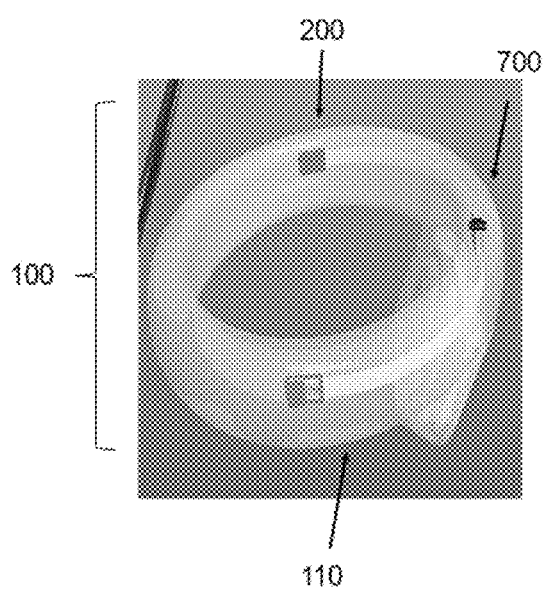
FIG. 2A is a schematic drawing showing intravaginal device 100 with main body 110, sensor 200 (e.g., an accelerometer, such as a MEMS sensor), and circuit board 700.
Figure 2B:
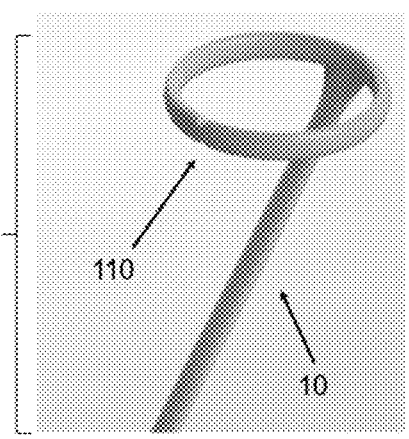
FIG. 2B is a schematic drawing showing intravaginal device 100 with main body 110 and tether 10.

A device of the invention that can be used to diagnose, monitor, or treat a pelvic floor disorder (PFD) or vaginal disorder is depicted in FIGS. 1-3. FIG. 1 depicts intravaginal device 100 with main body 110 and tether 10. Tether 10 may contain, for example, 1-20 sensors 200 (e.g., 1, 2, 3, 4, 5, 6, 7, 8, 9, 10, 11, 12, 13, 14, 15, 16, 17, 18, 19, 20 or more sensors 200). Main body 110 may also contain, for example, 1-20 sensors 200 (e.g., 1, 2, 3, 4, 5, 6, 7, 8, 9, 10, 11, 12, 13, 14, 15, 16, 17, 18, 19, 20 or more sensors) and 1-20 (e.g., 1, 2, 3, 4, 5, 6, 7, 8, 9, 10, 11, 12, 13, 14, 15, 16, 17, 18, 19, 20 or more) energy transmitters 210 (e.g., RF, laser, electrical stimulation). Tether 10 or main body 110 may be flat or oblong. The sensors in tether 10 may be MEMS sensors. Tether 10 may also contain a Bluetooth chip and/or an Apple chip or other wireless compatible chipset. Main body 110 may be configured to administer at least one (e.g., 1, 2, 3, 4, 5, or more) pharmaceutical agent to the vaginal tissues for the treatment of a PFD, a vaginal disorder, or the symptoms thereof, or other disease or condition. In some instances, tether 10 may be similarly configured to administer a pharmaceutical agent to the vaginal tissues. Configuring tether 10, which may be detachable from main body 110, for pharmaceutical administration would provide the user the option of being able to replace and/or exchange the tether as needed, e.g., when the pharmaceutical agent has been depleted, when a different pharmaceutical agent is required, or when a different dosage is required, without the need to discard main body 110. Tether 10 may have gradations or ruler markings to visualize how deep intravaginal device 100 is within the vagina (FIG. 21).

Intravaginal device 100 contains at least one sensor 200 within tether 10 for monitoring pelvic floor muscle movement. As depicted in FIG. 1, intravaginal device 100 contains circuit board 700 within main body 110. Circuit board 700 can be a flexible circuit board that connects multiple components of intravaginal device 100 to each other, such as sensor 200, battery 800, microcontroller 900, transmitter/receiver 1000, data storage unit 1100, sensory output component 1200, wireless communication antennae 1300, ON/OFF switch 1600, and authentication chip 1400 (FIG. 1, inset). Circuit board 700 can alternatively be connected to sensor 200 by a wire. Circuit board 700 and all its connected components may alternatively be positioned in tether 10. Intravaginal device 100 may be configured with additional sensors and/or delivery modules.

Intravaginal device 100 can be inserted into a subject and deployed at a position in proximity to the cervix, vaginal fornix, or vaginal cuff, substantially parallel to the surface of the upper vagina adjacent to the pelvic floor, manually or by using insertion tool 600. Intravaginal device 100 may also contain molded wing 300 for stabilizing the device at a position in proximity to the cervix or vaginal cuff of a patient (FIG. 1). Tether 10 may also be in the form of a detachable cable that can be used to connect intravaginal device 100 to transmitter/receiver box 500 and to assist in the removal of intravaginal device 100 from a patient.

Figure 5:
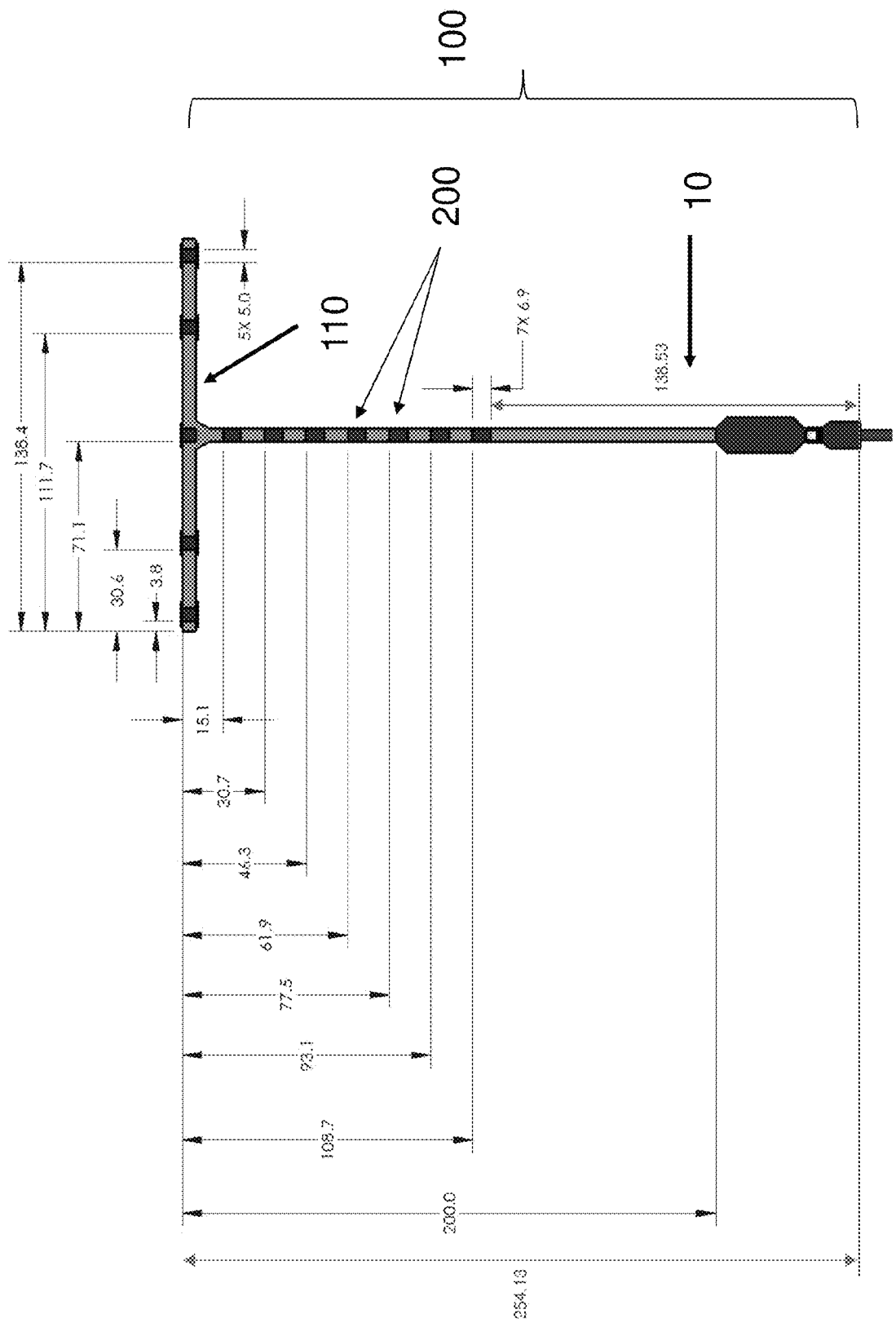
FIG. 5 is a schematic drawing of a flat projection of an embodiment of intravaginal device 100. For the purposes of illustration, main body 110 has been opened by means of a cut between sensors A9 and A12 (FIG. 4B), and displays its 5 sensors 200. Tether 10 in this illustration contains 9 sensors 200, though it can contain more or fewer. Although not shown, tether 10 may be configured to be detached from main body 110. In addition, tether 10 may end after the final sensor. As shown in this embodiment, intravaginal device 100, including both main body 110 and tether 10, is 25.5 cm from top to bottom and each sensor 200 is spaced 1.56 cm apart. This embodiment is an example only and is not intended to be limiting. The sensors depicted are, e.g., accelerometers, such as MEMS sensors, but other sensors can replace those shown or could be added within main body 110 and tether 10.

Transmitter/receiver box 500 and/or transmitter/receiver 1000 connects wirelessly to electronic device 1500, via a Wi-Fi and/or Bluetooth connection In certain embodiments, intravaginal device 10 contains 8 or fewer (e.g., 4 or 5) sensors 200 in tether 10 and 5 or fewer sensors 200 in main body 110. One sensor may be shared by both the tether and main body (FIG. 3). The angle between the plane connecting the anterior and posterior aspects of the main body 110 and tether 10 may vary from 0°-180° (e.g., 10°, 20°, 30°, 40°, 50°, 60°, 70°, 80°, 90°, 100°, 110°, 120°, 130°, 140°, 150°, 160°, 170°, 180°. The circumference of main body 110 may be from about 10 cm to about 50 cm (e.g., 15 cm, 20 cm, 25 cm, 30 cm, 35 cm, 40 cm, 45 cm, or 50 cm) or may be 27.6 cm. The length of tether 10 may be from about 3 cm to about 50 cm (e.g., 5 cm, 10 cm, 15 cm, 20 cm, 25 cm, 30 cm, 35 cm, 40 cm, 45 cm) or may be 25.5 cm long (FIG. 5). The sensors 200 may be spaced about 0.5 cm to about 5 cm (e.g., 1 cm, 1.5 cm, 2 cm, 2.5 cm, 3 cm, 3.5 cm, 4 cm, 4.5 cm) or may be spaced about 1.6 cm apart. At least one sensor 200 may be placed on tether 10 cm or less (e.g., 9 cm, 8 cm, 7 cm, 6 cm, 5 cm, 4 cm, 3 cm, 2 cm, or 1 cm) from main body 110.

The tether may be configured as a separable tether with one or more components (see, e.g., FIGS. 26-27). Having a separable tether allows the device to have a long-term wearable portion (e.g., ring 110 and part of tether 10; e.g., long-term wearable device 105) and a short-term wearable portion (e.g., short-term wearable portion 115) that can connect to a power supply for powering or recharging a local battery. This can be used for powering an intravaginal device with an RF transmitter(s) for therapeutic applications. RF transmitters may require power in the range of 10 mW to 300 W. Thus, in the event that a wireless power source (e.g., a battery) cannot sustain this power for an extended duration, the separable portion(s) of the tether can be configured for connection to a power source (e.g., an AC power source) to recharge the device or directly power the RF transmitter(s). The separable tether allows flexibility and modularity by permitting the intravaginal device to be used in either short-term (e.g., 1-30 minutes) or long term (e.g., 30 minutes or longer, e.g., 1 day-6 months) capacities.

If configured to be separation, the portions of the tether may further include connections, such as magnetic or interlocking connections (e.g., press fit, snap fit) that can be used to join the portion(s). The connections may also be configured to be electrical connections that can be used to supply power to the intravaginal device.

VII. Additional Device(s) that may be Used in Conjunction with an Intravaginal Device of the Invention An intravaginal device of the invention may be used (e.g., simultaneously and/or consecutively) with an additional device that is configured to treat a PFD and/or another disease or condition. Non-limiting examples of additional devices that may be used in combination with an intravaginal device of the invention include, but are not limited to, a vaginal pessary, a vaginal and/or anal suppository, a catheter (e.g., a urethral and/or rectal catheter, such as a device described in U.S. Publication No. US20150112231A1 and in International Publication Nos. WO2011050252A1 and WO2013082006A, each of which is herein incorporated by reference in their entirety), a bladder neck support device, a vaginal sponge, a menstrual device (e.g., a tampon or a menstrual cup), a vaginal stimulator (e.g., a device that contains one or more (e.g., 1, 2, 3, 4, 5, 6, 7, 8, 9, or 10 electrodes; a device that contains a vibrator; and/or a device that contains a light emitting source), a vaginal dilator, a vaginal specula, a urine seal, a urethral insert, an artificial urinary and/or anal sphincter, and/or a device that contains a camera.

VIII. Kits

Also featured are kits containing an intravaginal device for use in the prevention and treatment of pelvic floor disorders (PFDs). Such kits can be used to treat an individual (e.g., a female patient) who may benefit from pelvic floor muscle training (PFMT) that includes the performance of pelvic floor lifts (PFLs) and/or pelvic floor relaxations (PFRs). In some instances, the kit may include an intravaginal device of the invention that is configured to monitor the overall health status of a user's urogenital system and/or pelvic floor (e.g., the muscle fibers of the levator ani, e.g., the pubococcygeus, ileococcygeus, coccygeus, puborectalis muscles and associated connective tissues). A kit for treating or reducing the progression of a pelvic floor disorder in an individual may include an intravaginal device of the invention and one or more of a transmitter and receiver, a detachable cable, a tool for insertion of the intravaginal device, an electronic device, a database, and/or a user interface, a power source (e.g., one or more batteries), and instruction for use thereof. The kit may also include a variety of separable tether portions or modules and/or sleeves, e.g., one or more tether modules or separable tether portions and/or sleeves that each may include a sensor and/or a delivery module, as described herein, that may be used to expand the functionality of the intravaginal device. Additionally, the kit may contain an additional device, as described herein, a charger, a sanitary cleaner, and/or gloves.

Other optional components of the kit include a lubricant (e.g., a lubricant compatible with the material from which the intravaginal device is fabricated, e.g., silicone) for use in inserting the intravaginal device and/or a biomaterial (e.g., hyaluronic acid) for use in improving the adhesion of the intravaginal device at a position proximal to the cervix or vaginal cuff of an individual. The optional components (e.g., the lubricant and/or biomaterial) may be provided in a separate container (e.g., a sealed packet, tube, and/or applicator).

Additionally, a pharmaceutical agent useful in treating a PFD, or the symptoms thereof, or other disease or condition, as described herein, may also be supplied with a kit of the invention. The pharmaceutical agent may be supplied in any format (e.g., within a tube, vial, or pre-filled syringe) and with the necessary accessories (e.g., a needle, syringe, dropper, and/or brush) required to, e.g., fill or refill a delivery module or, e.g., to apply a coating, layer, or gel to the intravaginal device.

Alternatively, the optional components (e.g., the lubricant and/or biomaterial) can be provided pre-applied to the intravaginal device, such that the intravaginal device is ready for insertion and use. Additional optional components of the kit include sterile gloves (e.g., at least one pair) for use in the insertion and/or removal of the intravaginal device, or alternatively for use during the application of the lubricant and/or biomaterial to the intravaginal device, and/or a storage container for the intravaginal device and/or the system of the invention.

A kit of the invention may be useful in the treatment of a pelvic floor disorder such as, but not limited to, urinary incontinence (UI), stress urinary incontinence (SUI), urge incontinence, mixed stress and urge urinary incontinence, dysuria (e.g., painful urination), anal or fecal incontinence, pelvic organ prolapse (POP) (e.g., urethra prolapse (urethrocele), bladder prolapse (cystocele), or both urethra and bladder prolapse (cystourethrocele), vaginal vault and cervix prolapse (vaginal vault prolapse), uterus prolapse (uterine prolapse), rectum prolapse (rectocele), sigmoid colon prolapse (sigmoidocele), and small bowel prolapse (enterocele)), pelvic pain, sexual dysfunction (e.g., coital incontinence, a sexual pain disorder, dyspareunia, vaginismus, and/or impaired sexual arousal), weak or impaired pelvic floor muscle function, post-labor issues or damage, pain and/or incontinence caused by damage to a lumbosacral nerve, and nonrelaxing pelvic floor dysfunction.

IX. Methods of Use

Methods of Treating a Pelvic Floor or Vaginal Disorder with an Intravaginal Device of the Invention A female patient can use a device of the invention to perform pelvic floor lifts (PFLs) and/or pelvic floor relaxations (PFRs) in order to treat, inhibit, or reduce the development of or progression of a pelvic floor disorder (PFD). A female device can also use the device to treat other vaginal disorders as described herein. The device can be inserted into the vagina of the individual and the engagement of or relaxation of a pelvic floor (PF) muscle (e.g., the levator ani (e.g., the pubococcygeus, ileococcygeus, coccygeus, and puborectalis muscles) and the associated connective tissues which spans a spheric form from the pubic bone anteriorly to the sacrum posteriorly and to the adjoining bony structure joining these two bones) of the individual can be monitored with the intravaginal device. Treatment with the device reduces the frequency of occurrence and/or severity of at least one (e.g., 1, 2, 3, 4, 5, 6, 7, 8, 9, 10, or more) symptom of a pelvic floor disorder. In particular, treatment includes activating of the pelvic floor muscles and measuring the performance of a pelvic floor lift (PFL), which is an exercise characterized by an upward movement (e.g., a lifting movement, e.g., a movement in the cranial direction) of the pelvic floor and/or measuring the performance of a pelvic floor relaxations (PFR) (e.g., a downward movement, e.g., a movement in the caudal direction) of the pelvic floor using the device. In some instances, treatment includes using an intravaginal device of the invention that is configured to monitor (e.g., in substantially real-time) the overall health status of a user's urogenital system and/or pelvic floor (e.g., the muscle fibers of the levator ani, e.g., the pubococcygeus, ileococcygeus, coccygeus, puborectalis muscles and associated connective tissues). The device can be used to measure at least one (e.g., 1, 2, 3, 4, 5, 6, 7, 8, 9, or 10) or more performance metrics and/or at least one (e.g., 1, 2, 3, 4, 5, 6, 7, 8, 9, or 10) or more characteristic of an individual's pelvic floor disorder (PFD) including, but are not limited to, pressure (e.g., muscle contraction), temperature, pH, and muscle quality. The device can also be used to deliver therapeutic energy (e.g., with an RF transmitter) to promote healing of damaged vaginal tissue.

A patient can use the intravaginal device of the invention to treat a vaginal disorder or PFD over a treatment period ranging from about one week to about three months (e.g., about 1-week, 2-weeks, 3-weeks, 4-weeks, 2-months, or 3-months, e.g., about 7-21 days, 7-35 days, 7-49 days, 7-63 days, 7-77 days, 7-91 days, or 7-105 days, e.g., about 2-8 weeks). The intravaginal device can remain inside the patient during the treatment period to monitor the patient's pelvic floor muscles (e.g., muscle quality, muscle tone, pH) and the performance of PFLs and/or PFRs. The patient can also remove the device during the treatment period and can reinsert the device after disinfection (e.g., washing) to reinitiate treatment. The intravaginal device can monitor and collect data from its sensor(s) (e.g., at least one sensor, e.g., 1, 2, 3, 4, 5, 6, 7, 8, 9, 10, or more sensors) substantially continuously or periodically. The sensors can measure at least one (e.g., 1, 2, 3, 4, 5, 6, 7, 8, 9, or 10) or more performance metrics (e.g., the quality and/or quantity of PFLs and/or PFRs performed) and/or at least one (e.g., 1, 2, 3, 4, 5, 6, 7, 8, 9, or 10) or more characteristic of an individual's PFD (e.g., muscle quality and muscle tone). In some instances, the monitoring (e.g., monitoring of pelvic floor movement, of a performance metric, and/or characteristic of an individual's PFD) can occur after the intravaginal device has received a signal (e.g., a command) from the individual using the intravaginal device to begin collecting data. This signal may be a signal from a button (e.g., a button within a software application running on an electronic device wirelessly connected to the intravaginal device) which is pressed by the individual prior to performing a series of PFLs and/or PFRs with the intravaginal device.

The treatment program can include performing a series of one (e.g., 1, 2, 3, 4, 5, 6, 7, 8, 9, 10, 20, 30, 40, 50, 60, or 70) or more therapeutic energy treatment regimens, PFLs and/or PFRs (e.g., engaging the pelvic floor muscles to achieve a lift and/or a relaxation) with the intravaginal device. The therapeutic energy treatment regimens, PFLs and/or PFRs can be performed over a set time interval (e.g., 1-5 minutes, 1-60 seconds, or 15 seconds) with the intravaginal device. For example, a series can be divided into a period of time (e.g., about 1 second-30 seconds, such as 1 second, 15 seconds, or 30 seconds, or up to 1 minute, or more) during which the therapeutic energy treatment regimens, PFLs and/or PFRs are performed and a period of rest (e.g., about 1 second-30 seconds, such as 1 second, 15 seconds, or 30 seconds, or up to 1 minute, or more) where no PFL and/or PFR are performed. In some instances, each series (e.g., a series including a set number of PFLs and/or PFRs performed, or a series of PFLs and/or PFRs performed over a set time interval) occurs in about 1 second to about 10 minutes (e.g., 1, 2, 3, 4, 5, 6, 7, 8, 9, 10, 20, 30, 40, 50, or 60 seconds, e.g., 1, 2, 3, 4, 5, 6, 7, 8, 9, or 10 minutes). In some instances, the series includes performing PFLs and/or PFRs with the device for 15 seconds and then resting for 15 seconds. A patient may repeat a series at least one additional time (e.g., 1, 2, 3, 4, 5, 6, 7, 8, 9, or 10 times) during a treatment period. An exemplary method of treatment with an intravaginal device of the invention includes a patient performing a series PFLs and/or PFRs for 15 seconds and then resting for 15 seconds, and repeating the series five times over about a 90-second (e.g., 2.5 minute) treatment period. Such an exemplary treatment program can be performed at least once per day (e.g., 1×, 2×, 3×, 4×, or 5× per day). In some instances, the treatment program is determined by, or evaluated by, a medical practitioner. In other instances, the treatment program is determined by the individual. For example, an individual who self-identifies as having a need to train her pelvic floor muscles based on her experience of at least one (e.g., 1, 2, 3, 4, 5, 6, 7, 8, 9, 10, or more) symptom of a PFD or vaginal disorder.

During use, the device can provide indicia to the user regarding the quality and tone of the pelvic floor muscles, e.g., as detected by one or more of the sensors. In particular, the device may include a bioimpedance sensor (e.g., an EIM sensor) or a light detecting sensor (e.g., a LiDAR sensor) that can provide information to the user about the quality and tone of the user's pelvic floor muscles before treatment using the device, during treatment using the device, and after treatment using the device.

During the treatment program the individual may engage with a user interface on an electronic device that is connected to the intravaginal device. The electronic device provides instructions to the user via the user interface that coach the individual through using the intravaginal device of the invention in a treatment program. The instructions may be provided through a software application running on the electronic device. The electronic device generates a readout of results and data through the user interface on the quality and quantity of PFLs and/or PFRs performed with the intravaginal device. The readout of results and data can be observed in substantially real-time or after the completion of the treatment program. The electronic device may instruct the individual to perform a pelvic floor lift or to relax the pelvic floor muscles, such as through a software application running on the electronic device. The individual may be instructed to repeat the pelvic floor lift or to relax the pelvic floor muscles two (e.g., 2, 3, 4, 5, 6, 7, 8, 9, 10, 20, 30, 40, or 50) or more times. The electronic device collects data on the symptoms experienced by the individual during use of the intravaginal device and provides recommendations for adjusting the treatment program to improve efficacy. The electronic device can also notify the individual when to remove the intravaginal device, such as at the end of the treatment period. A treatment period may conclude after a pre-determined time (e.g., about one week to about three months).

The invention also includes methods of calibrating an intravaginal device for treating, or inhibiting or reducing the development or progression of, a pelvic floor disorder in an individual comprising: (a) inserting the intravaginal device into the vagina of the individual and monitoring the engagement of, or relaxation of, a pelvic floor muscle of the individual with the intravaginal device over a calibration period; and (b) using the data collected over the calibration period to calculate a baseline score for at least one performance metric of the engagement of, or relaxation of, a pelvic floor muscle of the individual and/or at least one characteristic of the pelvic floor disorder of the subject. The at least one performance metric of the engagement of, or relaxation of, a pelvic floor muscle of the individual and/or at least one characteristic of the pelvic floor disorder is selected from the group consisting of the maximum number of pelvic floor lifts and/or the maximum number of pelvic floor relaxations performed, the maximum strength of a pelvic floor lift and/or a pelvic floor relaxation performed, and muscle quality muscle strength, and vaginal.

A method of the invention can be used in the treatment of a pelvic floor disorder such as, but not limited to, urinary incontinence (UI), stress urinary incontinence (SUI), urge incontinence, mixed stress and urge urinary incontinence, dysuria (e.g., painful urination), anal or fecal incontinence, pelvic organ prolapse (POP) (e.g., urethra prolapse (urethrocele), bladder prolapse (cystocele), or both urethra and bladder prolapse (cystourethrocele), vaginal vault and cervix prolapse (vaginal vault prolapse), uterus prolapse (uterine prolapse), rectum prolapse (rectocele), sigmoid colon prolapse (sigmoidocele), and small bowel prolapse (enterocele)), pelvic pain, sexual dysfunction (e.g., coital incontinence, a sexual pain disorder, dyspareunia, vaginismus, and/or impaired sexual arousal), weak or impaired pelvic floor muscle function, post-labor issues or damage, pain and/or incontinence caused by damage to a lumbosacral nerve, and nonrelaxing pelvic floor dysfunction. Treatment using a device of the invention may reduce the frequency of occurrence and/or severity of at least one symptom of a pelvic floor disorder may be reduced by at least 5% (e.g., 10%, 20%, 30%, 40%, 50%, 60%, 70%, 80%, or 90%) or more. In particular, symptoms of pelvic floor disorders that make be ameliorated (e.g., treated, reduced) using a method of the invention include, but are not limited to, muscle tone (e.g., hypotonic muscle tone and hypertonic muscle tone), poor muscle strength, bladder leakage, anal or fecal leakage, pain (e.g., muscle pain, lower back pain, pain during urination, pain during defecation, pain during sexual stimulation and/or intercourse), frequency, and urgency.

A number of MEMS sensors (e.g., 1, 2, 3, 4, 5, 6 or more) may be linearly connected and, e.g., equidistant apart on, e.g., a flex strip encased in a biocompatible material, such as silicone. Each sensor can reflect an angle (location) at a specific point. This angular information from the sensors work in conjunction to form a fitted curve or line that reflects the shape and angle of the vagina. The device may be inserted while sitting or standing.

The device is comfortable, flexible and easy to insert and remove. The patient may insert and remove the device herself. Alternatively, a health care professional may insert the device (with or without an insertion tool) and the device may remain inside the patient for up to 90 days. The patient can remove the device herself or go to a health care professional to have it removed. The device may be flexible, in order for the device to take the shape of the patient's vagina.

The device may be configured as a multi-use single user device. The patient can first download an application to an electronic device, such as a smartphone, and pair the device with her electronic device. She can then register the device online and enter her user name and password on the application to begin using the device. The patient then inserts and uses the device at her convenience. As the vagina is not a sterile environment, there is no need to sterilize the device for re-insertion. The patient may regularly wash the probe with mild soap and water before and after using the device.

The device may be connected to a transmitter box that wirelessly (e.g., via Bluetooth) sends the positional data gathered from the vaginal device sensors to the electronic device (e.g., a smartphone or computer) that communicates to the patient through an interactive application. The sensors of the intravaginal device may be used to determine a vaginal angle ($\theta_V$; FIGS. 4A-4D) of a patient. Baseline measurements of vaginal angle can be obtained and compared to data obtained after a period of performing pelvic floor exercises. For example, for a patient who is healthy or has mild symptoms of incontinence, the sensors of the intravaginal device may be used to determine a $\theta_V$ of approximately 45° relative to the floor when the patient is standing. When the patient performs a lift exercise, the sensors of the intravaginal device may determine that the $\theta_V$ increases towards 90°. The exercises may be performed sitting or standing. In some instances, the observed change in deflection angle will be greater when the woman is standing. A woman with strong pelvic floor muscles may be able to lift her pelvic floor muscles such that the device is oriented between 45° to 90° or more (e.g., nearly 90°) relative to the floor. If the woman has symptoms of incontinence, she may exhibit hypermobility of her urethra, which can be reflected in a readout from the intravaginal device, which indicates that the pelvic musculature cannot fully hold and support the urethra and bladder in its correct place. In the event that a woman has extreme (e.g., stage IV) stress urinary incontinence and/or total POP, the sensor angle may be depressed towards 0° at rest. A physician may test the woman's pelvic floor musculature by asking her to try to lift her pelvic floor, to perform a pelvic floor exercise, to cough or bear down, or to relax. In some cases of POP, when the woman attempts to bear down, the organs may deform the device in a caudal direction, The data from the pelvic floor exercises may be uploaded automatically to an online database. The electronic device (e.g., a smartphone or computer) can also store a certain amount of this data. The application is user-friendly and can be configured to allow the patient to share her data. The application can be a tool for the health care professional to program a specific exercise regimen for the patient or otherwise communicate with the patient. The application may privately communicate with the patient by sending data, such as scores, charts, graphs, or reports, reminders, and encouragement to the patient via push notifications. The application can also allow patients to send information to the database, responding to questionnaires and reporting continence, improvement, and/or problems.

The shape of the vagina can be determined using, e.g., data from, e.g., the MEMS sensors in the device, which reflect the position of the patient's pelvic floor in her body. The pelvic floor muscles lift the vaginal canal when a patient performs a PFL. The shape of the vagina from the data in the sensors can be used to monitor or diagnose a pelvic floor disorder. For example, if the position of the patient's pelvic floor descends, it can be useful to monitor the patient for possible POP. Monitoring the position of the patient's pelvic floor will help to prevent further damage and to correct and/or improve the current state of a patient's pelvic floor, which may allow the patient to avoid surgery or other more invasive options. The device may be used for prevention, rehabilitation, and treatment of urinary incontinence (urge, stress, and mixed), anal or fecal incontinence (gas, liquid, mucus, solid), POP, pelvic pain, sexual dysfunction, and postpartum health.

The device may show the patient and her health care professional the movement of the pelvic floor muscles as it is reflected by the configuration of the vagina in real time during training exercises. Using the biofeedback offered by the device, the patient alone, or assisted by her health care professional, can strengthen her pelvic floor correctly. The data from the sensors allows for measuring and recording the exercise data, giving the health care professional and/or the patient the ability to track the patient's compliance, pelvic floor strength, and improvement as a result of the patient's performance of pelvic floor exercises.

The data may be captured as a score based an algorithm that measures the angles (location) of the sensor during PFL and may also include a measure of the strength or endurance of the pelvic floor muscles. The score reflects the patient's pelvic floor exercises during her training (date and time). The device and application may provide point of care data collection capabilities which may standardize care for pelvic floor disorders. The data created by the device may be transmitted to a centralized database creating a personal health record for the patient, providing care and measurable results.

This data can also provide predictive information that notifies a patient and their health care professional about the potential need for various treatment options to improve the patient's quality of life. For example, the changes observed in patients who have hypermobility are markedly different from patients that do not have hypermobility (e.g., associated with stress urinary incontinence). By establishing a baseline on a patient using a device described herein and, e.g., a database of information on the patient, one can monitor the patient's pelvic floor descent or damage in real-time or over a period of time. A device described herein can also be used to monitor a patient's improvement over time while using the device (e.g., to perform PFL that train and strengthen the pelvic floor musculature). Therefore, the patient can be treated before the damage needs to be corrected through surgical means.

A device of the invention may also be used to characterize the health state or change in health state over time of a female patient. For example, the data generated by the device (e.g., the score) may be correlated to various stages of POP (e.g., stage 0, I, II, III, and IV). A score of 0 may correspond to stage IV, 0-15 with stage III, 15-30 with stage II, 30-45 with stage I, and above 45 with stage 0. These scores may or may not be absolute scores, and they may be normalized for each individual patient. For example, a score range may be determined empirically for each individual user. By tracking the score achieved during certain exercises, the device can calculate a change or transition from one health state to another (e.g., stage IV to stage III, stage III to stage II, stage II to stage I, and stage I to stage 0). For example, a severe prolapse patient at stage IV may initiate PFLs using an intravaginal device of the invention. Over the course of a 3-6 week treatment period, the patient performs a treatment regimen 1-10 times per day, as described herein. The patient may start out generating baseline sensor data at rest. After the 3-6 week treatment period, the patient may improve to stage II or III POP and may exhibit an upward shift in sensor data during the PFL.

A device of the invention may also be used to monitor the long term health state of a female subject. For example, the device may be administered as a routine test every time the female visits her general practitioner or OB/GYN specialist for a yearly checkup. The health state of the female's pelvic floor can be monitored over time such that a deterioration in score may be used to predict that a pelvic floor disorder is oncoming. The device may be customized for each female (e.g., the circumference of the main body may be sized specifically for the subject and/or the tether length may be selected based on the length of the subject's vaginal canal). The device may also have "smart" capabilities. For example, a woman with a pelvic floor disorder may wear the device when performing routine daily activities. If she performs a movement that is detrimental to her pelvic floor health, the sensors may detect the movement and the device may alert the female to halt the activity.

Methods of Delivering Therapeutic Energy

Intravaginal device 100 may contain one or more energy transmitters (e.g., RF, laser, or electrical current stimulation). Energy transmitters 210 (FIGS. 21-25) can be used to deliver therapeutic energy in the form of heat. RF transmitters can be used to provide nonablative radio frequency in the form of thermal energy that treats vaginal disorders, such as skin laxity. By applying heat, the thermal damage stimulates collagen production in deep layers of the skin and subcutaneous tissue to strengthen and fortify the collagen network in the vagina (e.g., the introitus and tissues of the vaginal cavity, e.g., vaginal anterior, posterior and sidewalls). This may also trigger formation of new elastin. Furthermore, intravaginal device 100 may contain temperature sensors 200 to track the heat generated by RF transmitters. Energy transmitters 210 (e.g., RF transmitters) may be positioned around main body 110 and/or along the length of tether 10. Exemplary therapeutic RF transmitters and methods of treatment using such transmitters are described, for example, in U.S. Publication Nos. US20170333705, US20130245728, US20150327926, US20160296278, US20170071651, US20180001103, US20160263389, US20160263388, US20160263387, and US20150297908, and in Araujo et al., (*An Bras Dermatol.* 90(5): 707-721, 2015) and Karcher et al., (*Int. J. Wom. Derm.* 2: 85-88, 2016), the disclosures of which are each hereby incorporated by reference in their entirety.

The device may be used for short or extended periods of time. The different RF transmitters distribute RF energy to different areas in the vagina (e.g., the introitus or areas within the vaginal cavity). RF transmitters operate at one or more frequencies in the range of 1 kHz to 100 MHz. The power level of RF transmitters may vary from 1 mW to 500 W, depending on physician recommendations and the duration of therapy. Temperature sensors 200 and microcontroller 900 automatically regulate the frequency and power level applied by the device in order to regulate the appropriate temperature for optimal patient comfort and therapeutic activity. For example, RF transmitters can raise the temperature of the local tissue from 37° C. to 60° C. A cooling mechanism may be used to prevent the heat from reaching dangerous limits. Units of heat or energy may be transmitted as a unit per area of tissue (e.g., W/cm$^2$). This is described, for example, in Hsu et al. *Obstet. Gynecol.* 105 (5:1), 1012-1017, 2005, Benedet et al. *J. Reprod. Med.* 37(9): 809-812, 1992, and in U.S. Publication No. US20180001103, the disclosures of which are each hereby incorporated by reference in their entirety. For example, the one or more energy transmitters 210 (e.g., RF transmitters, lasers, electrical stimulators) may transmit energy (e.g., 1 mW-500 W, e.g., 100 mW-300 W, e.g., 1-10 mW, e.g., 2 mW, 3 mW, 4 mW, 5 mW, 6 mW, 7 mW, 8 mW, 9 mW, 10 mW, e.g., 10-100 mW, e.g., 20 mW, 30 mW, 40 mW, 50 mW, 60 mW, 70 mW, 80 mW, 90 mW, 100 mW, e.g., 100-1000 mW, e.g., 200 mW, 300 mW, 400 mW, 500 mW, 600 mW, 700 mW, 800 mW, 900 mW, 1 W, e.g., 1-10 W, e.g., 2 W, 3 W, 4 W, 5 W, 6 W, 7 W, 8 W, 9 W, 10 W, e.g., 10-100 W, e.g., 20 W, 30 W, 40 W, 50 W, 60 W, 70 W, 80 W, 90 W, 100 W, e.g., 100-1000 W, e.g., 200 W, 300 W, 400 W, 500 W, 600 W, 700 W, 800 W, 900 W, or 1000 W) in units of energy per surface area of tissue (e.g., 1 mm$^2$ to 10 cm$^2$, e.g., 1-10 mm$^2$, 10-100 mm$^2$, or 1-10 cm$^2$) for an amount of time (e.g., 10 seconds-30 minutes or more, e.g., 30 seconds, 1 minute, 10 minutes, 20 minutes, or 30 minutes). The energy may also be transmitted to a certain depth within the tissue (e.g., 0.1 mm-10 cm, e.g., 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 1 cm, 2 cm, 3 cm, 4 cm, 5 cm, 6 cm, 7 cm, 8 cm, 9 cm, and 10 cm).

Figure 28:
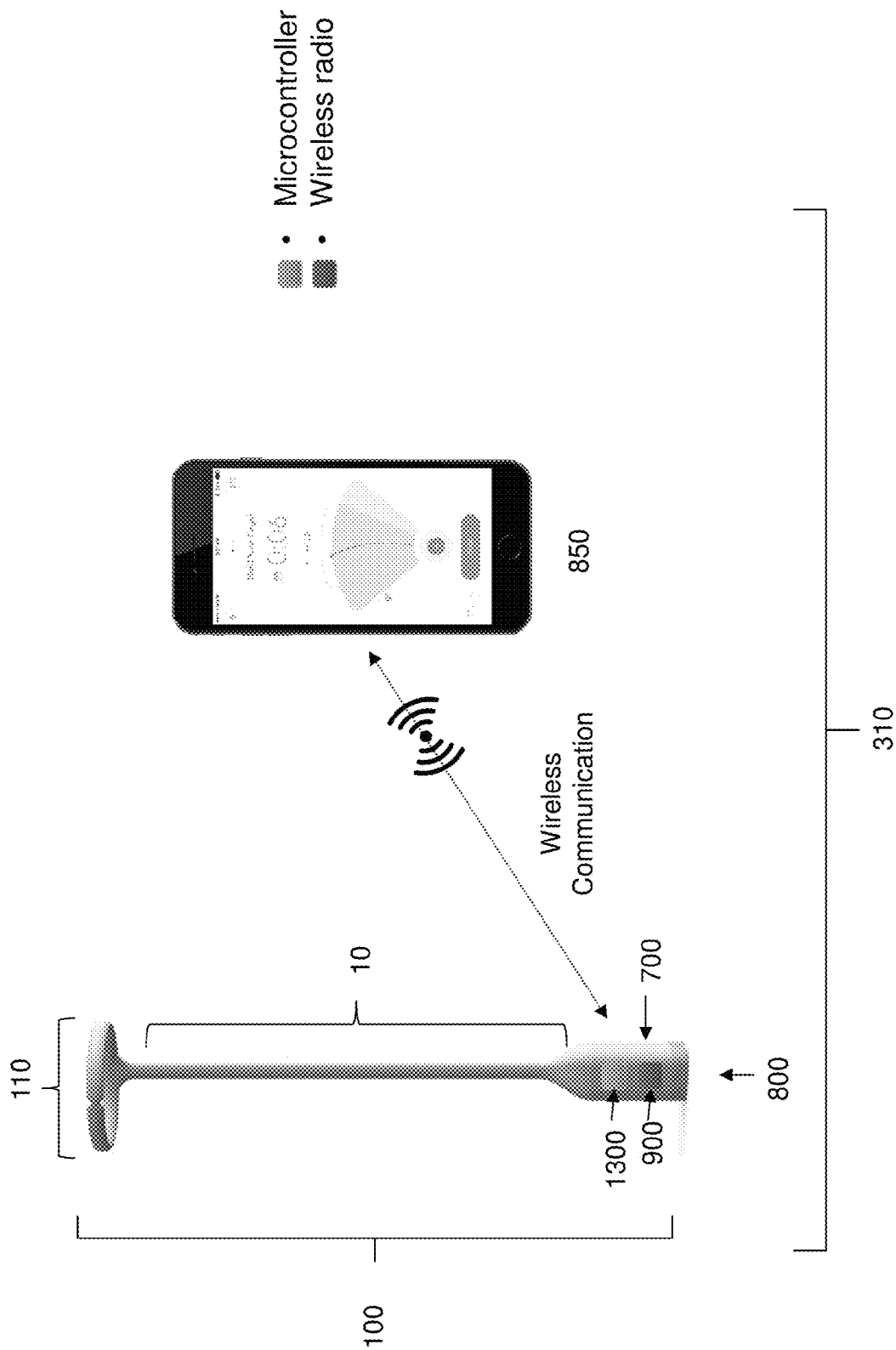
FIG. 28 is a schematic showing system 310 that includes intravaginal device 100 with main body 110, tether 10, circuit board 700, battery 800, microcontroller 900, and wireless communication antenna 1300, which communicates with graphical user interface 850, which can be, e.g., a smartphone.

Intravaginal device 100 can connect to a user interface, e.g., via a smartphone application by means of a USB port, Bluetooth Low Energy, Wi-Fi, or a similar wired or wireless technology (FIG. 28). An application can be used by the patient or a physician to adjust the frequency, power level, or duration of treatment. Intravaginal device 100 may be battery powered or connected to a power source, such as power box 810 (e.g., an external battery) or an AC outlet. The circuitry used to power the device may be as described in FIG. 29.

In order to effectively power energy transmitters (e.g., RF transmitters) 210, intravaginal device 100 may be configured for use with a large battery 800 or external power supply 810. Intravaginal device 100 may also be designed with tether 10 that is configured as a separable tether with modular components (FIGS. 26-27). The top half of the device may be configured as a long-term wearable component which contains the ring and part of the tether. Tether 10 can be connected to a separate short-term device which may have additional RF transmitters to apply RF therapy to the lower section of the vagina and/or the introitus. Battery 800 may only power microcontroller 900, wireless radio 1300, and accelerometers 200. A short-term device (e.g., modular and or separable tether) may be inserted into the vagina to connect to the long-device to power energy transmitters (e.g., RF transmitters) 210 and/or recharge a battery in battery 800. Alternatively, the short-term device may have a wireless power transmitter and the long-term device may have a wireless power receiver. The long-term and short-term devices may have junctions configured for connecting the two portions of the device. The connections may be, e.g., magnetic or other physical connections and may provide an electrical (e.g., Ohmic) connection. The magnetic connection may ease the connection of the separable pieces. Alternatively, an interlocking, press fit, snap, or other mechanism may be used to connect the modular tether (e.g., short term-device) to the long term wearable device.

When using the intravaginal device, the patient may also wish to use a grounding pad, which can be connected to the device and to the subject in order to prevent the buildup of energy that could harm the patient. The use of a grounding pad is described in, e.g., Millheiser et al. (*J. Sex Med.* 7:3088-3095, 2010; incorporated herein by reference).

Methods of Optimizing Sensor Placement to Diagnose a Pelvic Floor Disorder with an Intravaginal Device of the Invention The position of sensor(s) 200 of intravaginal device 110 may be located for maximal signal change during a pelvic floor exercise and for maximal signal-to-noise ratio. The device may contain one or more sensors 200 (e.g., 1, 2, 3, 4, 5, 6, 7, 9, 10, 11, 12, 13, 14, 15, 16, 17, 18, 19, 20, or more) on main body 110 and/or tether 10. The fornix sensors are sensors that reside in the portions of the intravaginal device that extend into the anterior and posterior fornices. Additional vaginal sensors reside, e.g., in the tether 10 caudal to the fornices. In one embodiment, an intravaginal device as depicted in FIG. 3 may be used. In this embodiment, intravaginal device 100 has 12 sensors: 8 sensors in tether 10 (S1-S8), and 5 sensors in main body 110 (S8-S12). Sensor S8 is shared by both main body 110 and tether 10. Once a device is designed with optimally placed sensors, the device may be used to effectively diagnose or treat a pelvic floor disorder (e.g., POP).

Figure 6A:
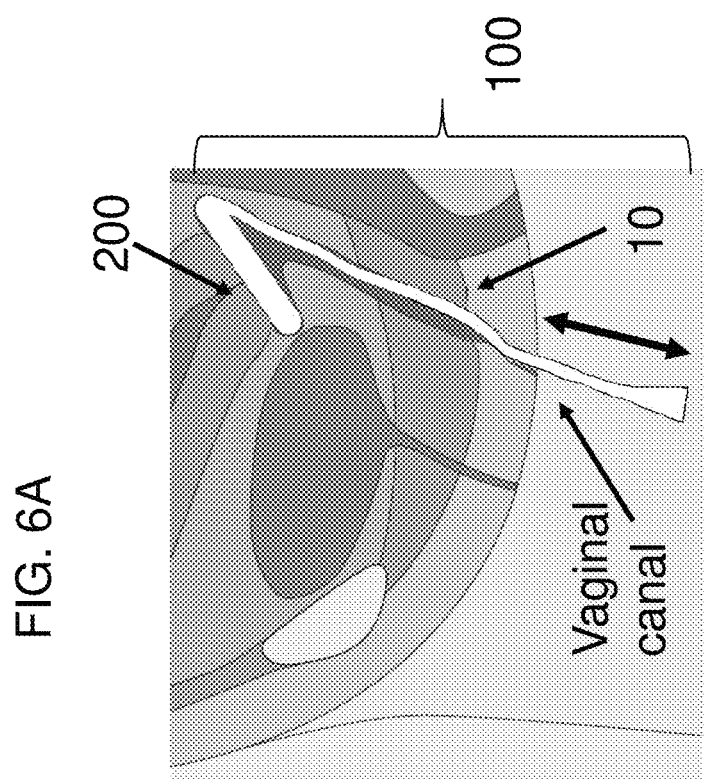
FIG. 6A is a schematic drawing showing insertion of intravaginal device 100 with main body 110 into the vaginal canal and fornices. The bidirectional arrow indicates a portion of the device that is outside of the introitus. Intravaginal device 100 may be configured to exclude this external portion, such that intravaginal device 100 resides completely within the vagina. The length of the vagina can be determined by measuring the length of intravaginal device from main body 110 to the end of tether 10 at the point that extends to the introitus.
Figure 7:
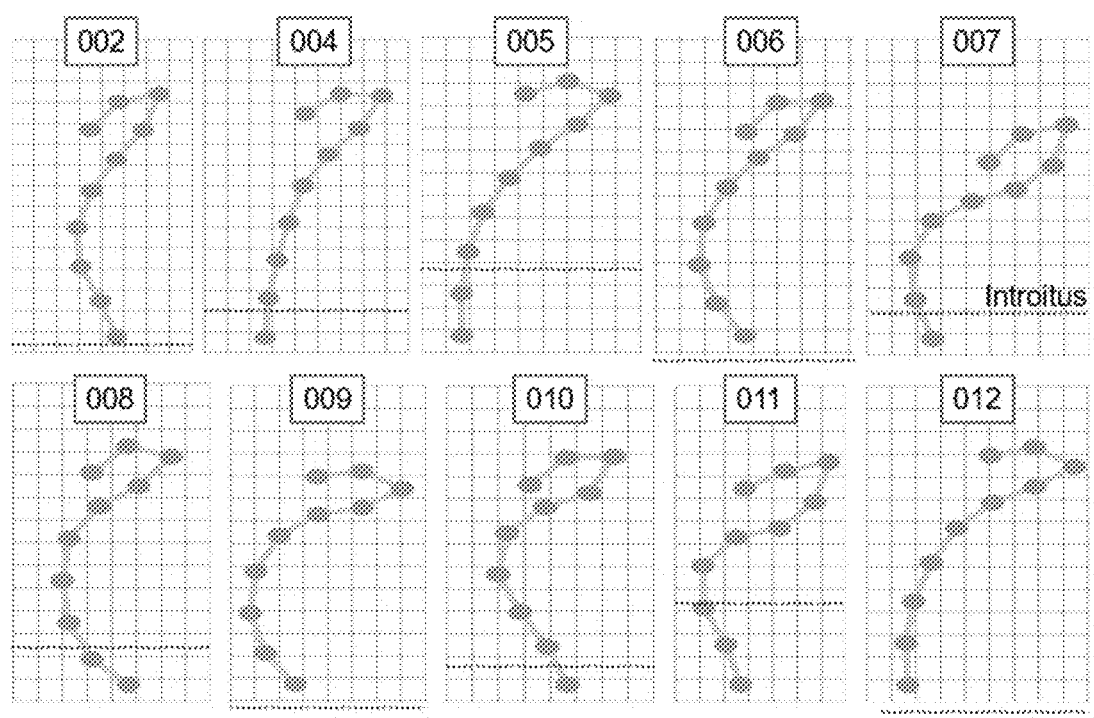
FIG. 7 is a set of 10 panels with each panel representing data from a single subject. The panels illustrate the position of sensors (S1-S10; see FIG. 4D) of intravaginal device 100 in each of the ten subjects during PFR. The dashed line indicates the virtual plane of the introitus (horizon) for each subject. The sensor data were generated using MEMS sensors.

As the intravaginal device has a known length, the vaginal length of a subject may be calculated by determining the length of the tether from the introitus of the vagina to the main body, when positioned within the vaginal fornices (FIG. 6A). These measurements are illustrated in FIG. 7, where the position of each sensor 200 is shown, and the dashed line indicates the position of the introitus of the vagina. The intravaginal device may have a tether that extends beyond the introitus of the vagina or the tether may reside completely inside the vagina.

Different vaginas may have different lengths and different characteristic curvatures. Therefore, the physical characteristics of intravaginal device 100 (e.g., length of tether 10, circumference of main body 110, number of sensors 200, and placement of sensors 200) may be selected to optimize fit and function based on a particular vaginal length and curvature FIG. 7 shows different lengths and curvatures of vaginas of 10 subjects. These data derived from intravaginal device 100 in a patient may yield insight into the internal organ position and aid a physician in diagnosing a pelvic floor disorder (e.g., POP). For example, sensors 200 of intravaginal device 100 within the vagina of patients 007, 009, and 011 (FIG. 7) indicate that the cranial part of the vaginal canal is posteriorly and caudally displaced, suggesting deformation from pelvic organ prolapse.

Figure 9:
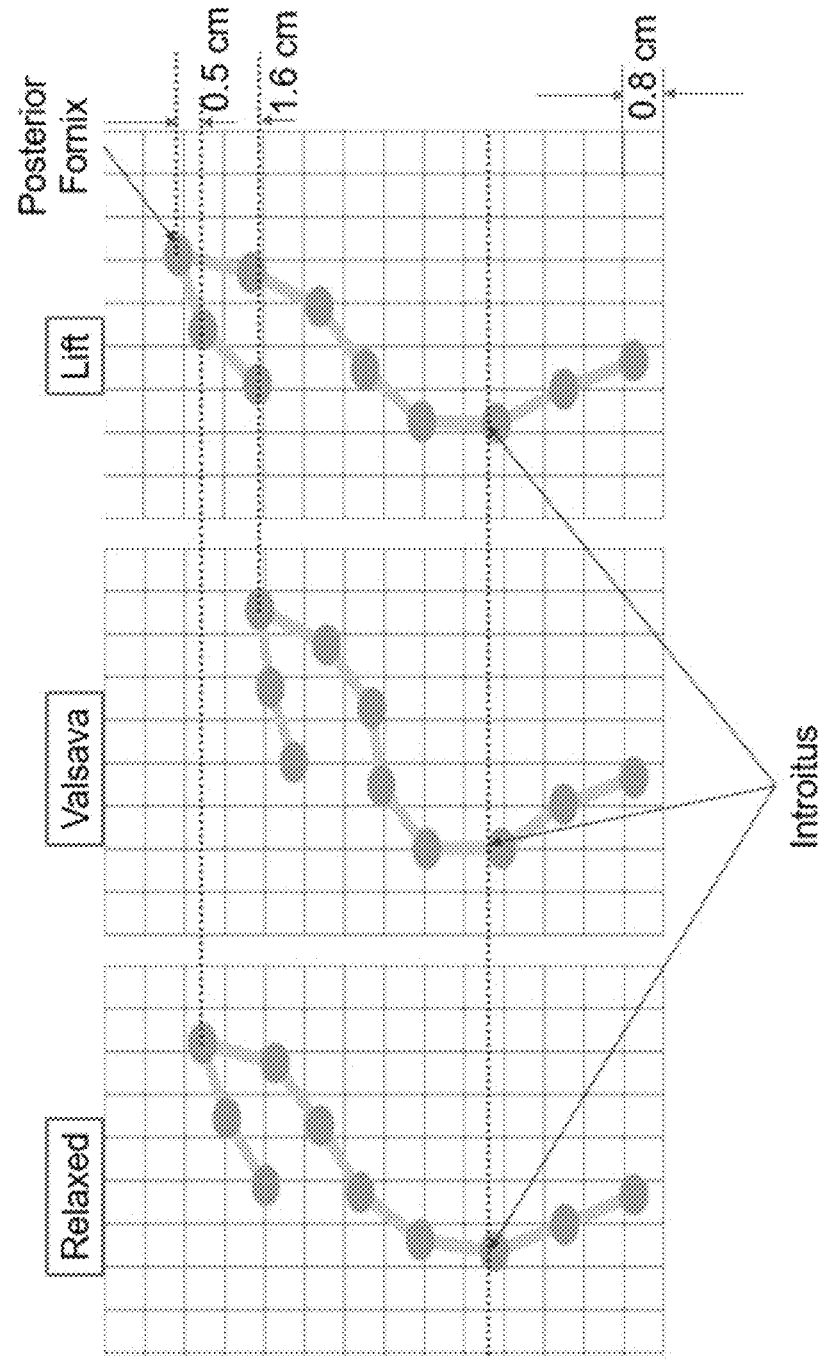
FIG. 9 is a set of three panel images illustrating the positions of sensors S1-S10 (see, e.g., FIG. 4D) of an intravaginal device in a subject (011) with a relatively short vagina (length during pelvic floor relaxation 7.7) (left panel), during Valsalva maneuver (middle panel), and during pelvic floor lift (right panel). The bottom dashed line indicates the position of the virtual plane of the introitus during each maneuver. The three dashed lines in the upper portion illustrate the position of the posterior fornix sensor during each maneuver. During Valsalva maneuver, the posterior fornix sensor moves down 1.6 cm relative to its position during pelvic floor relaxation. During a pelvic floor lift, the posterior fornix sensor moves up 0.5 cm relative to its position during relaxation. The sensor data were generated using MEMS sensors.
Figure 10:
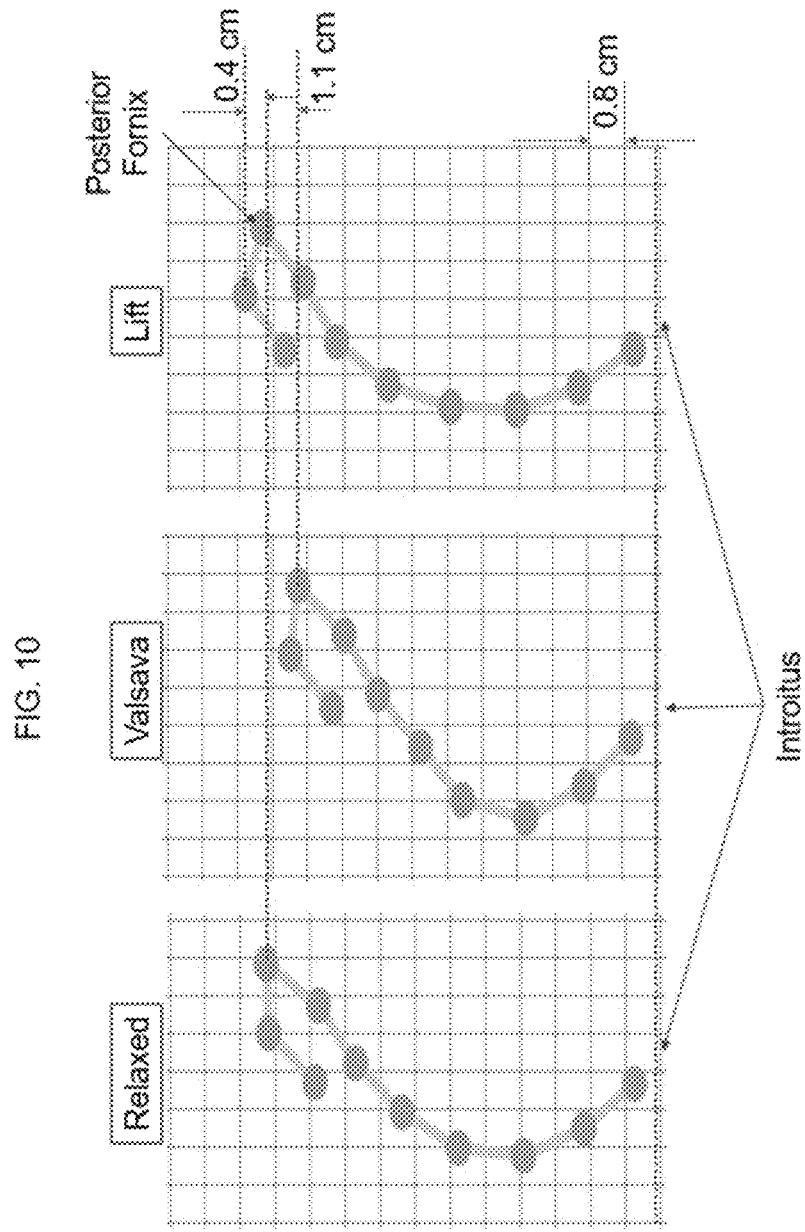
FIG. 10 is a set of three panel images illustrating the positions of sensors S1-S10 (see, e.g., FIG. 4D) of an intravaginal device in a subject (006) with a long vagina (length during PFR 12.2 cm) during pelvic floor relaxation (left panel), during Valsalva maneuver (middle panel), and during pelvic floor lift (right panel). The bottom dashed line indicates the position of the virtual plane of the introitus during each maneuver. The three dashed lines in the upper portion illustrate the position of the posterior fornix sensor during each maneuver. During Valsalva maneuver, the posterior fornix sensor moves down 1.1 cm relative to its position during pelvic floor relaxation. During a pelvic floor lift, the posterior fornix sensor moves up 0.4 cm relative to its position during relaxation. The sensor data were generated using MEMS sensors.

When the user performs a pelvic floor maneuver (e.g., Valsalva maneuver, PFL, sustained PFL, and repeated PFL), the angles (locations) of sensors 200 change. For example, when using an intravaginal device with 12 sensors, subjects, with a broad range of vaginal lengths, showed a caudal movement of the posterior fornix sensor during Valsalva maneuver (relative to the position of the posterior fornix during relaxation) and a cranial movement of the posterior fornix sensor during a PFL (again, relative to the position of the posterior fornix sensor during relaxation. In a subject with a short vagina (7.7 cm), caudal movement of the posterior fornix of 1.6 cm was seen during a Valsalva maneuver and cranial movement of the posterior fornix of 0.5 cm was seen during a PFL (FIG. 9). In a subject with a long vagina (12.2 cm), 1.1 cm of caudal movement was seen during Valsalva maneuver and 0.4 cm of cranial movement was seen during PFL (FIG. 10).

The comparison between the location of sensors on the tether 10, within the vaginal canal below the fornix, during various pelvic maneuvers, compared to the relaxed state, can help the physician to visualize the deformation of the vaginal canal by extrinsic pelvic organs and in some instances to diagnose a subject with a pelvic floor disorder (e.g., POP and/or hypermobility). Furthermore, because the main body 110 of intravaginal device 100 surrounds, for example, a cervix, the intravaginal device is anchored in place, thereby providing reference positions for visualization during relaxation and pelvic floor maneuvers on a graphical user interface Each sensor 200 may be used to measure a vaginal angle ($\theta_V$) or fornix angle ($\theta_F$) (FIGS. 4A-4D) based on the position and/or orientation of a sensor with respect to the virtual plane of the introitus ("horizon"). Pairs of sensors 200 in main body 110, either in the anterior fornix or within the lateral fornices, may be treated as an individual node (FIG. 4A) of sensors. Therefore, the lateral fornix sensors A10 and A11 may be treated as a single node S9, while the anterior fornix sensors A9 and A12 may be treated as a single node S10 (FIGS. 4B and 4D). The vaginal angle may be calculated by taking the average of the angle between two or more, or all, of nodes S1-S7 and the horizon. The fornix angle may be calculated by taking the average of the two or more of the nodes S8-S10 relative to the horizon.

As the vagina and the fornix is not always straight, the vaginal and fornix angles may be calculated by multiple methods. For example, $\theta_V$ may be calculated by averaging 2 or more sensors from S1-S8 relative to the horizon, or by taking the best-fit line between S1 and S8 relative to the horizon.

Thus, the change in the sensor position and orientation may be quantitatively analyzed using the metrics (e.g., vaginal angle and fornix angle) described above to evaluate pelvic floor movement.

Figure 11:
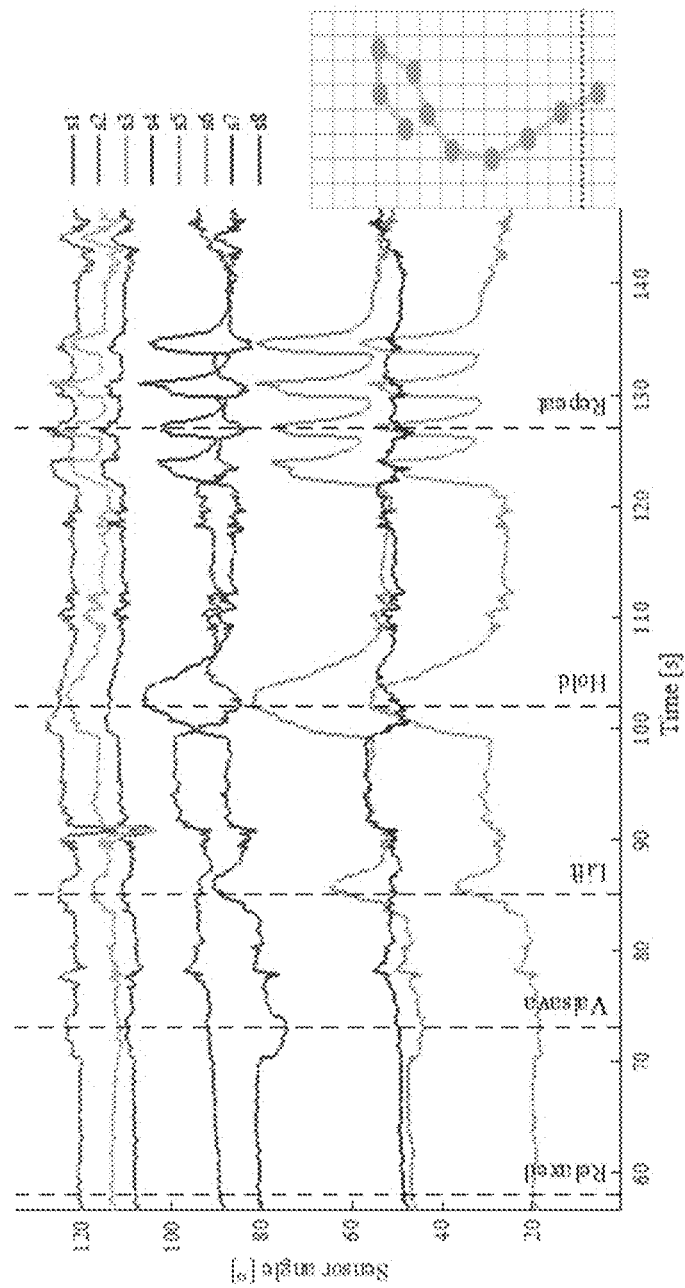
FIG. 11 is a graph plotting, on the ordinate, the sensor angle (location) sensors S1-S8 (degrees) and, on the abscissa, time (seconds) during which a subject (010) performed a series of maneuvers as indicated by the vertical lines (pelvic floor relaxation, Valsalva maneuver, pelvic floor lift, sustained pelvic floor lift (hold), and serially repeated pelvic floor lift (repeat)). Sensors S4-S6 showed the largest change in sensor angle during movements. Sensors S7 and S8 showed an inverted angular response as compared to the other sensors. The sensor data were generated using MEMS sensors.
Figure 12:
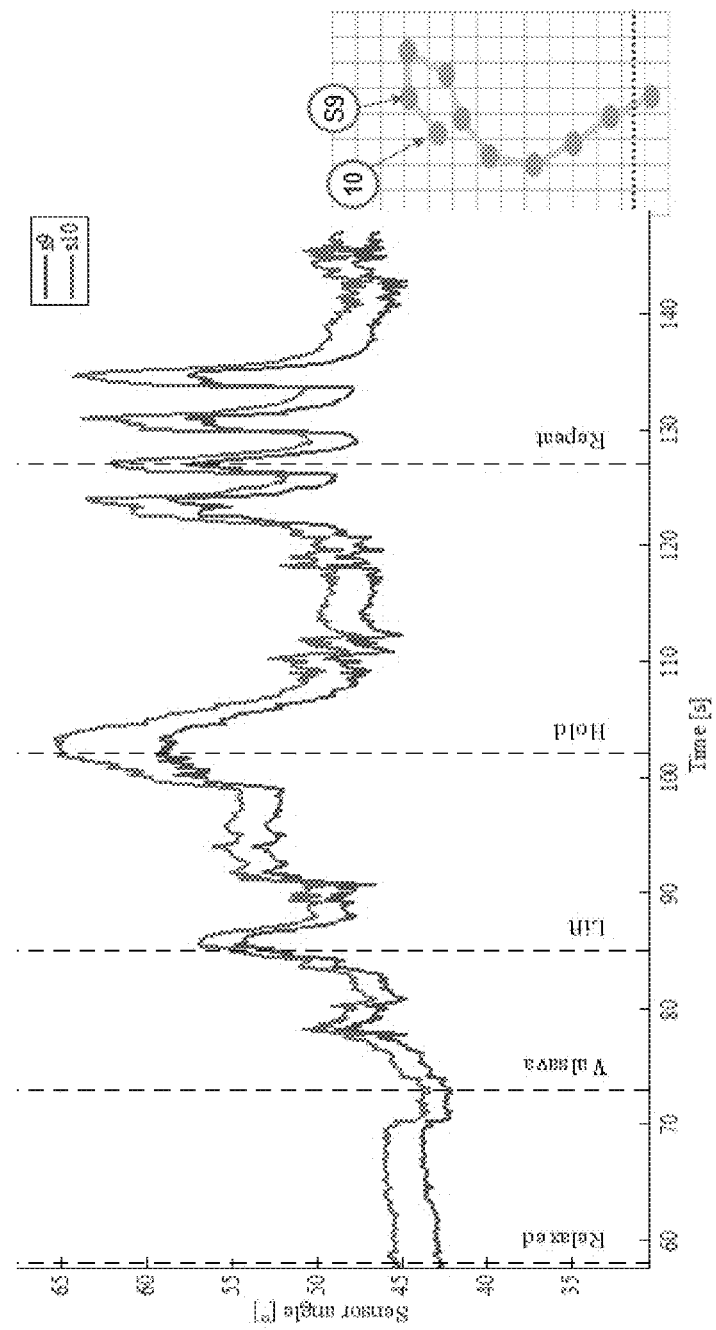
FIG. 12 is a graph plotting, on the ordinate, the sensor angle for sensors S9-10 (degrees) and, on the abscissa, time (seconds) during which a subject (010) performed a series of maneuvers as indicated by the vertical lines (pelvic floor relaxation, Valsalva maneuver, pelvic floor lift, sustained pelvic floor lift (hold), and serially repeated pelvic floor lift (repeat)). S9 represents the average position of sensors in the lateral fornices, and S10 represents the average position of the anterior fornix sensors. S9 and S10 are highly correlated, though S10 demonstrates a consistently larger signal. The sensor data were generated using MEMS sensors.
Figure 13:
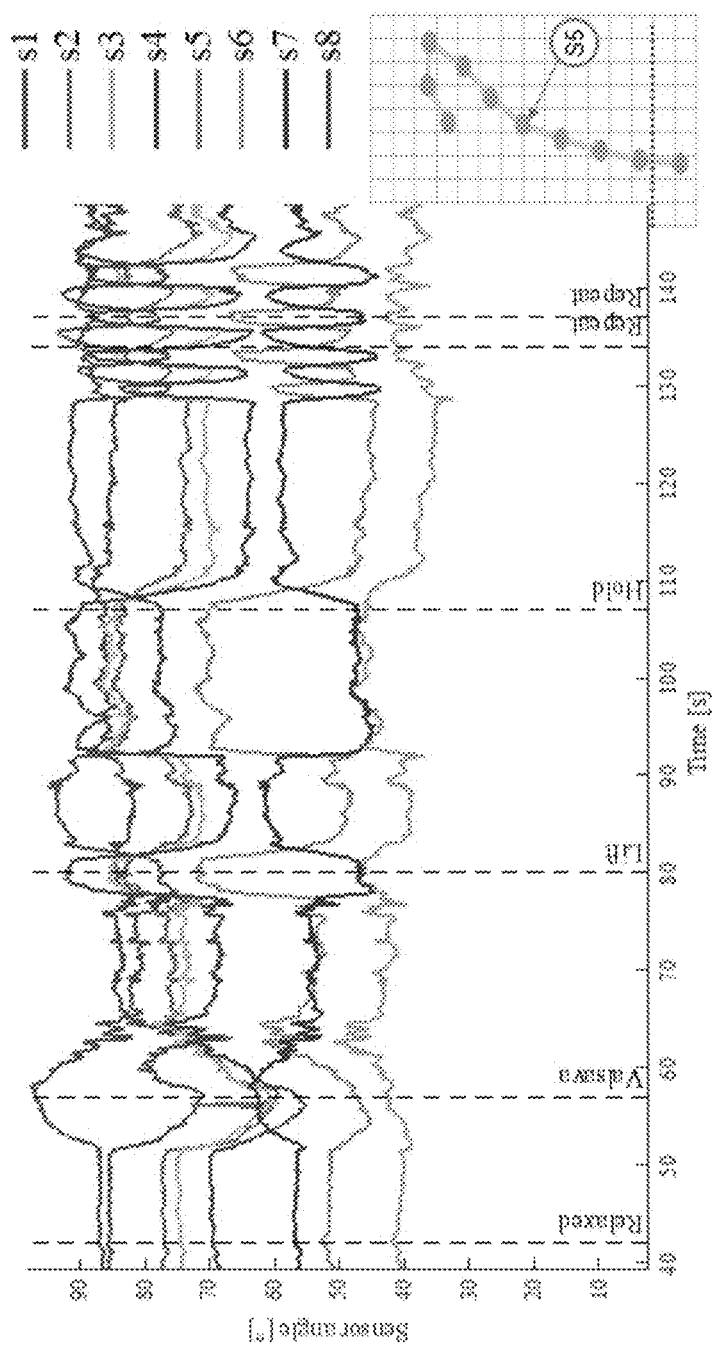
FIG. 13 is a graph plotting, on the ordinate, the sensor angle for sensors S1-S8 (degrees) and, on the abscissa, time (seconds) during which a subject (004) performed a series of maneuvers as indicated by the vertical lines (pelvic floor relaxation, Valsalva maneuver, pelvic floor lift, sustained pelvic floor lift (hold), and serially repeated pelvic floor lift (repeat)). Sensors S4-S5 showed the largest change in sensor angle during maneuvers. The sensor data were generated using MEMS sensors.
Figure 14:
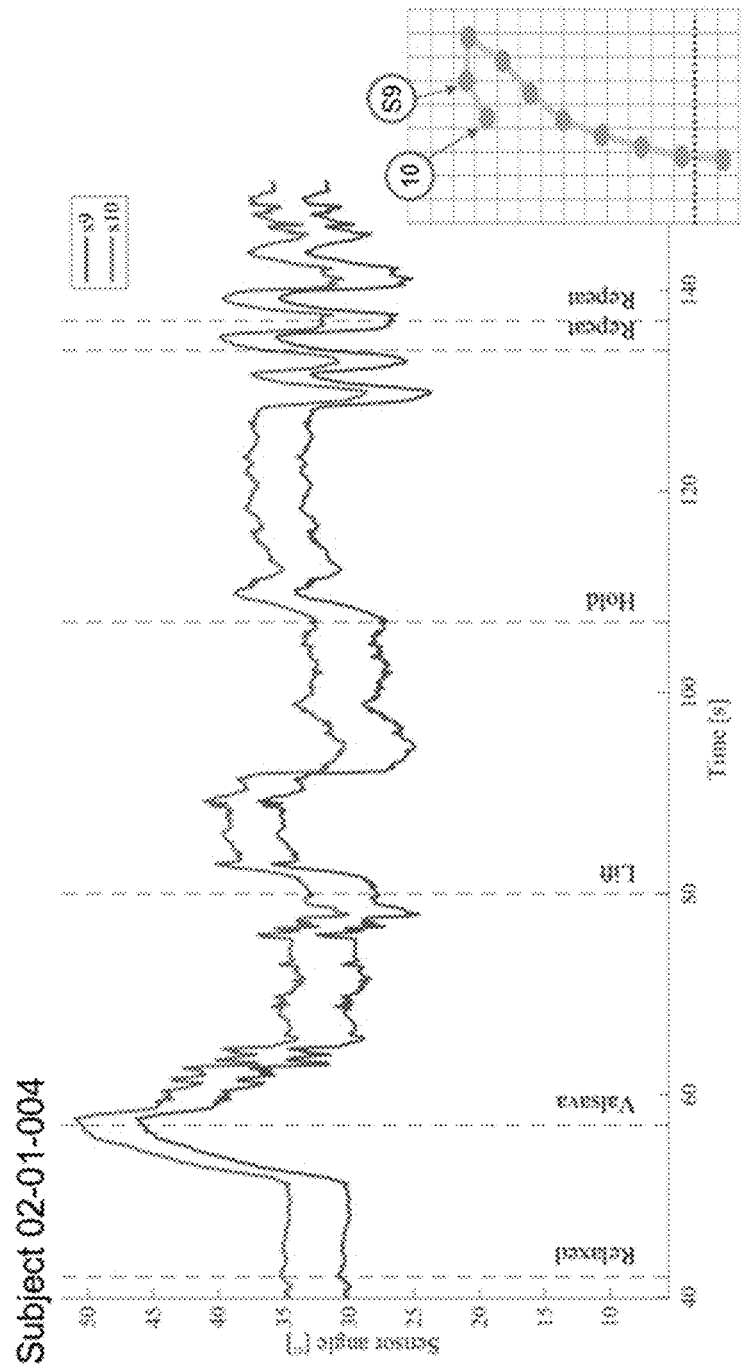
FIG. 14 is a graph showing the sensor angle for sensors S9 and S10 versus time in subject 004. While S9 and S10 are highly correlated with each other, the direction of movement is opposite to that of subject 010. The sensor data were generated using MEMS sensors.
Figure 15:
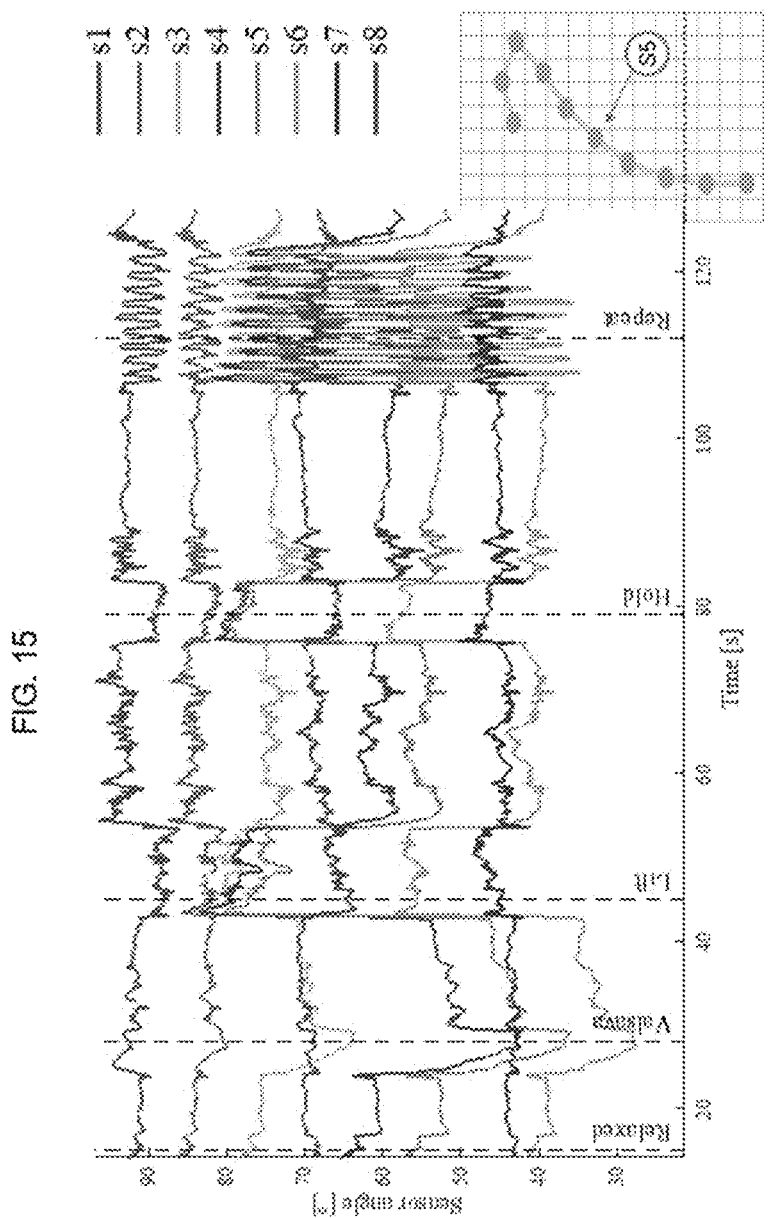
FIG. 15 is a graph plotting, on the ordinate, the sensor angle for sensors S1-S8 (degrees) and, on the abscissa, time (seconds) during which a subject (005) performed a series of maneuvers as indicated by the vertical lines (pelvic floor relaxation, Valsalva maneuver, pelvic floor lift, sustained pelvic floor lift (hold), and serially repeated pelvic floor lift (repeat)). Sensor 5 showed the largest change in sensor angle during maneuvers. The sensor data were generated using MEMS sensors.
Figure 16:
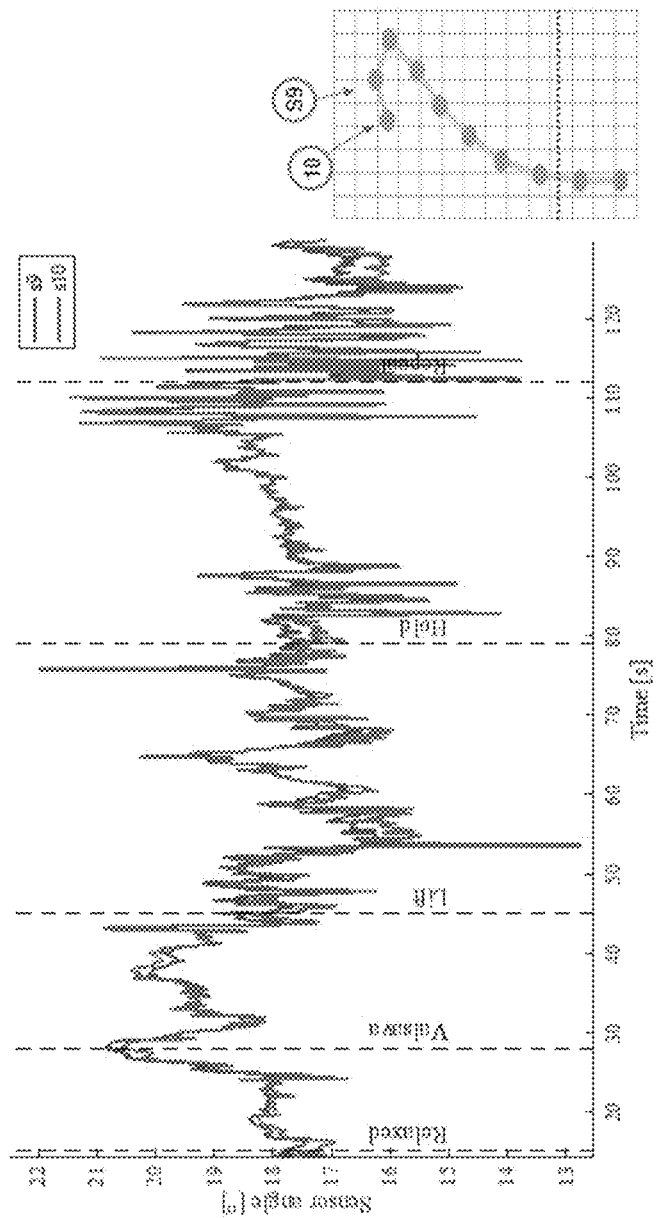
FIG. 16 is a graph showing the sensor angle for sensors S9 and S10 versus time in subject 005. S9 and S10 are highly correlated but both showed a lower signal to noise ratio than S4 and S5 for the same subject. The sensor data were generated using MEMS sensors.
Figure 17C:
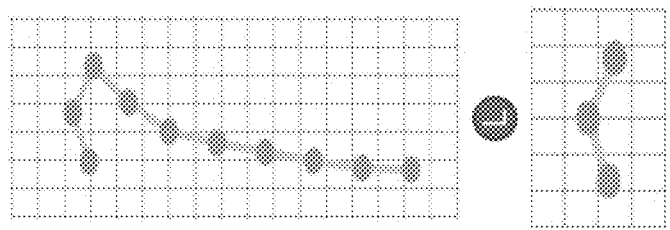
FIG. 17C shows the position of all sensors (S1-10) (top) and fornix sensors (S9-10) (bottom) during a pelvic floor lift maneuver. The graphs of S9-10 show that, for this subject, data produced with the fornix sensors are less robust than data produced with the tether sensors (S1-S8). The sensor data were generated using MEMS sensors.
Figure 17B:
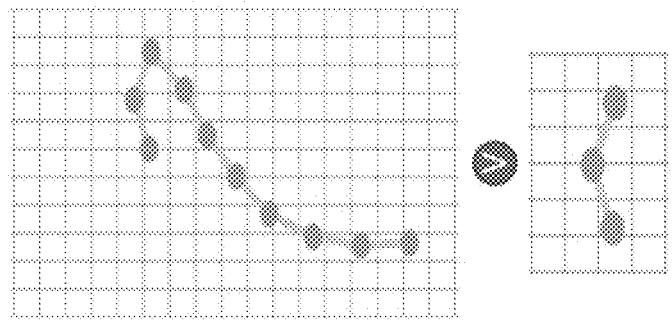
FIG. 17B shows the position of all sensors S1-10 (top) and the fornix sensors S9-10 (bottom), during a Valsalva maneuver.
Figure 17A:
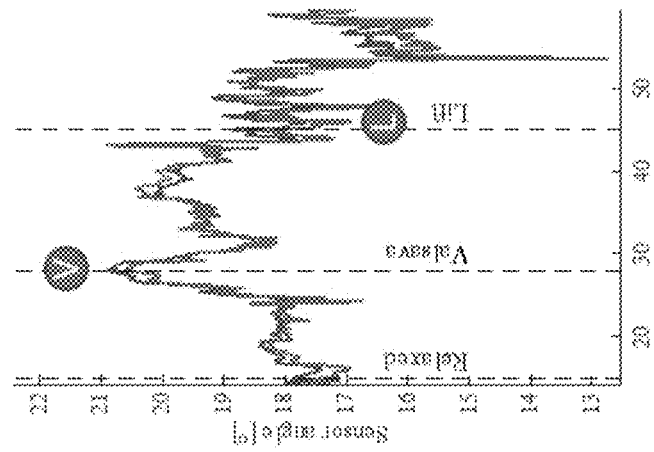
FIG. 17A is a graph showing the sensor angle for sensors S9 and S10 versus time in subject 005. Subject 005 performed pelvic muscle relaxation ("R"), Valsalva maneuver ("V"), and pelvic floor lift ("L").
Figure 18:
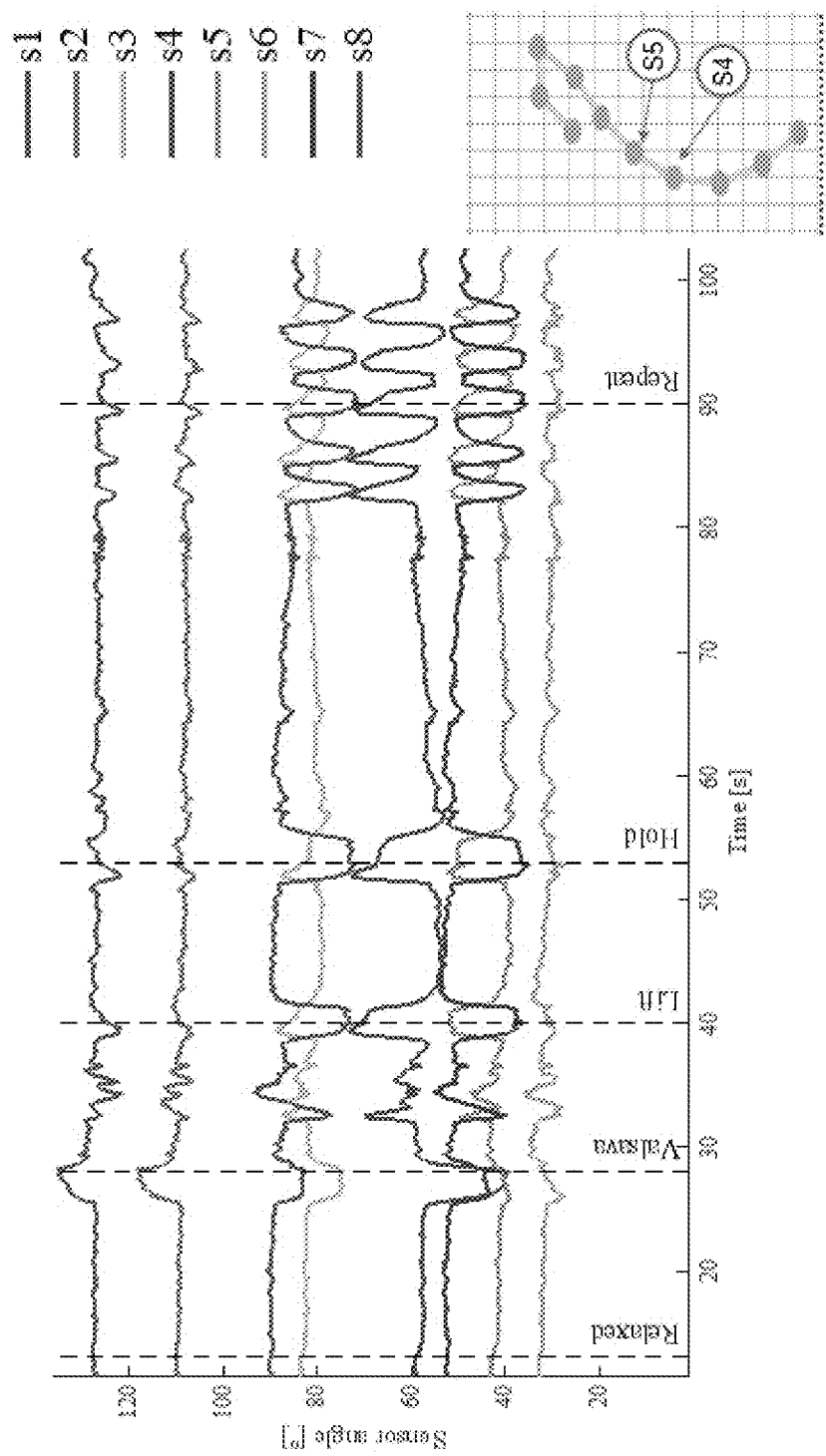
FIG. 18 is a graph plotting, on the ordinate, the sensor angle for sensors S1-S8 (degrees) and, on the abscissa, time (seconds) during which a subject (006) performed a series of maneuvers as indicated by the vertical lines (pelvic floor relaxation, Valsalva maneuver, pelvic floor lift, sustained pelvic floor lift (hold), and serially repeated pelvic floor lift (repeat)). Subject 006 was noted to have a long vagina. Sensors S4-S5 showed the largest change in sensor angle during maneuvers. The sensor data were generated using MEMS sensors.
Figure 19:
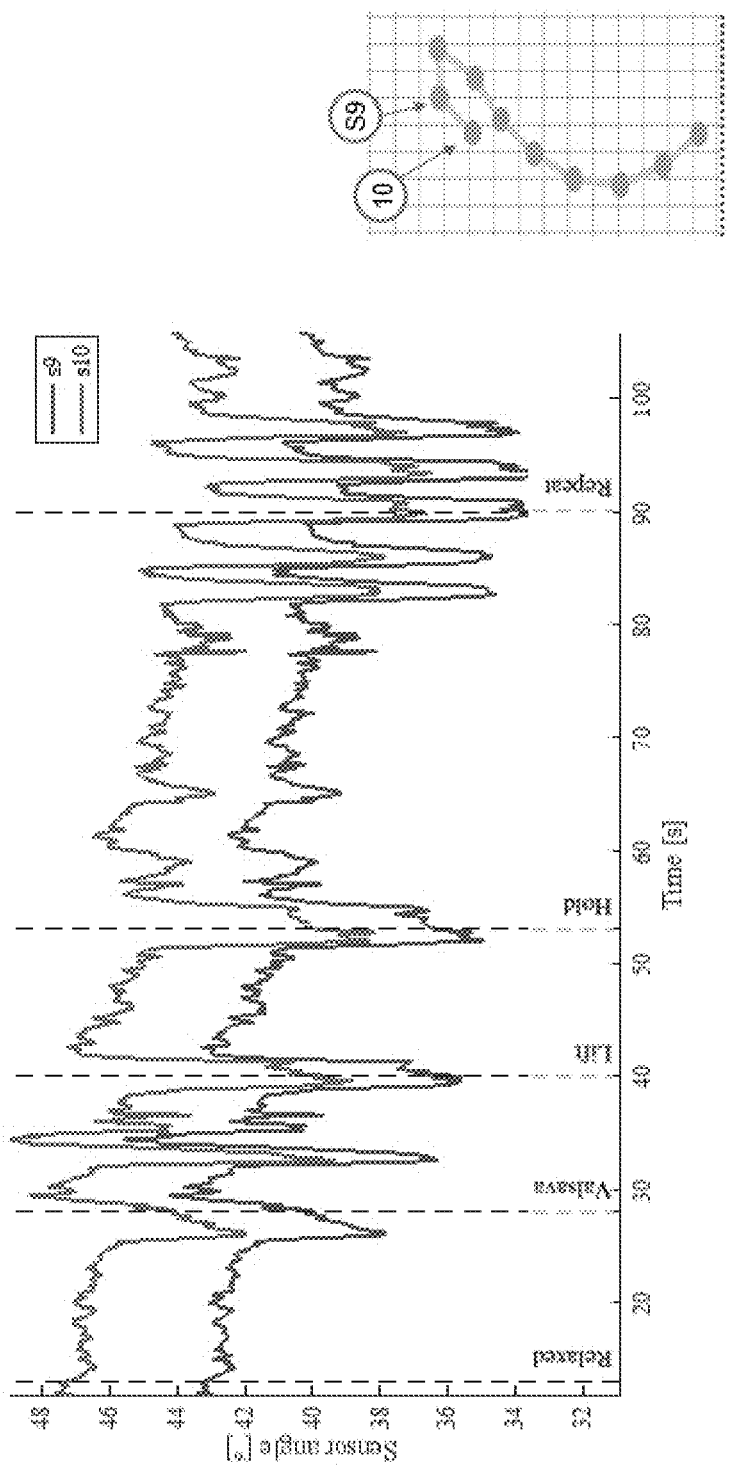
FIG. 19 is a graph showing the sensor angle for sensors S9 and S10 versus time in subject 006. Strong fornix signal is identified. The sensor data were generated using MEMS sensors.
Figure 25:
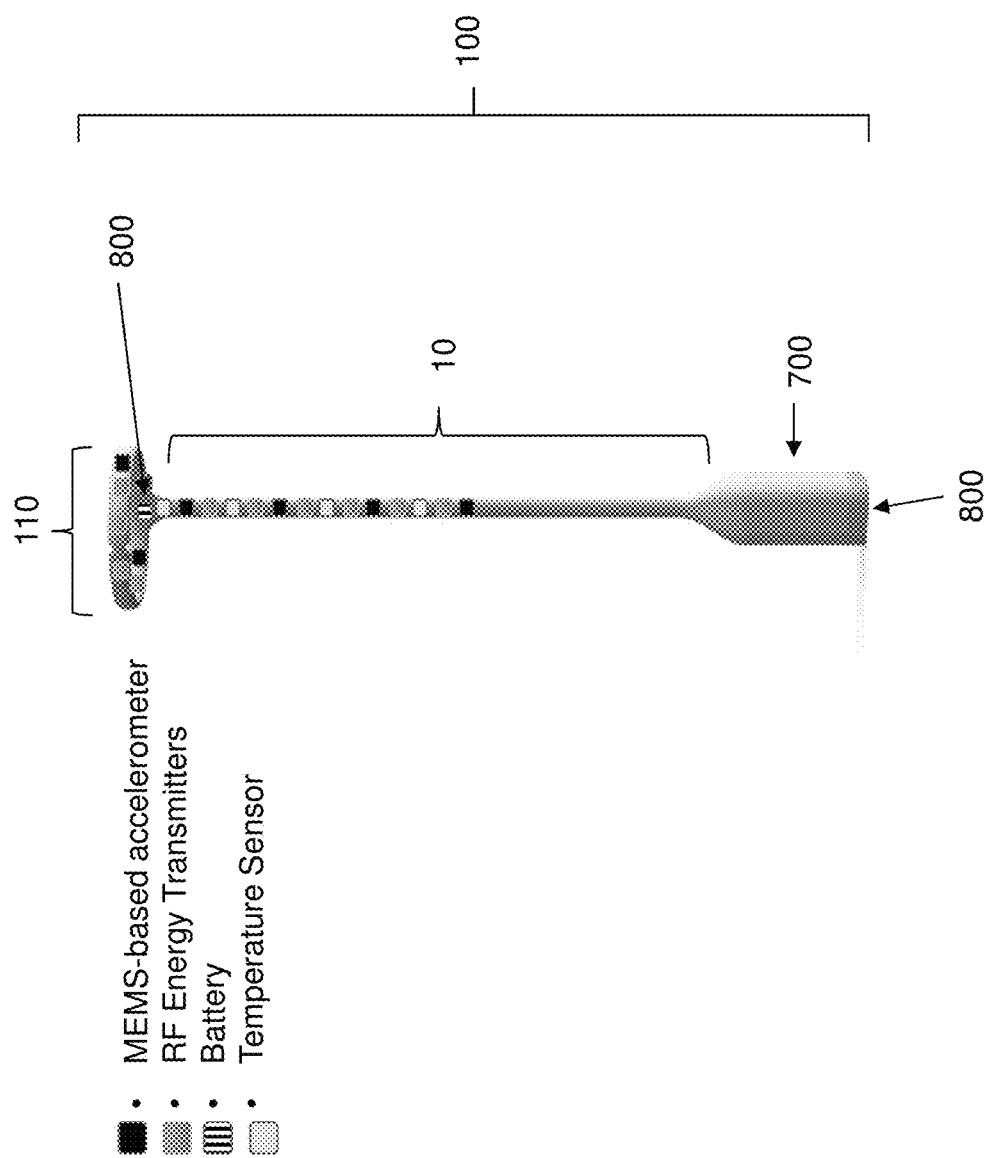
FIG. 25 is a schematic showing intravaginal device that 100 with main body 110, tether 10, circuit board 700, and battery 800. Intravaginal device 100 contains MEMS accelerometers, RF energy transmitters, and temperature sensors, positioned around main body 110 and along the length of tether 10. Battery 800 is located in main body 110.

The angles of each sensor may be tracked during pelvic floor movement. The angle of each individual sensor can be plotted on a time course (FIGS. 11-15, 18, and 19), and the time course may be annotated when certain pelvic floor exercises are performed (e.g., Valsalva maneuver, lift, hold, and repeat). The change in the sensor angle may reflect a change in orientation of the intravaginal device at that sensor location. Certain sensors may exhibit a stronger signal than others. For example, in FIG. 11, sensors 4-6 showed a significant change in angle upon performing a hold. However, the other sensors did not exhibit a significant angular change. Additionally, sensors 7 and 8 showed an inverted angular response to the rest of the sensors as the angle decreased (instead of increased) from a relaxed position. The angle of the fornix sensors 9 and 10 for that subject are shown in FIG. 12.

This type of data may be collected empirically for any given subject (Example 13). As shown in FIGS. 14-20, the data indicate that sensors S4-S6 were located at a position to yield the greatest signal change during pelvic floor maneuvers and the largest signal to noise ratio relative to the other sensors. As different female subjects have different vaginal lengths and physical shapes, some variability may exist as to the signal output. For each individual subject, the specific sensor position and orientation may yield different information and exhibit different levels of sensitivity. Thus, it may be possible to customize the size/length of the intravaginal device and the position of the sensors to optimize it for use for a certain subject. These data can help guide optimal placement of sensors in the most important positions of the intravaginal device to correctly correlate angular changes associated with specific pelvic floor disorders. In some instances, a sensor placed at a position that is approximately halfway between the introitus of the vagina and the cervix or vaginal cuff produces a strong signal.

Methods of Treating a Pelvic Floor Disorder with an Intravaginal Device of the Invention Configured to Deliver a Pharmaceutical Agent A female patient can use a device of the invention configured to deliver at least one (e.g., 1, 2, 3, 4, 5, or more) pharmaceutical agent in order to treat, inhibit, or reduce the development of or progression of a PFD, or other disease or condition, such as those described herein, in a similar fashion as described above. In some instances, an intravaginal device of the invention may be configured to deliver a pharmaceutical agent by connecting a tether module that includes a delivery module or component, inner core, reservoir, coating layer, and/or gel. In some instances, an intravaginal device of the invention may be configured to deliver a pharmaceutical agent by connecting a sleeve that includes a delivery module or component, inner core, reservoir, coating layer, and/or gel. The device can be inserted into the vagina of the individual and a pharmaceutical agent may be delivered to the tissues of the vagina, e.g., before, after, or during the engagement of or relaxation of a PF muscle (e.g., the levator ani (e.g., the pubococcygeus, ileococcygeus, coccygeus, and puborectalis muscles) and the associated connective tissues, which span a spheric form from the pubic bone anteriorly to the sacrum posteriorly and to the adjoining bony structure joining these two bones). The individual can also be monitored using the intravaginal device. Treatment with the device to deliver a pharmaceutical agent may reduce the frequency of occurrence and/or severity of at least one (e.g., 1, 2, 3, 4, 5, 6, 7, 8, 9, 10, or more) symptom of a pelvic floor disorder. In particular, treatment includes monitoring the performance of a PFL and/or PFR using the device over a treatment period during which time the pharmaceutical agent may be delivered, e.g., constantly or periodically. The device may deliver a pharmaceutical agent over a period of time ranging from about one week to about three months (e.g., about 1-week, 2-weeks, 3-weeks, 4-weeks, 2-months, or 3-months, e.g., about 7-21 days, 7-35 days, 7-49 days, 7-63 days, 7-77 days, 7-91 days, or 7-105 days, e.g., about 2-8 weeks).

Methods of Combination Treatment

A female patient having, e.g., a PFD and/or another disease or condition, such as those described herein, can use a device of the invention configured to deliver at least one (e.g., 1, 2, 3, 4, 5, or more) pharmaceutical agent in order to treat, inhibit, or reduce the development of or progression of the PFD and/or the disease or condition of the vaginal tissue in a similar fashion as described above. The device can be inserted into the vagina of the individual and a pharmaceutical agent may be delivered to the tissues of the vagina, e.g., before, after, or during the engagement of or relaxation of a PF muscle (e.g., the levator ani, e.g., the pubococcygeus, ileococcygeus, coccygeus, and puborectalis muscles) and the associated connective tissues, which span a spheric form from the pubic bone anteriorly to the sacrum posteriorly and to the adjoining bony structure joining these two bones). The individual can also be monitored with the intravaginal device. Delivery of a pharmaceutical agent using the device may reduce the frequency of occurrence and/or severity of at least one (e.g., 1, 2, 3, 4, 5, 6, 7, 8, 9, 10, or more) symptom of the PFD and/or the additional disease or condition. The device may be configured to deliver a combination of pharmaceutical agent, e.g., a compatible combination of pharmaceutical agents to treat both the PFD and the additional disease or condition of the user. In particular, treatment includes monitoring the performance of a PFL and/or PFR using the device over a treatment period during which time the pharmaceutical agent may be delivered, e.g., constantly or periodically. The device may deliver a pharmaceutical agent over a period of time ranging from about one week to about three months (e.g., about 1-week, 2-weeks, 3-weeks, 4-weeks, 2-months, or 3-months, e.g., about 7-21 days, 7-35 days, 7-49 days, 7-63 days, 7-77 days, 7-91 days, or 7-105 days, e.g., about 2-8 weeks).

Methods of Real-Time Monitoring (Live-Mode)

A female patient using an intravaginal device of the invention that is configured to provide real-time monitoring of the overall health status of a user's urogenital system and/or pelvic floor (e.g., the muscle fibers of the levator ani, e.g., the pubococcygeus, ileococcygeus, coccygeus, puborectalis muscles and associated connective tissues) may be able to prevent or reduce the development and/or reoccurrence of a PFD and/or another disease or condition, such as those described herein.

An intravaginal device that is configured to monitor, e.g., muscle movement (e.g., a PFL and/or PFL, a muscle strain, a muscle stretch, and/or a muscle contraction), muscle quality, muscle strength, and/or pressure, may be able to provide feedback to a user and/or to a medical practitioner overseeing the user's treatment in real-time based on (i) daily activities that may reduce and/or improve the efficacy of a pelvic floor muscle training program with an intravaginal device of the invention; (ii) optimal times (e.g., in response to the performance of a daily activity) for the administration of a pharmaceutical agent; and/or (iii) alterations that may be made to a pelvic floor treatment program (e.g., increasing the frequency and/or intensity of a pelvic floor training program that includes the performance of a series of PFLs and/or PFRs) to increase the efficacy of the treatment program. In particular, an intravaginal device of the invention may measure changes (e.g., increases and/or decreases) in, e.g., muscle movement (e.g., a PFL and/or PFL, a muscle strain, a muscle stretch, and/or a muscle contraction), muscle quality, muscle strength, and/or pressure of about 1%, 2%, 3%, 4%, 5%, 6%, 7%, 8%, 9%, 10%, 20%, 30%, 40%, 50%, 60%, 70%, 80%, 90%, or more as compared to baseline values obtained, e.g., during a calibration of the intravaginal device, or known in the art.

An intravaginal device that is configured to monitor, e.g., the level of a toxin and/or hormone, pH, temperature, and/or humidity, can provide feedback to a user and/or to a medical practitioner overseeing the user's treatment on (i) the onset and/or progression of a PFD and/or another disease and/or condition affecting a user's urogenital system and pelvic floor health; and (ii) the effectiveness of a treatment program including the administration of pharmaceutical agent, as described herein, by measuring changes in the level of a toxin, a hormone, pH, and/or humidity associated with a disease state. In particular, an intravaginal device of the invention can measure changes (e.g., increases and/or decreases) in, e.g., the level of a toxin and/or hormone, pH, temperature, and/or humidity of about 1%, 2%, 3%, 4%, 5%, 6%, 7%, 8%, 9%, 10%, 20%, 30%, 40%, 50%, 60%, 70%, 80%, 90%, or more as compared to baseline values obtained, e.g., during a calibration of the intravaginal device, or known in the art.

Methods of Use with an Additional Device

A female patient having, e.g., a PFD and/or another disease or condition, such as those described herein, can use a device of the invention in combination with an additional device that, in some instances, is configured to deliver at least one (e.g., 1, 2, 3, 4, 5, or more) pharmaceutical agent in order to treat, inhibit, or reduce the development of or progression of the PFD and/or the disease or condition of the vaginal tissue in a similar fashion as described above. However, in some instances, an additional device that may be used in combination with an intravaginal device of the invention is not configured to deliver a pharmaceutical agent.

In some instances, the additional device can be inserted into the vagina of the individual and a pharmaceutical agent may be delivered to the tissues of the vagina, e.g., before, after, or during the use of an intravaginal device of the invention to measure the engagement or relaxation of a PF muscle (e.g., the levator ani, e.g., the pubococcygeus, ileococcygeus, coccygeus, and puborectalis muscles, and the associated connective tissues). The effectiveness of treatment with an additional device may also be monitored by an intravaginal device of the invention. For example, an intravaginal device of the invention configured to detect a hormone and/or a toxin may be able to monitor the progression the disease and/or condition being treated by the additional device. Delivery of a pharmaceutical agent using an additional device in combination with an intravaginal device of the invention may reduce the frequency of occurrence and/or severity of at least one (e.g., 1, 2, 3, 4, 5, 6, 7, 8, 9, 10, or more) symptom of the PFD and/or the additional disease or condition. The additional device may be configured to deliver a combination of pharmaceutical agents, e.g., a compatible combination of pharmaceutical agents to treat both the PFD and/or the additional disease or condition of the user. In particular, treatment includes monitoring the performance of a PFL and/or PFR using an intravaginal device of the invention over a treatment period with an additional device during which time the pharmaceutical agent may be delivered, e.g., constantly or periodically. The additional device may deliver a pharmaceutical agent one or more times over a period of time (e.g., as timed release or programmed release) ranging from about one week to about three months (e.g., about 1-week, 2-weeks, 3-weeks, 4-weeks, 2-months, or 3-months, e.g., about 7-21 days, 7-35 days, 7-49 days, 7-63 days, 7-77 days, 7-91 days, or 7-105 days, e.g., about 2-8 weeks). Non-limiting examples of additional devices that may be used in combination with an intravaginal device of the invention include, but are not limited to, a vaginal pessary, a vaginal and/or anal suppository, a catheter, a bladder neck support device, a sponge, a menstrual device (e.g., a tampon or a menstrual cup), a vaginal stimulator (e.g., a device that contains one or more (e.g., 1, 2, 3, 4, 5, 6, 7, 8, 9, or 10 electrodes; a device that contains a vibrator; and/or a device that contains a light emitting source), a vaginal dilator, and/or a device that contains a camera.

EXAMPLES

The following examples are put forth so as to provide those of ordinary skill in the art with a description of how the compositions and methods claimed herein are performed, made, and evaluated, and are intended to be purely exemplary for use in the compositions and methods of the invention and are not intended to limit the scope of what the inventors regard as their invention.

Example 1. Treatment of an Individual Having Urinary Incontinence (UI) with an Intravaginal Device An intravaginal device and/or system (e.g., an intravaginal device similar to that shown in FIG. 1) may be used to treat an individual having urinary incontinence (UI). The individual may have been identified as having a risk for developing UI (e.g., a subject who has recently experienced vaginal childbirth) or have been diagnosed as having UI by a medical practitioner. Alternatively, the individual experiencing the symptoms of UI may self-identify as having a need to train her pelvic floor (PF) muscles to reduce the frequency and/or the severity of UI symptoms. The individual may obtain the device from a medical practitioner or from a retail outlet (e.g., a pharmacy).

The individual begins by inserting the intravaginal device into the vagina (e.g., by using an insertion tool) and positioning it proximal to the cervix or, for an individual with a hysterectomy, to the vaginal cuff.
The individual will then perform a series of pelvic floor lifts (PFLs) to strengthen her pelvic floor muscles. The individual can perform a series of PFLs for 15 seconds and then rests the muscles for 15 seconds, repeating the series for a total of 5 times over 2.5 minutes. The device measures and collects results via sensors. The individual will perform this training program at least once a day, but preferably three times per day for about one week to about three months. Over time, symptoms resolve. At the completion of the training program the device can be removed.

Example 2. Treatment of an Individual Having Anal or Fecal Incontinence with an Intravaginal Device An intravaginal device and/or system (e.g., an intravaginal device similar to that shown in FIG. 1) may be used to treat an individual having anal or fecal incontinence (FI). The individual may have been identified as having a risk for developing FI (e.g., a subject who has recently experienced vaginal childbirth) or have been diagnosed as having FI by a medical practitioner. Alternatively, the individual experiencing the symptoms of UI may self-identify as having a need to train her pelvic floor (PF) muscles to reduce the frequency and/or the severity of UI symptoms. The individual may obtain the device from a medical practitioner or from a retail outlet (e.g., a pharmacy).

The individual begins by inserting the intravaginal device into the vagina (e.g., by using an insertion tool) and positioning it proximal to the cervix or, for an individual with a hysterectomy, to the vaginal cuff. The patient may use the intravaginal device as outlined in FIG. 1.

The individual will then perform a series of pelvic floor lifts (PFLs) to strengthen her pelvic floor muscles. The individual can perform a series of PFLs for 15 seconds and then rests the muscles for 15 seconds, repeating the series for a total of 5 times over 2.5 minutes. The device measures and collects results via sensors. The individual will perform this training program at least once a day, but preferably three times per day for about one week to about three months. Over time, symptoms resolve. At the completion of the training program the device can be removed.

Example 3. Treatment of an Individual Having Sexual Dysfunction with an Intravaginal Device An intravaginal device and/or system (e.g., an intravaginal device similar to that shown in FIG. 1) may be used to treat a sexual dysfunction, such as caused by high pelvic floor muscle tone. The individual may have been diagnosed as having a sexual dysfunction by a medical practitioner. Alternatively, the individual experiencing the symptoms of sexual dysfunction may self-identify as having a need to train her pelvic floor (PF) muscles to reduce the frequency and/or the severity of the symptoms of sexual dysfunction (e.g., painful intercourse and vaginal laxity).

The individual begins by inserting the intravaginal device into the vagina (e.g., by using an insertion tool) and positioning it proximal to the cervix or, for an individual with a hysterectomy, to the vaginal cuff. The patient may use the intravaginal device as described herein.

The individual will then use the device to relax the muscles of the pelvic floor. The individual can perform a series of PFR exercises. The individual will perform this training program at least once a day, but preferably three times per day for about one week to about three months. Over time, symptoms resolve. At the completion of the training program the device can be removed.

Example 4. Treatment of an Individual Having a Neurological Disease or Injury with an Intravaginal Device An intravaginal device and/or system (e.g., an intravaginal device similar to that shown in FIG. 1) may be used to treat a pelvic floor disorder (PFD) in an individual having a neurological condition, such as multiple sclerosis (MS).

The individual begins by inserting the intravaginal device into the vagina (e.g., by using an insertion tool) and positioning it proximal to the cervix or, for an individual with a hysterectomy, to the vaginal cuff. The patient may use the intravaginal device as described herein.

The individual will then perform a series of pelvic floor lifts (PFLs) to strengthen her pelvic floor muscles. The individual can perform a series of PFLs for 15 seconds and then rests the muscles for 15 seconds, repeating the series for a total of 5 times over 2.5 minutes. The device measures and collects results via sensors. The individual will perform this training program at least once a day, but preferably three times per day for about one week to about three months. The individual may also use the device to track her experience of MS related PFD symptoms, such as the number of times she experiences urine or anal or fecal leakage per day. Over time, symptoms resolve. At the completion of the training program the device can be removed.

Example 5. Treatment of an Individual Having a Pelvic Floor Disorder with an Intravaginal Device Containing an Electrical Impedance Myography (EIM) Sensor An intravaginal device and/or system (e.g., an intravaginal device similar to that shown in FIG. 1) may contain an electrical impedance myography (EIM) sensor, such as a SKULPT® sensor, and may be used to treat an individual having a pelvic floor disorder.

The individual begins by inserting the intravaginal device into the vagina (e.g., by using an insertion tool) and positioning it proximal to the cervix or, for an individual with a hysterectomy, to the vaginal cuff. The patient may use the intravaginal device as described herein.

The individual will then perform a series of pelvic floor lifts (PFLs) to strengthen her pelvic floor muscles. The individual can perform a series of PFLs for 15 seconds and then rests the muscles for 15 seconds, repeating the series for a total of 5 times over 2.5 minutes. The device measures and collects results via the EIM sensors. Using the data collected from the EIM sensors, the intravaginal device provides the individual with a muscle quality score (e.g., a score reflective of muscle fiber density and organization). The individual will perform this training program at least once a day, but preferably three times per day for about one week to about three months. By using the intravaginal device, the individual may increase her muscle quality score. Over time, symptoms resolve. The device can be removed by the individual upon completion of the training program.

Example 6. Treatment of an Individual Having a Pelvic Floor Disorder with an Intravaginal Device Containing a Light Detection and Ranging (LiDAR) Sensor An intravaginal device and/or system (e.g., an intravaginal device similar to that shown in FIG. 1) containing a light detection and ranging (LiDAR) sensor may be used to treat an individual having a pelvic floor disorder.

The individual begins by inserting the intravaginal device into the vagina (e.g., by using an insertion tool) and positioning it proximal to the cervix or, for an individual with a hysterectomy, to the vaginal cuff. The patient may use the intravaginal device as described herein.

The individual will then perform a series of pelvic floor lifts (PFLs) to strengthen her pelvic floor muscles. The individual can perform a series of PFLs for 15 seconds and then rests the muscles for 15 seconds, repeating the series for a total of 5 times over 2.5 minutes. The device measures and collects results via the LiDAR sensors. Using the data collected from the LiDAR sensors, the intravaginal device provides the individual with three-dimensional (3D) model of her pelvic floor and vaginal tissues, which can be displayed to a user on a wirelessly connected electronic device via a user interface. A 3D model can be generated at the start of treatment, e.g., a 3D reference model, and periodically throughout, or after, the treatment program. Based on the 3D models, e.g., a 3D model generated in substantially real-time, the user may be guided to perform and or make corrections to her execution of pelvic floor lifts and/or relaxations. Movement data collected by the LiDAR sensors may also be used to monitor the performance of pelvic floor lifts and/or relaxations and provide feedback to the user. The individual will perform this training program at least once a day, but preferably three times per day for about one week to about three months. Over time, symptoms resolve. At the completion of the training program, the device can be removed.

Example 7. Treatment of an Individual Having Pelvic Organ Prolapse with an Intravaginal Device An intravaginal device and/or system (e.g., an intravaginal device similar to that shown in FIG. 1) may be used to treat an individual having pelvic organ prolapse (e.g., uterine prolapse). An individual diagnosed as having a pelvic organ prolapse (e.g., uterine prolapse) by a medical practitioner may be prescribed an intravaginal device of the invention configured to administer a dose of a pharmaceutical agent(s), such as a muscle stimulator. The individual may obtain the device from the medical practitioner or from a retail outlet (e.g., a pharmacy).

The individual begins treatment by inserting the intravaginal device into the vagina (e.g., by using an insertion tool) and positioning the device proximal to the cervix or, for an individual with a hysterectomy, the vaginal cuff. The patient may use the intravaginal device as described herein. The intravaginal device may be configured to release the muscle stimulator, e.g., during the performance of a pelvic floor training exercise. Additionally, or alternatively, the intravaginal device may be configured to release an estrogen-compound (e.g., estradiol) to restore the loss of estrogen to vaginal tissues that may be weakened, for example, by age.

The individual will then perform a series of pelvic floor lifts (PFLs) to strengthen her pelvic floor muscles. The individual can perform a series of PFLs for 15 seconds and then rest the muscles for 15 seconds, repeating the series for a total of 2-5 times over 30 seconds to 2.5 minutes. The device measures and collects results via sensors, which can direct the release of the muscle stimulator, e.g., during the performance of a PFL. The individual can perform this training program at least once a day, but preferably three times per day for about one week to about three months. Over time, symptoms resolve. If necessary, the intravaginal device (e.g., a refillable reservoir arranged within the intravaginal device), may be refilled to continue treatment with the muscle stimulator and/or the estrogen-related pharmaceutical agent. At the completion of the training program the device can be removed.

Example 8. Monitoring of an Individual's Pelvic Floor Health Status During Daily Activities to Reduce Reoccurrence of a PFD An intravaginal device and/or system (e.g., an intravaginal device similar to that shown in FIG. 1) may be used to perform daily (e.g., real-time) monitoring of the overall health status of a user's urogenital system and/or pelvic floor (e.g., the muscle fibers of the levator ani, e.g., the pubococcygeus, ileococcygeus, coccygeus, puborectalis muscles and associated connective tissues) who has previously experienced a PFD (e.g., urinary incontinence) and who is at risk of, but not currently experiencing, the reoccurrence of, e.g., urinary incontinence symptoms. A medical practitioner may prescribe an intravaginal device of the invention as a prophylactic and diagnostic aid. The individual may obtain the device from the medical practitioner or from a retail outlet (e.g., a pharmacy). In some instances, for example, when an individual already owns a base model of the intravaginal device (e.g., the main body of the intravaginal device) the individual may need to obtain an expansion set (e.g., a tether or one or more tether modules or separable tether portions) that can be used to add the additional sensors and functionality required to perform daily monitoring. Following the instructions provided with the expansion set, and available through the Application, a user may connect the tether or the one or more tether modules or separable tether portions to the main body of the intravaginal device.

The individual begins treatment by inserting the intravaginal device into the vagina (e.g., by using an insertion tool) and positioning the device proximal to the cervix or, for an individual with a hysterectomy, the vaginal cuff. The patient may use the Application to activate Live Mode to perform daily monitoring of the overall health status of the user's urogenital system and/or pelvic floor. The Live Mode provides real time visualization of the pelvic floor musculature that can be used to train or educate the patient on the correct way to perform pelvic floor exercises. For example, real time visualization during Live Mode can help a patient to understand how to activate muscles in the pelvic floor that achieve "lift" rather than a "squeeze" without a lifting movement. Activation of the pelvic floor muscles that achieve "lift," which helps to strengthen the pelvic floor muscles and to improve the pelvic floor health of the patient, can be observed when the sensor(s) readout of the device (e.g., MEMS sensor(s) readout) shows movement of the device in an upward and frontward (e.g., caudal/anterior direction). The pelvic floor muscles shorten as they become stronger, which translates into a lifting motion during PFMT. Using the sensors arranged with the main body and/or tether, the intravaginal device can collect data as the user performs her daily activities and will provide feedback to the user and/or to the medical practitioner overseeing her treatment.

If the intravaginal device detects a daily activity being performed that may weaken a user's pelvic floor muscles, the intravaginal device can notify the individual and advise them to cease performance of the detected activity. In some instances, the intravaginal device may advise and/or schedule a reminder for the individual to perform a series of pelvic floor lifts (PFLs) to strengthen her pelvic floor muscles in response to data collected during daily monitoring using Live Mode. The individual may then perform a series of PFLs for 15 seconds and then rest the muscles for 15 seconds, repeating the series for a total of 2-5 times over 30 seconds to 2.5 minutes. The individual can perform this training program when instructed to by the intravaginal device to prevent the reoccurrence of a PFD (e.g., urinary incontinence). Over time, the feedback provided during the use of an intravaginal device may help an individual to identify and reduce the performance of daily activities that may lead to the reoccurrence and/or development of a PFD, (e.g., urinary incontinence).

Example 9. Monitoring of an Individual's Hormone Levels to Detect Cancer

An intravaginal device and/or system (e.g., an intravaginal device similar to that shown in FIG. 1) may be used to perform daily (e.g., real-time) monitoring of the overall health status of a user's urogenital system and/or pelvic floor (e.g., the muscle fibers of the levator ani, e.g., the pubococcygeus, ileococcygeus, coccygeus, puborectalis muscles and associated connective tissues) who has previously experienced a PFD (e.g., urinary incontinence) and who is at risk of, but not currently experiencing, the reoccurrence of, e.g., urinary incontinence symptoms. A medical practitioner may prescribe an intravaginal device of the invention that is configured to measure hormone levels to a patient at risk of developing uterine, cervical, and/or vaginal cancer (e.g., a patient who has previously been treated for a uterine or cervical cancer, but who is currently in remission). The individual may obtain the device from the medical practitioner or from a retail outlet (e.g., a pharmacy).

The individual begins treatment by inserting the intravaginal device into the vagina (e.g., by using an insertion tool) and positioning the device proximal to the cervix or, for an individual with a hysterectomy, the vaginal cuff. The patient may use the Application to active Live Mode to perform daily monitoring of the overall health status of the user's urogenital system and/or pelvic floor, and in particular to measure the level of hormones associated with the development of uterine, cervical, and/or vaginal cancer. The intravaginal device can collect data on hormone level(s) as the user performs her daily activities and can provide feedback to the user and/or to the medical practitioner overseeing her treatment.

If the intravaginal device detects a change (e.g., an increase and/or a decrease of about 1%, 2%, 3%, 4%, 5%, 6%, 7%, 8%, 9%, 10%, 20%, 30%, 40%, 50%, 60%, 70%, 80%, 90% or more) in the level of a hormones (e.g., estrogen) that is associated with the onset, persistence, and/or malignancy of a uterine, cervical, and/or vaginal cancer, the intravaginal device can notify the individual of the benefit of scheduling an appointment with her medical practitioner to evaluate her cancer status. In some instances, the intravaginal device may advise the medical practitioner directly and/or schedule an appointment for the patient so her cancer status can be evaluated, Example 10. Monitoring of an Individual's Toxin Levels to Detect an Infection An intravaginal device and/or system (e.g., an intravaginal device similar to that shown in FIG. 1) may be used to perform daily monitoring of the overall health status of a user's urogenital system and/or pelvic floor (e.g., the muscle fibers of the levator ani, e.g., the pubococcygeus, ileococcygeus, coccygeus, puborectalis muscles and associated connective tissues) who is at risk of developing a fungal infection, such as a yeast infection. A medical practitioner may prescribe an intravaginal device of the invention as a diagnostic aid. The individual may obtain the device from the medical practitioner or from a retail outlet (e.g., a pharmacy).

The individual begins treatment by inserting the intravaginal device into the vagina (e.g., by using an insertion tool) and positioning the device proximal to the cervix or, for an individual with a hysterectomy, the vaginal cuff. The patient may use the Application to active Live Mode to perform daily (e.g., real-time) monitoring of the overall health status of the user's urogenital system and/or pelvic floor, and in particular to monitor the level of toxins associated with the onset of a fungal infection, e.g., a yeast infection. Using the sensors arranged with the main body and/or tether will then collect data as the user performs her daily activities and can provide feedback to the user and/or to the medical practitioner overseeing her treatment.

If the intravaginal device detects a toxin level known to be associated with the onset of an infection, the intravaginal device can notify the individual of the benefit of scheduling an appointment with her medical practitioner to evaluate her health status. In some instances, the intravaginal device may advise the patient to administer an appropriate pharmaceutical agent to treat the developing infection. In some instances, the intravaginal device may notify the patient to connect a tether or a tether module configured to administer the pharmaceutical agent or recommend that the patient purchase, e.g., an over-the-counter anti-fungal agent that may be administered by the patient. For example, a patient may insert a suppository, e.g., a miconazole suppository, into her vagina while continuing to use the intravaginal device to monitor the toxin level throughout the treatment period. Over time, the feedback provided during the use of an intravaginal device may help an individual to identify and reduce the reoccurrence of fungal infections.

Figure 8:
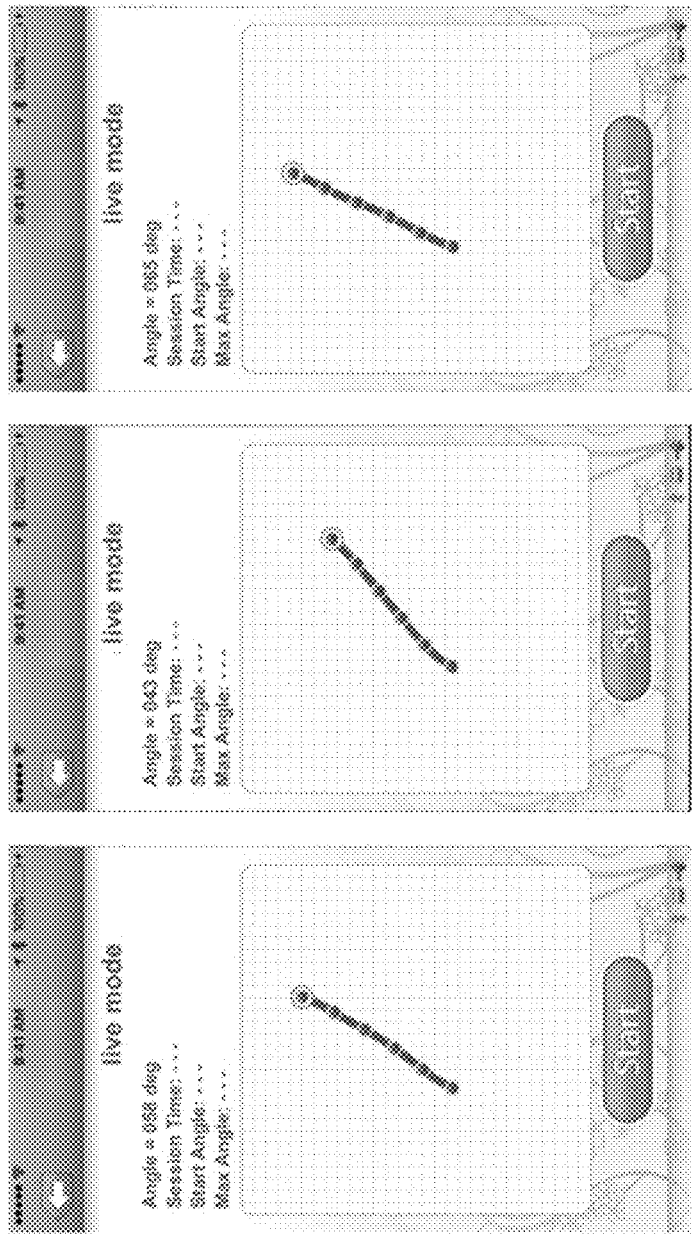
FIGS. 8A-8C is a set of three device application screenshots in a subject using an intravaginal device, which illustrate how vaginal angles may be visualized in live mode.

Example 11. Real-Time Data Output in Live Mode and Use with a Smartphone Application An intravaginal device of the invention is connected to a transmitter box that wirelessly (via Bluetooth) sends the positional data gathered from the device sensors to a smartphone or computer that communicates to the patient through a smartphone application (see, e.g., FIGS. 8A-8C). The shape of the vagina (data from the MEMS sensors in the device) reflects the position of the patient's pelvic floor in her body. The data is captured as a score based on the angles of the sensors. The score is a measure of the strength of the patient's pelvic floor muscles and increases as she performs her training over time. The data created by the device is transmitted to a centralized database creating a personal health record for the patient, providing care and measurable results.

This data can provides predictive information that notifies patients and health care professionals about the potential need for various treatment options to improve the patient's quality of life. For example, the changes observed in patients who have hypermobility are markedly different from patients that do not have hypermobility (e.g., associated with stress urinary incontinence). By establishing a baseline on a patient using the device and the database of information on the patient, one could monitor the patient's pelvic floor descent or damage over time. Therefore, the patient can be treated before the damage needs to be corrected through surgical means.

A device of the invention is used to characterize the change in health state over time of a female patient. A female patient with stage III prolapse uses a device of the invention. After insertion of the device for the first time, the sensors read out that the device is positioned at a vaginal angle of ~20°. When performing a PFL, the angle of the sensors moves toward 45°. She performs a series of exercises 1-10 times a day (30 seconds-3 minutes per session) over the course of 3 weeks. After the 3 week treatment period, the woman is able to lift the device such that the vaginal angle is 30°. This change in angle suggests that the woman has improved from stage III prolapse to stage II prolapse.

Example 12. Tracking Metrics of Sensor Readout as Patient Improves Pelvic Muscle Strength A patient with symptoms of urinary incontinence uses an intravaginal device for ~2.5 minutes twice daily. After performing the exercises, the application computes an average weekly score, which increases from a baseline (screen) of 9 to a range of 44-52, reflecting the vaginal angle changes during the lifting of the pelvic floor during exercises. An increase in score correlates with an increase in pelvic muscle strength. The application can also track endurance, which calculates the duration of time holding a lift during an exercise. After a 3 week exercise regimen, the incontinence issue is assessed and, in many cases, would be resolved.

Example 13. Determining Optimal Sensor Positioning

An intravaginal device (see FIG. 5) was used to characterize specific sensor placement within the intravaginal device (e.g., within main body 110 or tether 10) in ten subjects; the results of experiments using this device are shown in FIGS. 11-20. The sensors in the main body were within the anterior fornix, lateral fornices and posterior fornix. The sensors in the tether 10 were within the posterior fornix (shared by the main body) and along the vaginal canal caudal to the fornices. The main body contained 5 sensors, while the tether contained 8 sensors (including the one shared with the main body). The subjects had a range of vaginal lengths; these subjects were studied to determine if a subset of the original 12 sensors consistently correlated with pelvic floor movement (e.g., PFL) when the subjects performed a variety of maneuvers and demonstrated superior signal-to-noise characteristics. As shown in FIGS. 11-20, the sensors in the fornix exhibited lower signal and provided less robust visualization of pelvic floor movement. Of the sensors in the more caudal portion of the vagina, sensors 4-6 exhibited a strong signal during movement of the pelvic floor and favorable signal-to-noise ratio, even in female subjects having different vaginal lengths and physical shapes. Thus, the placement of 2-3 sensors along the length of the tether of the intravaginal device, such that the sensors are positioned approximately mid-way in the vaginal canal, yields robust signal output. Intravaginal devices with this placement of sensors (e.g., accelerometers, such as MEMS sensors) can be used to diagnose abnormal pelvic floor movements and vaginal curvature associated with specific pelvic floor disorders.

Example 14. Delivery of RF Energy for Therapeutic Applications

An intravaginal device and/or system (e.g., such as the one shown in FIGS. 1 and 21-25) may contain one or more energy transmitters 210 (e.g., RF) and sensors 200 (e.g., temperature sensors) and may be used to treat an individual having a vaginal or pelvic floor disorder. RF transmitters may be positioned around main body 110 and along the length of tether 10. The individual begins by inserting intravaginal device 100 into the vagina (e.g., by using an insertion tool) and positioning it proximal to the cervix or, for an individual with a hysterectomy, to the vaginal cuff.

Figure 29:
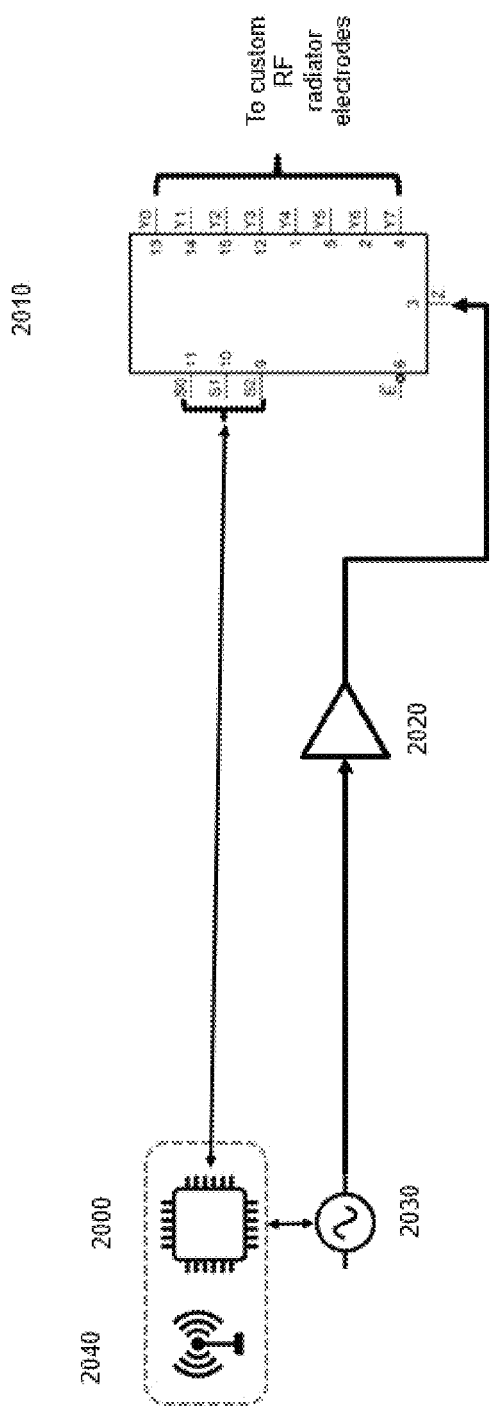
FIG. 29 is a schematic showing a power circuit, which can power one or more RF transmitters of intravaginal device 100 to provide therapeutic energy to vaginal tissue. The power circuit includes microcontroller 2000 and BLE radio 2040 (e.g. Nordic nRF52840) having a peak power consumption less than 20 mW and an average power consumption less than 100 µW, analog/RF multiplexer 2010 (e.g. Nexperia 74HCT4051) having a power consumption <1 mW, power amplifier 2020 (e.g. Texas Instruments OPA2677) having a frequency of 0-22 MHz @ gain of 20×, an output power of up to 9 W, and a power consumption of ~10 W, and a programmable oscillator or direct digital synthesizer 2030 (e.g. Analog Devices AD9833) having a frequency of 1 kHz-12.5 MHz and a peak power consumption of 12.65 mW.

The intravaginal device may be used for short of extended periods of time. RF transmitters distribute RF energy to different areas in the vagina. RF transmitters may operate at one or more frequencies in the range of 1 kHz to 50 MHz. The power level of the transmitters may vary from 10 mW to 300 W, depending on physician recommendations and the duration of therapy. Intravaginal device 100 may have sensors 200 that are temperature sensors and microcontroller 900 to automatically regulate the frequency and power level applied to regulate the appropriate temperature for optimal patient comfort and therapeutic activity. The device may connect to a peripheral device, such as a smart phone running an application capable of controlling the device, by means of a USB port, Bluetooth Low Energy, Wi-Fi, or a similar wired or wireless technology (FIG. 28). An application running on the peripheral device can be used by the patient or a physician to adjust the frequency, power level, and/or duration of treatment. The device may be battery powered or may be connected to an external power source, e.g., power box 810 (e.g., an external battery) or an AC outlet. An example of the circuitry that can be used to power the device is shown in FIG. 29.

In order to power energy transmitters 210 (e.g., RF transmitters), the device can be designed with a modular tether that is separable into two components (FIGS. 26-27). The top half of the device can remain inside the patient as a long-term wearable component 105, which contains ring 10 and part of tether 110. Tether 110 can be connected to a modular component of the tether, which can be configured as a separate short-term wearable device 115 that may have additional energy transmitters 210, such as RF transmitters, to apply RF therapy to the lower section of the vagina. Battery 800 may only power microcontroller 900, wireless radio 1300, and sensors 200, which may be accelerometers. Short term device 115 may come into physical contact with long-term device 105 to power transmitters 210, such as RF energy transmitters and recharge battery 800, if present. Alternatively, short-term device 115 may have a wireless power transmitter and long-term device 105 may have a wireless power receiver. Long-term 105 and short-term 115 devices may have magnetic and/or electrical (e.g., Ohmic) connections.

Example 15. Treatment of Skin Laxity

A patient with symptoms of urinary incontinence uses an intravaginal device having a ring and tether configuring with a radio frequency transmitter. The patient inserts the intravaginal device and turns on the RF transmitters at 5 W (10 V and 500 mA) for 20 minutes twice daily (5 minutes per area, 4 different areas). After turning on the radio frequency emitter, a smartphone application computes a thermal index to track how hot the intravaginal tissue becomes during treatment. The thermal energy extends to 10 $cm^2$ area in contact with the transmitters and 1-10 mm below the surface of the vaginal tissue. Following each use, a short term modular tether component attached to an external power source is attached the long term wearable device to recharge the internal battery. After a 6 week treatment regimen, the incontinence issue is assessed and resolved and the long-term intravaginal device is removed.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations for use in the compositions and methods of the invention following, in general, the principles for use in the compositions and methods of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:
1. An intravaginal device comprising 2, 3, 4, 5, 6, 7, 9, or 10 accelerometers disposed along a length of the device, wherein each of the accelerometers are separated by a distance of about 1.6 cm.
2. The intravaginal device of claim 1, wherein:
(a) the device is connected to an external power source;
(b) the device further comprises a microcontroller for receiving and storing data from the accelerometers;
(c) the device further comprises a wired transmitter and/or receiver for communicating data to an electronic device, optionally, wherein the transmitter and/or receiver can wirelessly communicate the data to the electronic device;
(d) the device further comprises a transmitter and/or receiver located in an external housing connected to the intravaginal device by a detachable cable;
(e) the device further comprises a power source connected to the accelerometers;
(f) the device further comprises one or more sensors selected from the group consisting of an accelerometer, gyroscope, micro-electro-mechanical systems (MEMS) sensor, G-sensor, tilt sensor, rotation sensor, a light detecting sensor, such as a light detecting and ranging (LiDAR) sensor, and electrical impedance myography (EIM) sensor;
(g) a length of the device is about 3 cm to about 50 cm;
(h) an angle formed by a line drawn between the position of at least two of the accelerometers in the device tether and the horizon defines a vaginal angle; and/or
(i) the device comprises a flexible, biocompatible material.
3. The intravaginal device of claim 2, wherein:
(i) the electronic device comprises a display;
(ii) the transmitter and receiver are configured for use with a Bluetooth and/or Wi-Fi enabled electronic device;
(iii) the electronic device is a computer, tablet, smartphone, or smart watch; and/or
(iv) the intravaginal device is configured to send data to and receive data from the electronic device.
4. The intravaginal device of claim 2, wherein:
(i) the intravaginal device comprises a combination of sensors of differing types; and/or
(ii) the intravaginal device further comprises at least one additional sensor within the device selected from the group consisting of a pressure sensor, a muscle quality sensor, a muscle strength sensor, a pH sensor, a humidity sensor, a temperature sensor, a hormone sensor, and a toxin sensor.
5. The intravaginal device of claim 2, wherein:
the length of the device is about 25.5 cm.
6. A system comprising the intravaginal device of claim 1 and a graphical user interface.
7. The system of claim 6, wherein the graphical user interface is tethered wirelessly to the intravaginal device; and/or wherein the system further comprises:
(a) a transmitter and receiver;
(b) a detachable cable;
(c) a tool for insertion of the intravaginal device;
(d) an electronic device; and/or
(e) a database.
8. The intravaginal device of claim 3, wherein the display is a graphical user interface.
9. The intravaginal device of claim 8, wherein the graphical user interface comprises a touch user interface.
10. The intravaginal device of claim 1, wherein the device comprises six accelerometers.

* * * * *

UNITED STATES PATENT AND TRADEMARK OFFICE
CERTIFICATE OF CORRECTION

| | | |
|---|---|---|
| PATENT NO. | : 12,220,345 B2 | Page 1 of 1 |
| APPLICATION NO. | : 16/759060 | |
| DATED | : February 11, 2025 | |
| INVENTOR(S) | : Marc D. Beer et al. | |

It is certified that error appears in the above-identified patent and that said Letters Patent is hereby corrected as shown below:

In the Claims

Column 78, Claim 2, Line 18, replace "of at least two of the accelerometers in the device tether" with --of at least two of the accelerometers in the device--.

Signed and Sealed this
Third Day of June, 2025

Coke Morgan Stewart
*Acting Director of the United States Patent and Trademark Office*